United States Patent
Chen et al.

(10) Patent No.: US 9,796,705 B2
(45) Date of Patent: Oct. 24, 2017

(54) FUSED TRICYCLIC COMPOUNDS AND METHODS OF USE THEREOF FOR THE TREATMENT OF VIRAL DISEASES

(71) Applicant: Merck Sharp & Dohme Corp., Rahway, NJ (US)

(72) Inventors: Kevin X. Chen, Cambridge, MA (US); Stuart B. Rosenblum, West Orange, NJ (US); Joseph A. Kozlowski, Princeton, NJ (US); F. George Njoroge, Carmel, IN (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/276,425

(22) Filed: Sep. 26, 2016

(65) Prior Publication Data

US 2017/0008879 A1    Jan. 12, 2017

Related U.S. Application Data

(63) Continuation of application No. 13/518,336, filed as application No. PCT/US2010/061205 on Dec. 20, 2010, now abandoned.

(60) Provisional application No. 61/289,204, filed on Dec. 22, 2009.

(51) Int. Cl.
| | |
|---|---|
| C07D 403/14 | (2006.01) |
| C07D 403/04 | (2006.01) |
| C07D 403/08 | (2006.01) |
| A61K 31/4184 | (2006.01) |
| A61K 31/454 | (2006.01) |
| A61K 45/06 | (2006.01) |
| C07D 409/14 | (2006.01) |
| C07D 401/14 | (2006.01) |

(52) U.S. Cl.
CPC ........ *C07D 403/14* (2013.01); *A61K 31/4184* (2013.01); *A61K 31/454* (2013.01); *A61K 45/06* (2013.01); *C07D 401/14* (2013.01); *C07D 403/04* (2013.01); *C07D 403/08* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 5,935,982 A | 8/1999 | Dykstra et al. | |
| 7,438,920 B1 | 10/2008 | Kim et al. | |
| 7,659,270 B2 | 2/2010 | Bachand et al. | |
| 7,906,655 B2 | 3/2011 | Belema et al. | |
| 8,147,818 B2 | 4/2012 | Bachand et al. | |
| 8,303,944 B2 | 11/2012 | Bachand et al. | |
| 8,420,686 B2 | 4/2013 | Or et al. | |
| 8,426,458 B2 | 4/2013 | Or et al. | |
| 2006/0019974 A1 | 1/2006 | Mederski et al. | |
| 2006/0258682 A1 | 11/2006 | Liao et al. | |
| 2007/0032497 A1 | 2/2007 | Hashimoto et al. | |
| 2007/0049593 A1 | 3/2007 | Oka et al. | |
| 2007/0185175 A1 | 8/2007 | Liu et al. | |
| 2008/0044379 A1 | 2/2008 | Bachand et al. | |
| 2008/0200423 A1 | 8/2008 | Cook et al. | |
| 2009/0202478 A1 | 8/2009 | Bachand et al. | |
| 2009/0202483 A1 | 8/2009 | Bachand et al. | |
| 2010/0055071 A1 | 3/2010 | Leivers et al. | |
| 2010/0087382 A1 | 4/2010 | Bailey et al. | |
| 2010/0215616 A1 | 8/2010 | Romine et al. | |
| 2010/0233122 A1 | 9/2010 | Qiu et al. | |
| 2010/0316607 A1 | 12/2010 | Or et al. | |
| 2011/0223134 A1 | 9/2011 | Nair et al. | |
| 2012/0083483 A1 | 4/2012 | Coburn et al. | |
| 2012/0251491 A1 | 10/2012 | Rosenblum et al. | |
| 2012/0258078 A1 | 10/2012 | Rosenblum et al. | |
| 2012/0276047 A1 | 11/2012 | Rosenblum et al. | |
| 2013/0156731 A1 | 6/2013 | Chen et al. | |

FOREIGN PATENT DOCUMENTS

| | | |
|---|---|---|
| WO | 0020400 | 4/2000 |
| WO | 2008133753 | 11/2008 |
| WO | 2008144380 | 11/2008 |
| WO | 2010065681 | 6/2010 |
| WO | 2010096777 | 8/2010 |
| WO | 2010138790 | 12/2010 |
| WO | 2011075439 | 6/2011 |

OTHER PUBLICATIONS

Wachowius, et al., "Synthesis and DNA Duplex Recognition of a Triplex-Forming Oligonucleotide With an Ureide-Substitued 4-Phenylimidazole Nucleoside", Tetrahedron Letters, 2008, vol. 49, pp. 7264-7267.

Pujals, et al., "Replacement of a Proline With a Silaproline Causes a 20-Fold Increase in the Cellular Uptake of a Pro-Rich Peptide", J. Am. Chem. Soc., 2006, vol. 128, pp. 8479-8483.

Koch and Narjes, "Recent Progress in the Development of Inhibitors of the Hepatitis C Virus RNA-Dependent RNA Polymerase", Current Topics in Medicinal Chemistry, 2007, vol. 7, pp. 1302-1329.

*Primary Examiner* — Jeffrey S Lundgren
*Assistant Examiner* — Stephanie Springer
(74) *Attorney, Agent, or Firm* — Jeffrey P. Bergman; Catherine D. Fitch

(57) ABSTRACT

The present invention relates to novel Fused Tricyclic Compounds, compositions comprising at least one Fused Tricyclic Compound, and methods of using Fused Tricyclic Compounds for treating or preventing a viral infection or a virus-related disorder in a patient.

7 Claims, No Drawings

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer
```

```
<400> SEQUENCE: 1
atggacaggc gccctga                                              17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                           20

<210> SEQ ID NO 3
<211> LENGTH: 17
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: FAM labeled

<400> SEQUENCE: 3
cacgccatgc gctgcgg                                              17
```

FUSED TRICYCLIC COMPOUNDS AND METHODS OF USE THEREOF FOR THE TREATMENT OF VIRAL DISEASES

CROSS-REFERENCE TO RELATED APPLICATIONS

This application is a continuation of U.S. Application Ser. No. 13/518,336, filed Jun. 21, 2012 and copending, which is the national stage application under 35 U.S.C. 371 of International Patent Application No. PCT/US2010/061205, filed Dec. 20, 2010, which claims priority to US Provisional Application No. 61/289,204, filed Dec. 22, 2009. Each of the aforementioned PCT and priority applications is incorporated by reference in its entirety.

REFERENCE TO SEQUENCE LISTING SUBMITTED ELECTRONICALLY

The sequence listing of the present application is being submitted electronically via EFS-Web as an ASCII formatted sequence listing with a file name "IN2009-7110-US-CNT-SEQ.TXT," creation date of Sep. 26, 2016 and a size of 1 KB. This sequence listing submitted via EFS-Web is part of the specification and is herein incorporated by reference in its entirety.

FIELD OF THE INVENTION

The present invention relates to novel Fused Tricyclic Compounds, compositions comprising at least one Fused Tricyclic Compound, and methods of using Fused Tricyclic Compounds for treating or preventing a viral infection or a virus-related disorder in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see, International Publication No. WO 89/04669 and European Patent-Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

It is well-established that persistent infection of HCV is related to chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Recent attention has been focused toward the identification of inhibitors of HCV NS5A. HCV NS5A is a 447 amino acid phosphoprotein which lacks a defined enzymatic function. It runs as 56kd and 58kd bands on gels depending on phosphorylation state (Tanji, et a. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula (I):

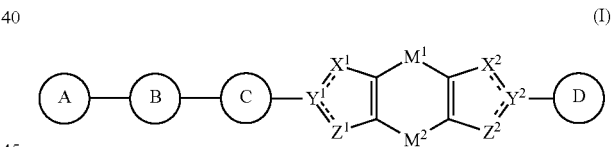

and pharmaceutically acceptable salts thereof, wherein each dotted line represents an optional and additional bond, such that only one optional and additional bond can be attached to each of $Y^1$ and $Y^2$, and wherein:

A is -alkylene-$N(R^7)(R^{11})$ or heterocycloalkyl, wherein said heterocycloalkyl group can be optionally and independently substituted on one or more ring nitrogen atoms with $R^4$, and on one or more ring carbon atoms with $R^{12}$, and wherein said heterocycloalkyl group can be optionally fused to a cycloalkyl group or an aryl group;

B is monocyclic heteroarylene or bicyclic heteroarylene, wherein said monocyclic heteroarylene group or said bicyclic heteroarylene group can be optionally and independently substituted on one or more ring nitrogen atoms with $R^6$, and on one or more ring carbon atoms with $R^{12}$;

C is a bond, monocyclic heteroarylene or bicyclic heteroarylene, wherein said monocyclic heteroarylene group or said bicyclic heteroarylene group can be can be optionally and independently substituted on one or more ring nitrogen atoms with $R^6$ and on one or more ring carbon atoms with $R^{12}$;

D is -alkylene-N($R^7$)($R^{11}$) or heterocycloalkyl, wherein said heterocycloalkyl group can be can be optionally and independently substituted on one or more ring nitrogen atoms with $R^4$, and on one or more ring carbon atoms with $R^{12}$, and wherein a heterocycloalkyl can be optionally fused to a cycloalkyl group or an aryl group;

$M^1$ is a bond, —[C($R^7$)$_2$]$_q$—, —[C($R^7$)$_2$]$_m$—C($R^2$)=C($R^2$)—[C($R^7$)$_2$]$_m$—, —C($R^7$)=N—, —N=C($R^7$)—, —[C($R^7$)$_2$]$_m$—O—[C($R^7$)$_2$]$_m$, —O—[C($R^7$)$_2$]$_q$—O—, —[C($R^7$)$_2$]$_m$—N($R^6$)—[C($R^7$)$_2$]$_m$—, —S—, —[C($R^7$)$_2$]$_m$—S(O)$_m$—[C($R^7$)$_2$]$_m$—, —[C($R^7$)$_2$]$_m$—OC(O)N($R^6$)—[C($R^7$)$_2$]$_m$—, —[C($R^7$)$_2$]$_m$—N($R^6$)C(O)N($R^6$)—[C($R^7$)$_2$]$_m$—, —[C($R^7$)$_2$]$_m$—S(O)$_2$N($R^6$)—[C($R^7$)$_2$]$_m$— or —[C($R^7$)$_2$]$_m$—N($R^6$)S(O)$_2$N($R^6$)—[C($R^7$)$_2$]$_m$—;

$M^2$ is a bond, —[C($R^7$)$_2$]$_q$—, —[C($R^7$)$_2$]$_m$—C($R^2$)=C($R^2$)—[C($R^7$)$_2$]$_m$—, —C($R^7$)=N—, —N=C($R^7$)—, —[C($R^7$)$_2$]$_m$—O—[C($R^7$)$_2$]$_m$, —O—[C($R^7$)$_2$]$_q$—O—, —[C($R^7$)$_2$]$_m$—N(—$R^6$)—[C($R^7$)$_2$]$_m$—, —S—, —[C($R^7$)$_2$]$_m$—S(O)$_m$—[C($R^7$)$_2$]m—, —[C($R^7$)$_2$]m—OC(O)N($R^6$)—[C($R^7$)$_2$]$_m$—, —[C($R^7$)$_2$]$_m$—N($R^6$)C(O)N($R^6$)—[C($R^7$)$_2$]$_m$—, —[C($R^7$)$_2$]$_m$—S(O)$_2$N($R^6$)—[C($R^7$)$_2$]$_m$— or —[C($R^7$)$_2$]$_m$—N($R^6$)S(O)$_2$N($R^6$)—[C($R^7$)$_2$]$_m$—, such that at least one of $M^1$ and $M^2$ is other than a bond, and such that the central ring of formula (I) that contains $M^1$ and $M^2$ has from 5 to 10 total ring atoms, and wherein two vicinal $R^7$ groups of $M^1$ or $M^2$ together with the carbon atoms to which they are attached, can optionally join to form a 3- to 7-membered cycloalkyl group, a 3- to 7-membered heterocycloalkyl group, or a 5- to 6-membered heteroaryl group;

$X^1$ is a bond, —C($R^2$)=C($R^2$)—, —N=C($R^5$)—, —C($R^5$)=NC—, —C($R^5$)=N—, —O—, —N($R^6$)—, —S— or —S(O)$_2$— when the optional and additional bond to $X^1$ is not present, and $X^1$ is —C($R^5$)—, is —C($R^5$)(C($R^5$)=C($R^5$)—, —N—, —N—C($R^5$)=C($R^5$)—, —C($R^5$)N=C($R^5$)—, —C($R^5$)C($R^5$)=N—, —C($R^5$)O—, —C($R^5$)N($R^6$)—, —N—N($R^6$)—, —C($R^5$)S— or —C($R^5$)S(O)$_2$— when the optional and additional bond to $X^1$ is present, such that $X^1$ and $Z^1$ cannot each be a bond, and such that when $X^1$ is —C($R^5$)—, —N($R^6$)—, —N—, or —O—, then $Z^1$ is other than a bond;

$X^2$ is a bond, —C($R^2$)=C($R^2$)—, —N=C($R^5$)—, —C($R^5$)N=C—, —C($R^5$)=N—, —O—, —N($R^6$)—, —S— or —S(O)$_2$— when the optional and additional bond to $X^2$ is not present, and $X^2$ is —C($R^5$)—, is —C($R^5$)=(C($R^5$)C($R^5$)—, —N—, —C($R^5$)=C($R^5$)N—, —C($R^5$)=NC($R^5$)—, —N=C($R^5$)C($R^5$)—, —OC($R^5$)—, —N($R^6$)C($R^5$)—, —N($R^6$)—N—, —S—C($R^5$)— or —S(O)$_2$C($R^5$)— when the optional and additional bond to $X^2$ is present, such that $X^2$ and $Z^2$ cannot each be a bond, and such that when $X^2$ is —C($R^5$)— —N($R^6$)—, —N—, or —O—, then $Z^2$ is other than a bond;

$Y^1$ is —C—, when an optional and additional bond to $Y^1$ is present, and $Y^1$ is —CH— when an optional and additional bond to $Y^1$ is absent;

$Y^2$ is —C—, when an optional and additional bond to $Y^2$ is present, and $Y^2$ is —CH— when an optional and additional bond to $Y^2$ is absent;

$Z^1$ is a bond, —C($R^5$)=C($R^5$)—, —N=C($R^5$)—, —C($R^5$)=NC—, —C($R^5$)=N—, —O—, —N($R^6$)—, —S— or —S(O)$_2$— when the optional and additional bond to $Z^1$ is not present, and $Z^1$ is —C($R^5$)—, —C($R^5$)(CH($R^5$))$_m$—, —N—, —NCH($R^5$)CH($R^5$)—, —C($R^5$)NHCH($R^5$)—, —C($R^5$)CH($R^5$)NH—, —C($R^5$)O—, —C($R^5$)N($R^6$)—, —N—N($R^6$)—, —C($R^5$)S— or —C($R^5$)S(O)$_2$— when the optional and additional bond to $Z^1$ is present, such that the ring in formula (I) containing $X^1$, $Y^1$ and $Z^1$ has 5 or 6 total ring atoms;

$Z^2$ is a bond, —C($R^5$)=C($R^5$)—, —N=C($R^5$)—, —C($R^5$)N=C—, —C($R^5$)=N—, —O—, —N($R^6$)—, —S— or —S(O)$_2$— when the optional and additional bond to $Z^2$ is not present, and $Z^2$ is —C($R^5$)—, —(CH($R^5$))$_m$C($R^5$)—, —N—, —CH($R^5$)CH($R^5$)N—, —CH($R^5$)NHC($R^5$)—, —NHCH($R^5$)C($R^5$)—, —OC($R^5$)—, —N($R^6$)C($R^5$)—, —N($R^6$)—N—, —S—C($R^5$)— or —S(O)$_2$C($R^5$)— when the optional and additional bond to $Z^2$ is present, such that the ring in formula (I) containing $X^2$, $Y^2$ and $Z^2$ has 5 or 6 total ring atoms;

each occurrence of $R^1$ is independently $C_1$-$C_6$ alkyl, $C_1$-$C_6$ haloalkyl, aryl, 3 to 7 membered cycloalkyl, 4 to 7 membered heterocycloalkyl or heteroaryl, wherein said aryl group, said cycloalkyl group, said heterocycloalkyl group or said heteroaryl group can be optionally and independently substituted with up to three $R^2$ groups;

each occurrence of $R^2$ is independently $C_1$-$C_6$ alkyl, aryl, 3 to 7 membered cycloalkyl, 4 to 7 membered heterocycloalkyl, heteroaryl, halo, $C_1$-$C_6$ haloalkyl, —CN, —OR$^3$, —N($R^3$)$_2$, —C(O)$R^{10}$, —C(O)OR$^3$, —C(O)N($R^3$)$_2$, —NHC(O)$R^{10}$, —NHC(O)NHR$^3$, —NHC(O)OR$^3$, —OC(O)$R^{10}$, —SR$^3$ or —S(O)$_2$$R^{10}$;

each occurrence of $R^3$ is independently H, $C_1$-$C_6$ alkyl, $C_1$-$C_6$ haloalkyl, aryl, 3 to 7 membered cycloalkyl, 4 to 7 membered heterocycloalkyl or heteroaryl, wherein said aryl group, said cycloalkyl group, said heterocycloalkyl group or said heteroaryl group can be optionally and independently substituted with up to three groups independently selected from hydroxy, halo, alkyl, aminoalkyl, and haloalkyl.

each occurrence of $R^4$ is independently H, —C(O)—[C($R^7$)$_2$]$_q$N($R^6$)$_2$, —C(O)—[C($R^7$)$_2$]$_q$N($R^6$)C(O)—$R^1$, —C(O)—[C($R^7$)$_2$]$_q$N($R^6$)C(O)O—$R^1$, —C(O)—[C($R^7$)$_2$]$_q$C(O)O—$R^1$, —C(O)[C($R^7$)$_2$]$_q$N($R^6$)SO$_2$—$R^1$ or -alkylene-N($R^6$)—[C($R^7$)$_2$]$_q$—N($R^6$)—C(O)O—$R^1$;

each occurrence of $R^5$ is independently H, $C_1$-$C_6$ alkyl, 3 to 7-membered cycloalkyl, aryl or heteroaryl;

each occurrence of $R^6$ is independently H, $C_1$-$C_6$alkyl, 3 to 7-membered cycloalkyl, 4 to 7-membered heterocycloalkyl, aryl, or heteroaryl, wherein said aryl group, said cycloalkyl group, said heterocycloalkyl group or said heteroaryl group can be optionally and independently substituted with up to two $R^8$ groups, and wherein two $R^6$ groups that are attached to a common nitrogen atom, together with the nitrogen atom to which they are attached, can optionally join to form a 4 to 7-membered heterocycloalkyl group;

each occurrence of $R^7$ is independently H, $C_1$-$C_6$ alkyl, 3 to 7-membered cycloalkyl, 4 to 7-membered-heterocycloalkyl, aryl, heteroaryl, wherein said aryl group, said cycloalkyl group, said heterocycloalkyl group or said heteroaryl group can be optionally and independently substituted with up to 3 substituents, which can be the same or different, and are selected from $C_1$-$C_6$ alkyl, halo, —$C_1$-$C_6$ haloalkyl, $C_1$-$C_6$ hydroxyalkyl, —OH, —C(O)NH—($C_1$-$C_6$ alkyl), —C(O)N($C_1$-$C_6$ alkyl)$_2$, —O—($C_1$-$C_6$ alkyl), —NH$_2$, —NH($C_1$-$C_6$alkyl), —N($C_1$-$C_6$ alkyl)$_2$ and —NHC(O)—($C_1$-$C_6$ alkyl), and wherein two geminal $R^7$ groups, together with the common carbon-atom to which they are attached, can optionally join to form —C(O)—, —C(S)—, —C(=NR$^9$)—, —C(=NOR$^9$)—, a 3 to 7-membered cycloalkyl group or a 4 to 7-membered heterocycloalkyl group, such that no two adjacent —C($R^7$)$_2$— groups can join to form a —C(O)—C(O)—, —C(S)—C(S)—, —C(O)—C(S)— or —C(S)—C(O)— group;

each occurrence of $R^8$ is independently H or $C_1$-$C_6$ alkyl;

each occurrence of $R^9$ is independently H, $C_1$-$C_6$ alkyl, 3 to 7-membered cycloalkyl or 4 to 7-membered heterocycloalkyl;

each occurrence of $R^{10}$ is independently $C_1$-$C_6$ alkyl, $C_1$-$C_6$ haloalkyl, aryl, 3 to 7-membered cycloalkyl, 4 to 7-membered heterocycloalkyl or heteroaryl;

each occurrence of $R^{11}$ is independently —C(O)—[C$(R^7)_2]_q$N$(R^6)_2$, —C(O)—[C$(R^7)_2]_q$N$(R^6)$C(O)—$R^1$, —C(O)—[C$(R^7)_2]_q$N$(R^6)$C(O)O—$R^1$, —C(O)—[C$(R^7)_2]_q$C(O)O—$R^1$, —C(O)[C$(R^7)_2]_q$N$(R^6)$SO$_2$—$R^1$ or -alkylene-N$(R^6)$—[C$(R^7)_2]_q$—N$(R^6)$—C(O)O—$R^1$;

each occurrence of $R^{12}$ is H, $C_1$-$C_6$ alkyl, 3 to 7-membered cycloalkyl, 4 to 7-membered heterocycloalkyl, aryl, heteroaryl, halo, $C_1$-$C_6$ haloalkyl, —CN, —OR$^3$, —N$(R^3)_2$, —C(O)R$^{10}$, —C(O)OR$^3$, —C(O)N$(R^3)_2$, —NHC(O)R$^{10}$, —NHC(O)NHR$^3$, —NHC(O)OR$^3$, —OC(O)R$^{10}$, —SR$^3$ or —S(O)$_2$R$^{10}$; and wherein two $R^{12}$ groups together with the carbon atoms to which they are attached, can optionally join to form a 5 to 7-membered cycloalkyl or 4 to 7-membered heterocycloalkyl group;

each occurrence of m is independently an integer ranging from 0 to 2; and each occurrence of q is independently an integer ranging from 1 to 4.

The Compounds of Formula (I) (also referred to herein as the "Fused Tricyclic Compounds") and pharmaceutically acceptable salts thereof can be useful for treating or preventing a viral infection or a virus-related disorder in a patient.

The Fused Tricyclic Compounds or pharmaceutically acceptable salts thereof can also be useful for treating or preventing a viral infection or a virus-related-disorder in a patient.

Also provided by the invention are methods for treating or preventing a viral infection or a virus-related disorder in a patient, comprising administering to the patient an effective amount of at least one Fused Tricyclic Compound.

The present invention further provides pharmaceutical compositions comprising an effective amount of at least one Fused Tricyclic Compound or a pharmaceutically acceptable salt thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Fused Tricyclic Compounds, pharmaceutical compositions comprising at least one Fused Tricyclic Compound, and methods of using the Fused Tricyclic Compounds for treating or preventing a viral infection or a virus-related disorder in a patient.

Definitions and Abbreviations

The terms used herein have their ordinary meaning and the meaning of such terms is independent at each occurrence thereof. That notwithstanding and except where stated otherwise, the following definitions apply-throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . . .

As used herein, and throughout this disclosure, the following terms, unless otherwise indicated, shall be understood to have the following meanings:

A "patient" is a human or non-human mammal. In one embodiment, a patient is a human, In another embodiment, a patient is a chimpanzee.

The term "effective amount" as used herein, refers to an amount of Fused Tricyclic Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, iso-hexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched. The term "$C_1$-$C_6$ alkyl" refers to an alkyl group having from 1 to 6 carbon atoms.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl; propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C (O)-aryl, —O—C(O)-cycloalkyl, —C(O)OH and —C(O)O-alkyl. In one embodiment, an alkenyl group is unsubstituted. The term "C$_2$-C$_6$ alkenyl" refers to an alkenyl group having from 2 to 6 carbon atoms.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkynyl group is unsubstituted. The term "C$_2$-C$_6$ alkynyl" refers to an alkynyl group having from 2 to 6 carbon atoms.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is unsubstituted. In another embodiment, an aryl group is phenyl.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

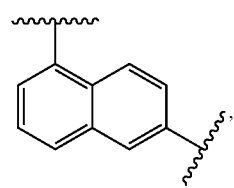 [SMILES: *c1ccc2c(*)cccc2c1]

is understood to represent both:

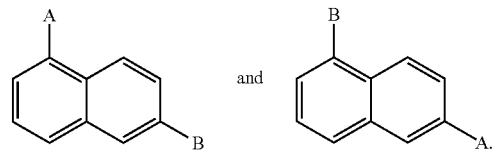

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

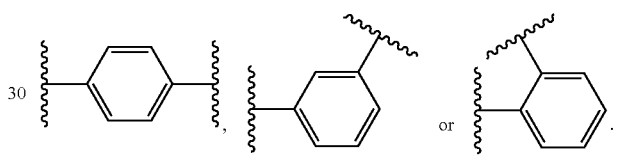

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

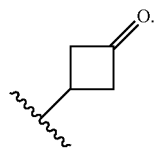 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different; and are as defined herein below. A ring carbon atom of a cycloalkyl group may be functionalized as a carbonyl group. In one embodiment, a cycloalkenyl group is unsubstituted. In another embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms.

"Halo" means —F, —Cl, —Br or —I. In one: embodiment, halo refers to —F, —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo [2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetraltydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl. In another embodiment, a heteroaryl group comprises a 5 or 6-membered heteroaryl group fused to a benzene ring. The term "3 to 7-membered cycloalkyl" refers to a cycloalkyl group having from 3 to 8 ring carbon atoms.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothicnylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

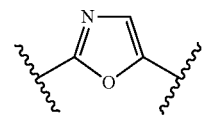 [SMILES: *c1cnc(*)o1]

is understood to represent both:

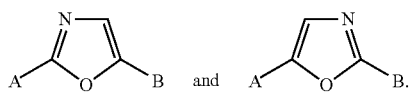

In one embodiment, a heteroarylene group is unsubstituted. In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. A heterocycloalkyl group can be joined via a ring carbon or ring nitrogen atom. In one embodiment, a heterocycloalkyl group has from about 3 to about 7 ring atoms. In another embodiment, a heterocycloalkyl group has 5 or 6 ring atoms. In another embodiment, a heterocycloalkyl group is monocyclic. In still another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone and the like, and all isomers thereof. A ring carbon atom of a heterocycloalkyl group may be functionalized as a carbonyl group. An illustrative example of such a heterocycloalkyl group is pyrrolidonyl:

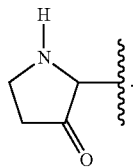 [SMILES: *C1NCCC1=O]

In one embodiment, a heterocycloalkyl group is unsubstituted. In another embodiment, a heterocycloalkyl group is a 5-membered heterocycloalkyl. In another embodiment, a heterocycloalkyl group is a 6-membered heterocycloalkyl. The term "3 to 7-membered cycloalkyl" refers to a heterocycloalkyl group having from 3 to 7 ring atoms.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazoly, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. In one embodiment, a heterocycloalkenyl group is unsubstituted. In another embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, hydroxy, hydroxyalkyl, haloalkyl, —O-alkyl-, —O—haloalkyl, -alkylene-O-alkyl, —O-aryl, aralkoxy, acyl, aroyl, halo, nitro; cyano, —SF$_5$, carboxy, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, and Y$_1$Y$_2$NS(O)$_2$—, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

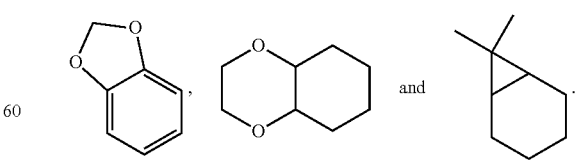

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g., from a reaction mixture), or natural source or combination thereof. Thus, the tern"purified", "in purified form" or "in isolated and purified form" for a compound refers to the physical state of the compound after being obtained from a purification process or processes described-herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987>14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tricyclic Compound or a pharmaceutically acceptable salt, hydrate or solvate of the compound. The transformation may occur by various mechanisms (e.g., by metabolic or chemical processes), such as, for example, through hydrolysis in blood.

For example, if a Fused Tricyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylamino-ethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Fused Tricyclic Compound contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O ($C_1$-$C_6$)alkyl)$_2$ or glycosyl (the radical resulting from the removal of a hydroxyl group of the hemiacetal form of a carbohydrate), and the like.

If a Fused Tricyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural α-aminoacyl, —C(OH)C(O)OY$^1$ wherein Y$^1$ is H, ($C_1$-$C_6$)alkyl or benzyi, —C(OY$^2$)Y$^3$ wherein Y$^2$ is ($C_1$-$C_4$) alkyl and Y$^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoaikyl; —C(Y$^4$)Y$^5$ wherein Y$^4$ is H or methyl and Y$^5$ is mono-N— or di-N, N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl,-sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or —O—$C_{1-4}$alkyl or amino); (2) sulfonate esters, such as alkyl-.or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tricyclic Compounds can form salts which are also within the scope of this invention. Reference to a Fused Tricyclic Compound herein is understood to include reference to salts thereof, unless otherwise indicated. The term- "salt(s)", as employed herein, denotes acidic salts formed with inorganic and/or organic acids, as well as basic salts formed with inorganic and/or organic bases. In addition, when a Fused Tricyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tricyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 6(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium-salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol, or Mosher's acid chloride), separating the diastereomers and converting (e.g., hydrolyzing) the individual diastereomers to the corresponding pure enantiomers. Sterochemically pure compounds may also be prepared by using-chiral starting materials or by employing salt resolution techniques. Also, some of the Fused Tricyclic Compounds may be atropisomers (e.g., substituted biaryls) and are considered as part of this invention. Enantiomers can also be directly separated using chiral chromatographic techniques.

It is also possible that the Fused Tricyclic Compounds may exist in different tautomeric forms, and all such forms are embraced within the scope of the invention. For example, all keto-enol and imine-enamine forms of the compounds are included in the invention. It should also be noted, that tautomeric forms such as, for example, the moieties:

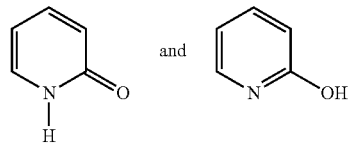 [SMILES: O=c1cccc[nH]1 ; Oc1ccccn1]

are considered equivalent in certain embodiments of this invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). If a Fused Tricyclic Compound incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found immature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled Fused Tricyclic Compounds (e.g., those labeled with $^3$H and $^{14}$C) are useful in compound and/or substrate tissue distribution assays. In one embodiment, tritiated (i.e., $^3$H) and carbon-14 (i.e., $^{14}$C) isotopes are employed for their ease of preparation and detectability. In another embodiment, substitution with heavier isotopes such as deuterium (i.e., $^2$H) may afford certain therapeutic advantages resulting from greater metabolic stability (e.g., increased in vivo half-life or reduced dosage requirements). In one embodiment, a Compound of Formula (I) has one or more of its hydrogen atoms replaced with a deuterium atom.

Isotopically labelled compounds of Formula (I) can generally be prepared by following procedures analogous to those disclosed in the Schemes and/or in the Examples herein below, by substituting an appropriate isotopically labelled reagent for a non-isotopically labelled reagent.

Polymorphic forms of the Fused Tricyclic Compounds, and of the salts, solvates, hydrates, esters- and prodrugs of the Fused Tricyclic Compounds, are intended to be included in the present invention.

The following abbreviations are used below and have the following meanings: Ac is acyl; AcOH is acetic acid; BOC or Boc is tert-butyloxycarbonyl; Boc-Pro-OH is Boc protected proline; L-Boc-Val-OH is Boc protected L-valine; dba is dibenzylideneacetone; DME is dimethoxyethane; DMF is N,N-dimethylformamide; dppf is diphenylphosphinoferrocene; DMSO is dimethylsulfoxide; EtOAc is ethyl acetate; HATU is is O-(7-azabenzotriazol-1-yl)-N,N,N',N'-tetramethyluronium hexafluorophosphate; HPLC is high performance liquid chromatography; HRMS is high resolution mass spectrometry; KOAc is potassium acetate; LCMS is liquid chromatography/mass spectrometry; LRMS is low resolution mass spectrometry; MeOH is methanol; MTBE is NH$_4$OAc is ammonium acetate; Pd(PPh$_3$)$_4$ is tetrakis(triphenylphosphine)palladium(0); TFA is trifluoroacetic acid; THF is tetrahydrofuran; TLC is thin-layer chromatography and XPhos is 2-dicyclohexylphosphino-2',4',6'-triisopropylbiphenyl.

The Compounds of Formula (I)

The present invention provides Fused Tricyclic Compounds of Formula (I):

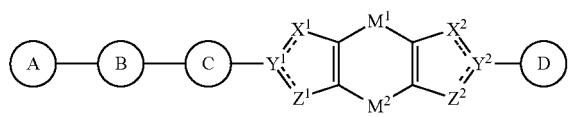

(I)

and pharmaceutically acceptable salts thereof, wherein A, B, C, D, M$^1$, M$^2$, X$^1$, X$^2$, Y$^1$, Y$^2$, Z$^1$ and Z$^2$ are defined above for the Compounds of Formula (I).

In one embodiment, A is -alkylene-N(R$^7$)(R$^{11}$).

In another embodiment, A is a 4 to 7-membered heterocycloalkyl.

In still another embodiment, A is selected from

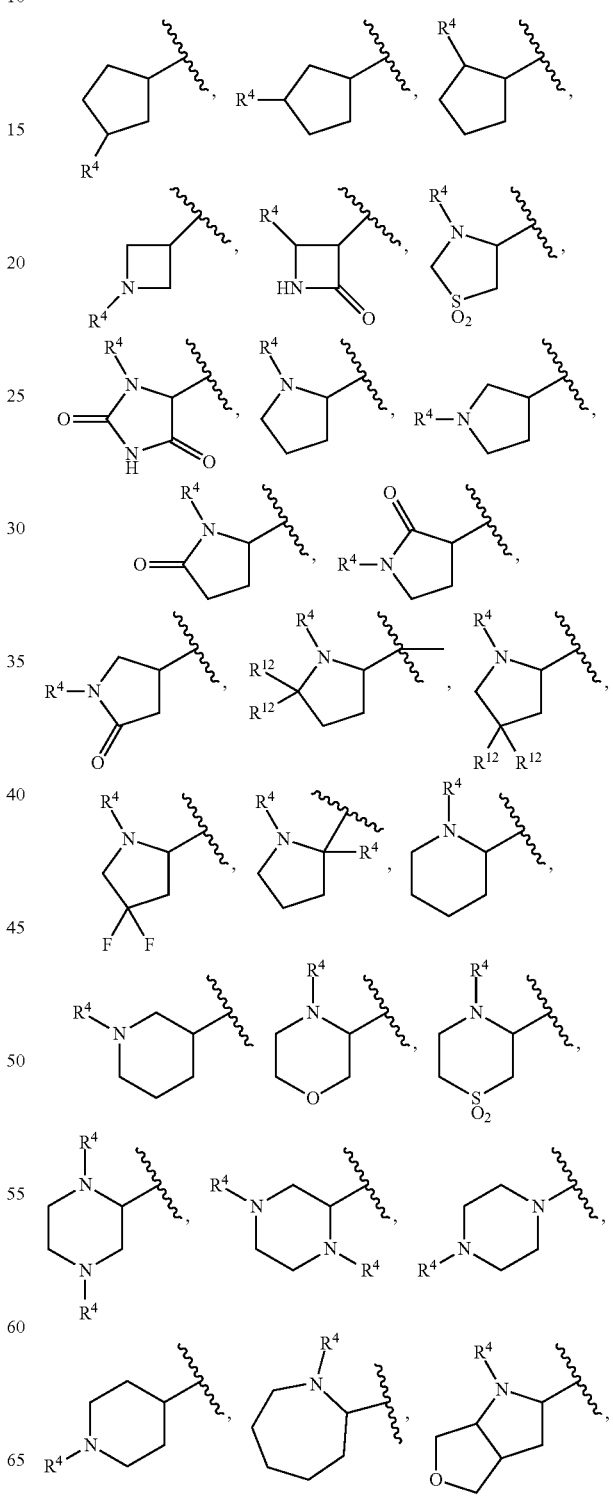

-continued
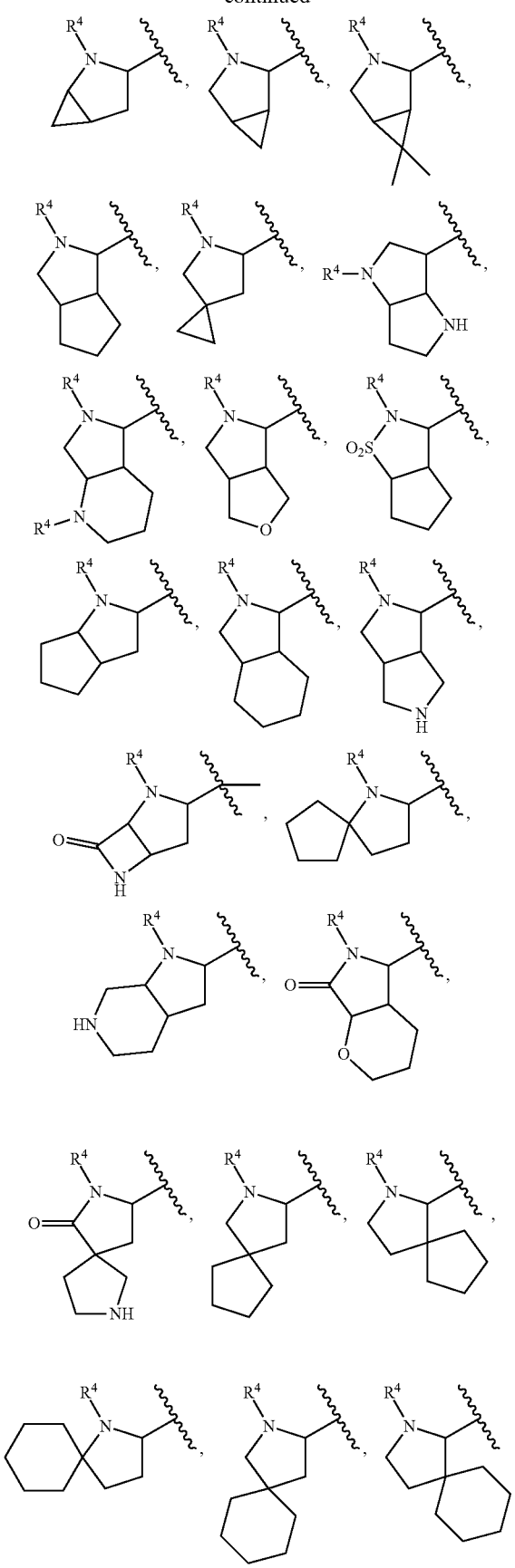
-continued
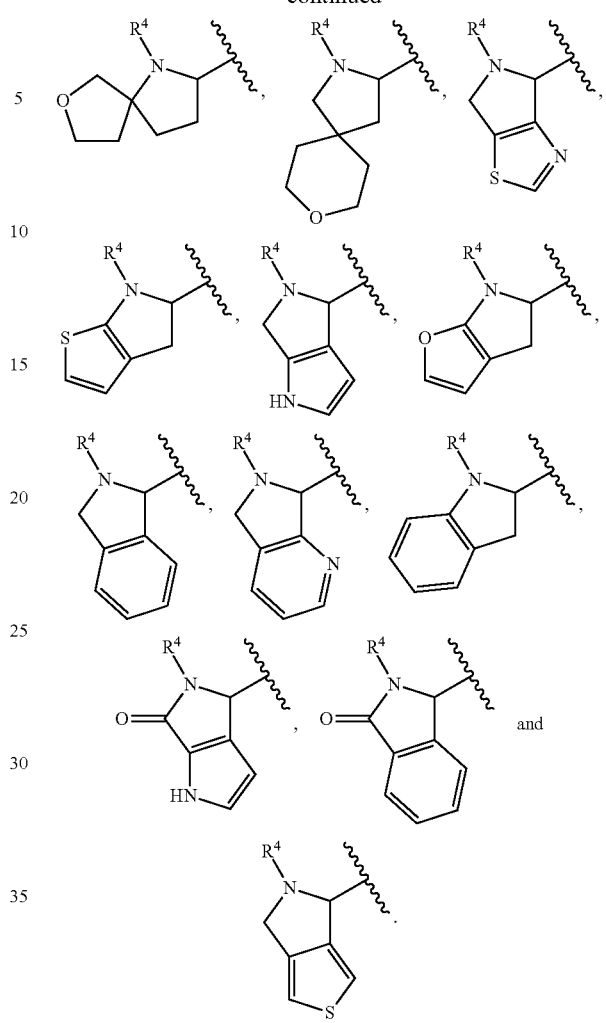
In another embodiment, A is selected from:
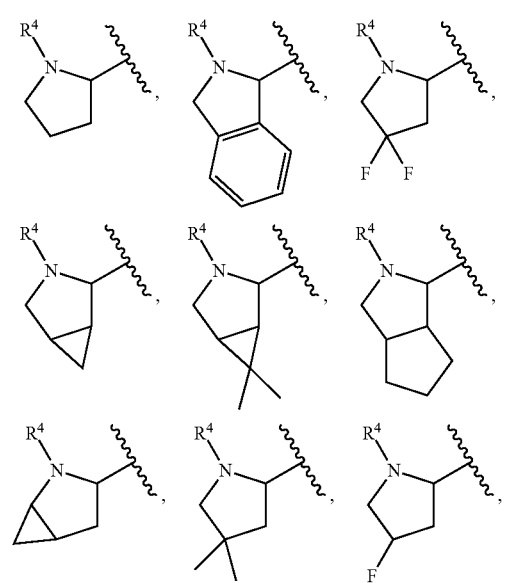

-continued

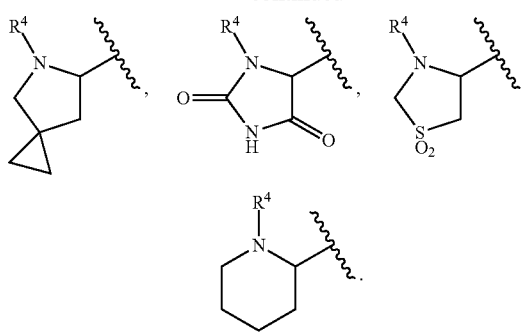

In another embodiment, A is selected from:

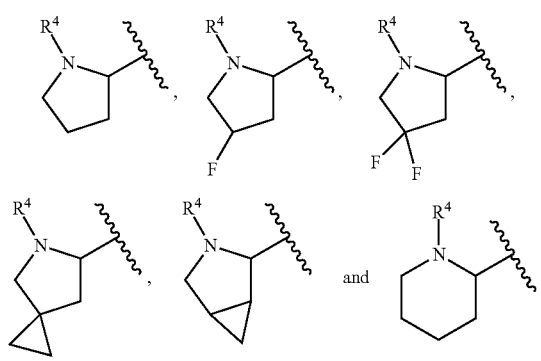

In yet another embodiment, A is selected from:

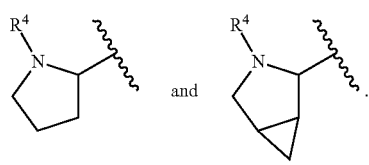

In another embodiment, A is

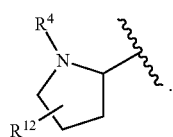

In another embodiment, A is:

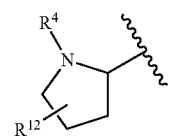

and R⁴ is —C(O)—[CH(R⁷)]$_q$N(R⁶)C(O)O—R¹.

In another embodiment, A is:

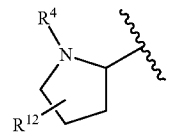

and R⁴ is:

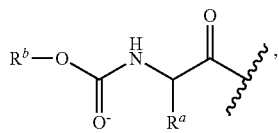

wherein $R^a$ is H, alkyl haloalkyl, cycloalkyl or aryl, and $R^b$ is alkyl.

In another embodiment, A is:

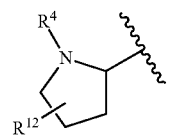

and R⁴ is:

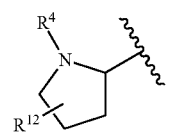

wherein $R^a$ is H, methyl, ethyl, propyl, isopropyl, t-butyl, cyclopropyl, —CH₂CH₂CF₃ or phenyl.

In another embodiment, A is:

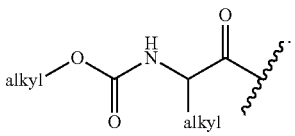

and R⁴ is:

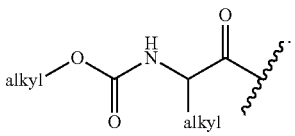

In yet another embodiment, A is:

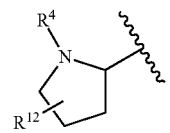

and $R^4$ is

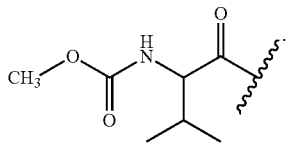 [SMILES: *C(=O)C(NC(=O)OC)C(C)C]

In another embodiment, A is -alkylene-N(cycloalkyl)-C(O)—CH(alkyl)-NHC(O)O-alkyl.

In another embodiment, A is -alkylene-N(cyclohexyl)-C(O)—CH(isopropyl)-NHC(O)O-methyl.

In a further embodiment, A is -alkylene-N(aryl)-C(O)—CH(alkyl)-NHC(O)O-alkyl.

In one embodiment, A is —C($R^{12}$)N($R^7$)($R^{11}$).

In another embodiment, A is -alkylene-N(cycloalkyl)-C(O)—CH(alkyl)-NHC(O)O— alkyl, -alkylene-N(cycloalkyl)-C(O)—CH(cycloalkyl)-NHC(O)O-alkyl, -alkylene-N(cycloalkyl)-C(O)—CH(aryl)-NHC(O)O-alkyl or -alkylene-N(cycloalkyl)-C(O)—CH(heteroaryl)-NHC(O)O-alkyl.

In one embodiment, B is a 6-membered monocyclic heteroarylene.

In another embodiment, B is a 5-membered monocyclic heteroarylene.

In another embodiment, B is a bicyclic heteroarylene.

In still another embodiment B is:

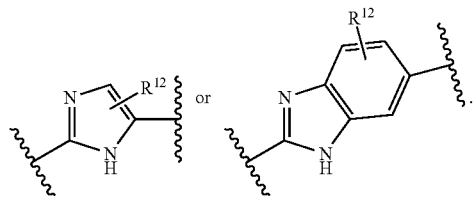

In one embodiment, C is a bond.

In another embodiment, C is a 6-membered monocyclic heteroarylene.

In another embodiment, C is a 5-membered monocyclic heteroarylene.

In still another embodiment, C is a bicyclic heteroarylene.

In another embodiment, C is:

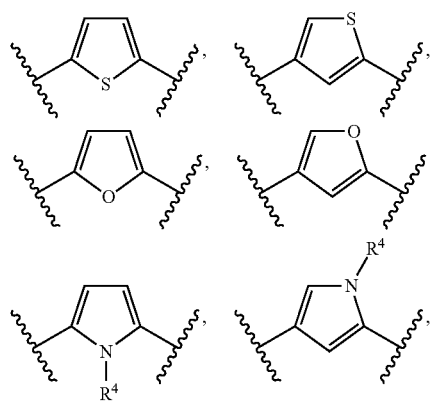

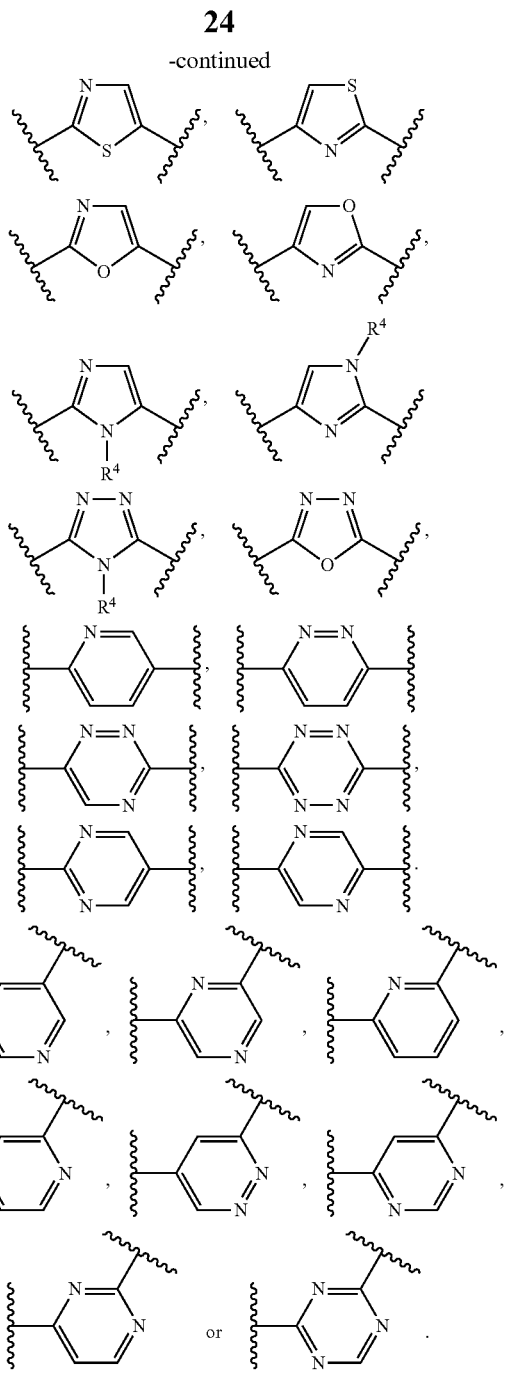

In another embodiment, C is a bond,

-continued
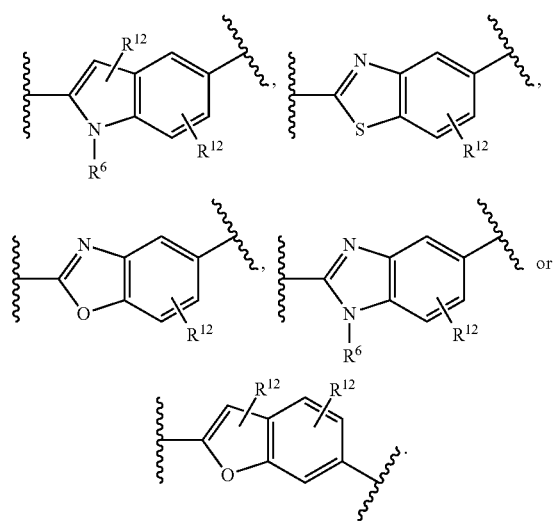
In another embodiment, C is:
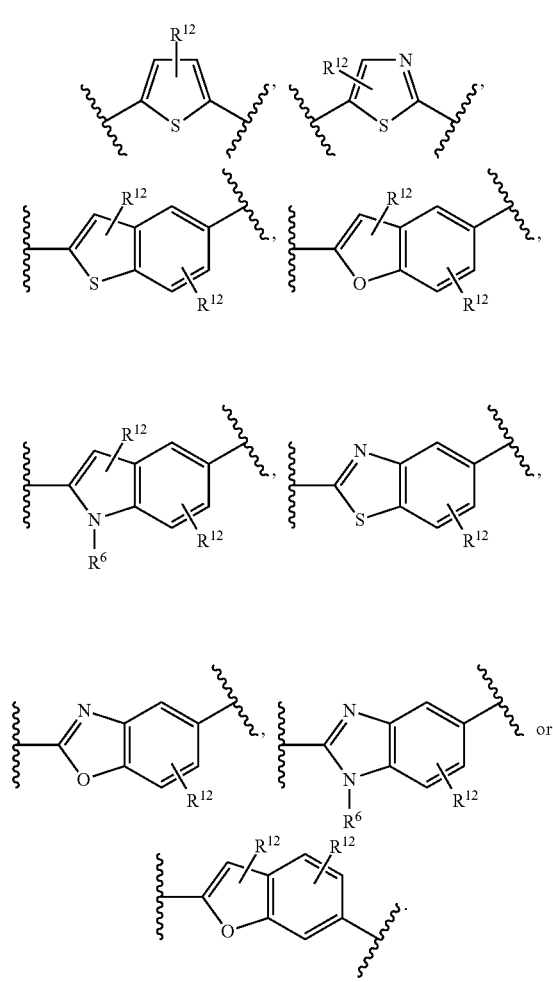
In one embodiment, D is -alkylene-N(R$^{11}$)(R$^{13}$).
In another embodiment, D is a 4 to 7-membered heterocycloalkyl.
In still another embodiment, D is selected from
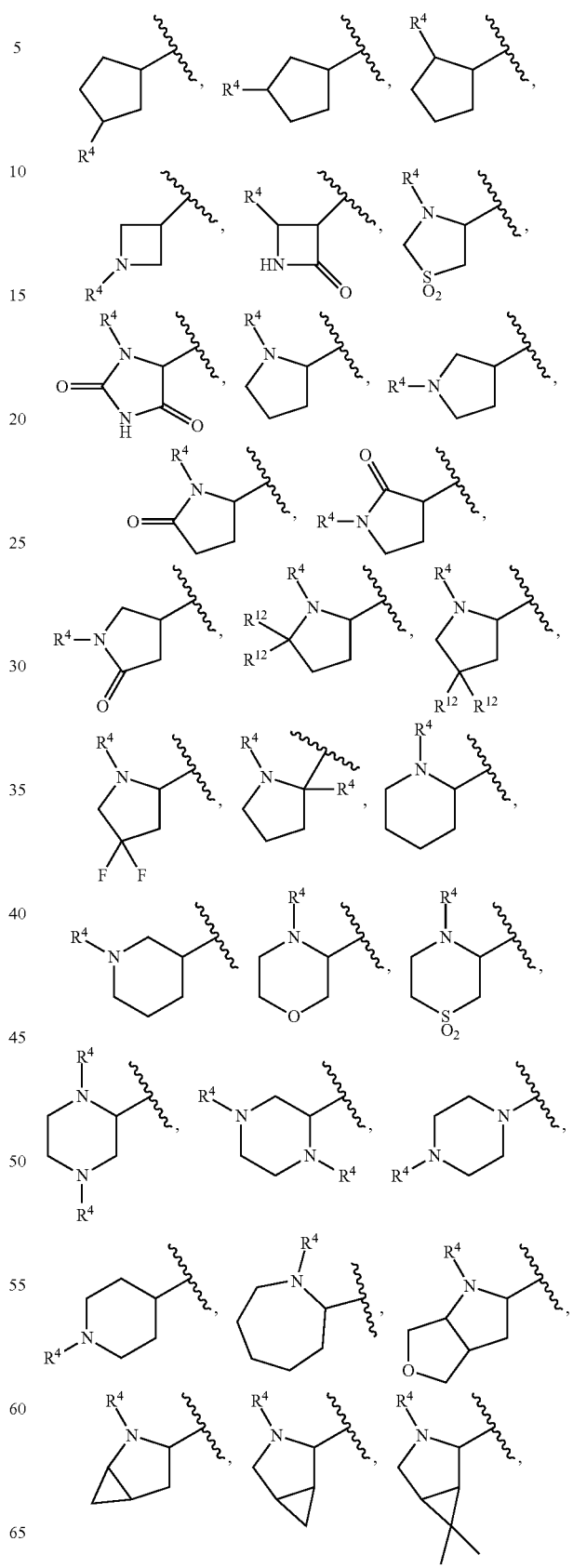

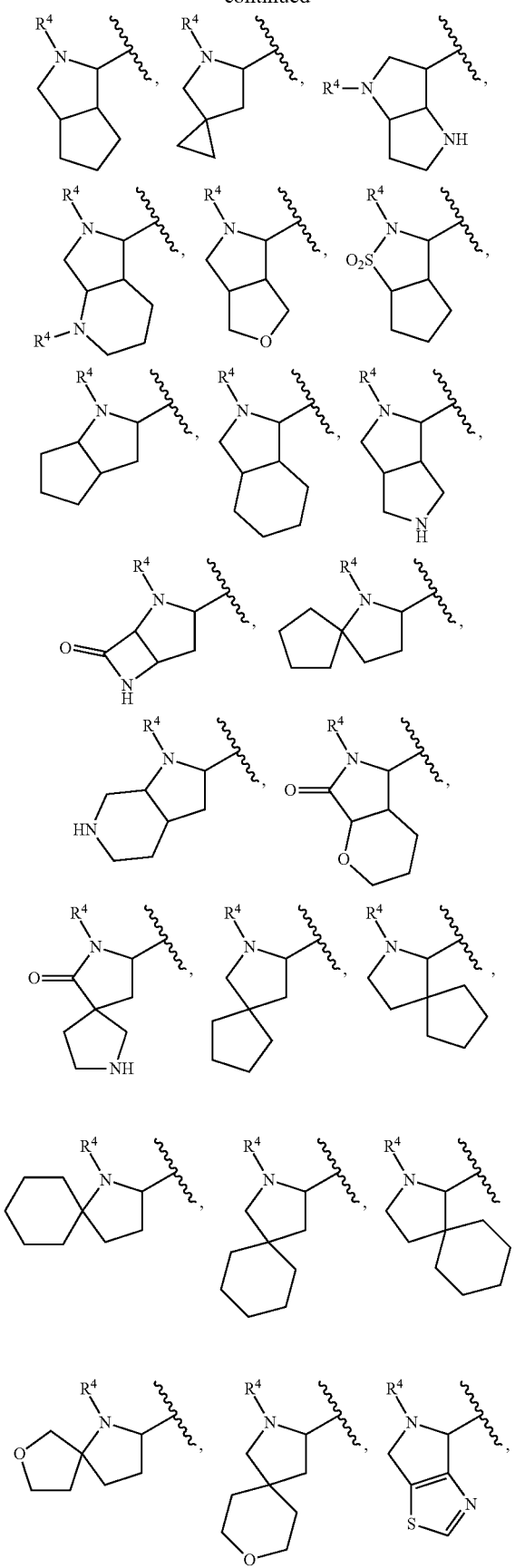
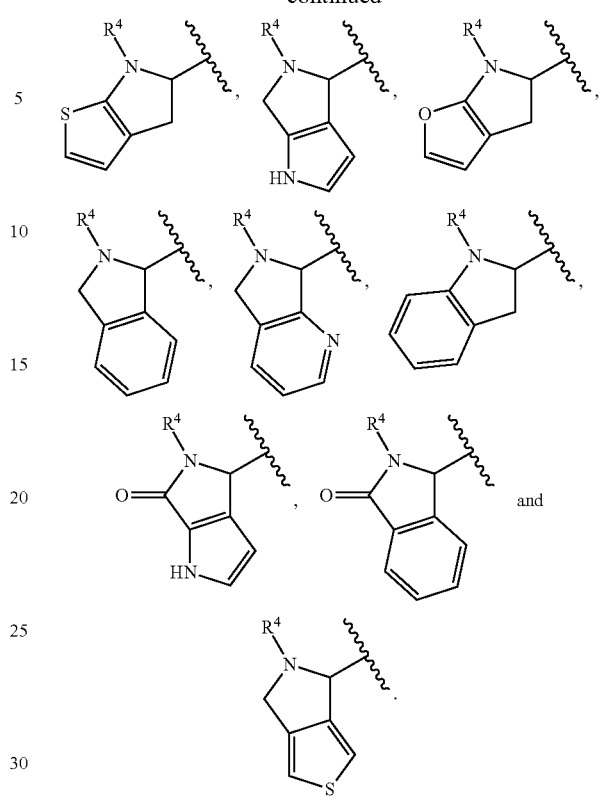
In yet another embodiment, D is selected from:
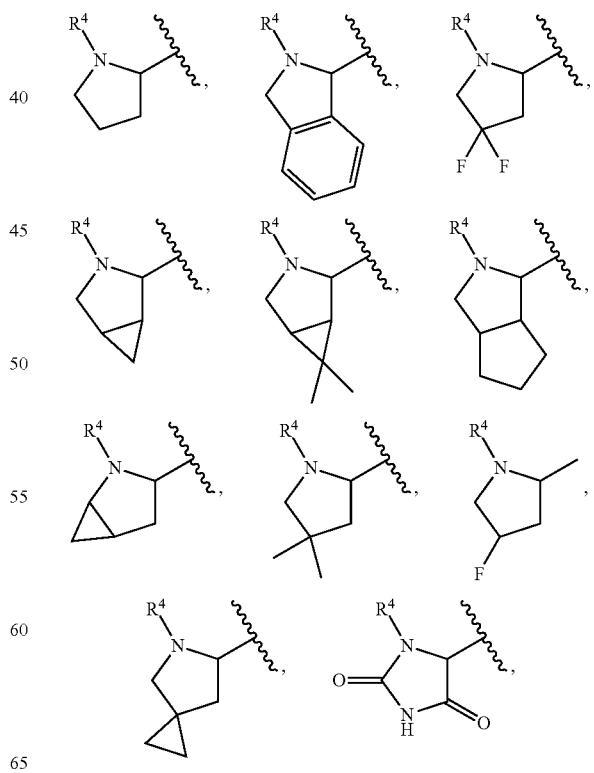

-continued

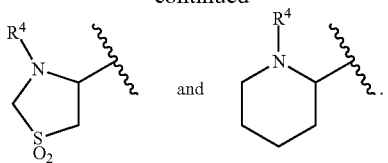

In another embodiment, D is selected from:

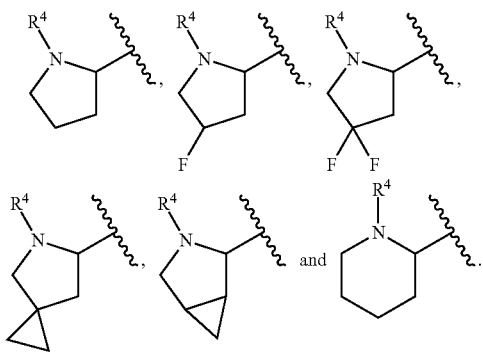

In yet another embodiment, D is selected from:

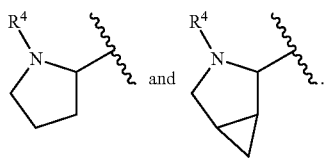

In another embodiment, D is

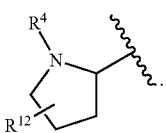

In another embodiment, D is:

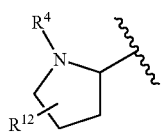

and $R^4$ is —C(O)—[CH($R^7$)]$_q$N($R^6$)C(O)O—$R^1$.

In still another embodiment, D is:

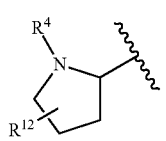

and $R^4$ is:

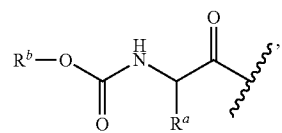

wherein $R^a$ is H, alkyl, haloalkyl, cycloalkyl or aryl, and $R^b$ is alkyl.

In another embodiment, D is:

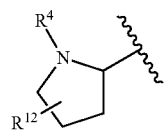

and $R^4$ is:

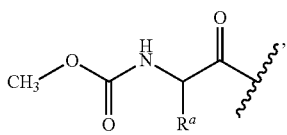

wherein $R^a$ is H, methyl, ethyl, propyl, isopropyl, t-butyl, cyclopropyl, —CH$_2$CH$_2$CF$_3$ or phenyl.

In another embodiment, D is:

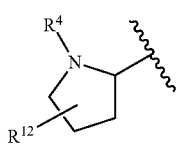

and $R^4$ is:

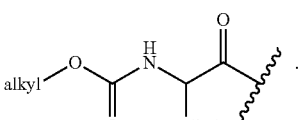

In yet another embodiment, D is:

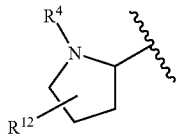

and $R^4$ is

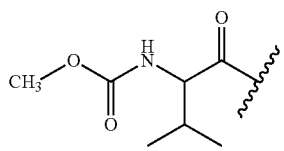

In another embodiment, D is -alkylene-N(cycloalkyl)-C(O)—CH(alkyl)-NHC(O)O-alkyl.

In another embodiment, D is -alkylene-N(cyclohexyl)-C(O)—CH(isopropyl)-NHC(O)O-methyl.

In a further embodiment, D is -alkylene-N(aryl)-C(O)—CH(alkyl)-NHC(O)O-alkyl.

In one embodiment, D is —C($R^{12}$)N($R^7$)($R^{11}$).

In another embodiment, D is -alkylene-N(cycloalkyl)-C(O)—CH(alkyl)-NHC(O)O-alkyl, -alkylene-N(cycloalkyl)-C(O)—CH(cycloalkyl)-NHC(O)O-alkyl, -alkylene-N(cycloalkyl)-C(O)—CH(aryl)-NHC(O)O-alkyl or -alkylene-N(cycloalkyl)-C(O)—CH(heteroaryl)-NHC(O)O-alkyl.

In one embodiment, A and D are each independently -alkylene-N($R^7$)($R^{11}$).

In another embodiment, A and D are each independently a 4 to 7-membered heterocycloalkyl.

In still another embodiment, A and D are each independently selected from

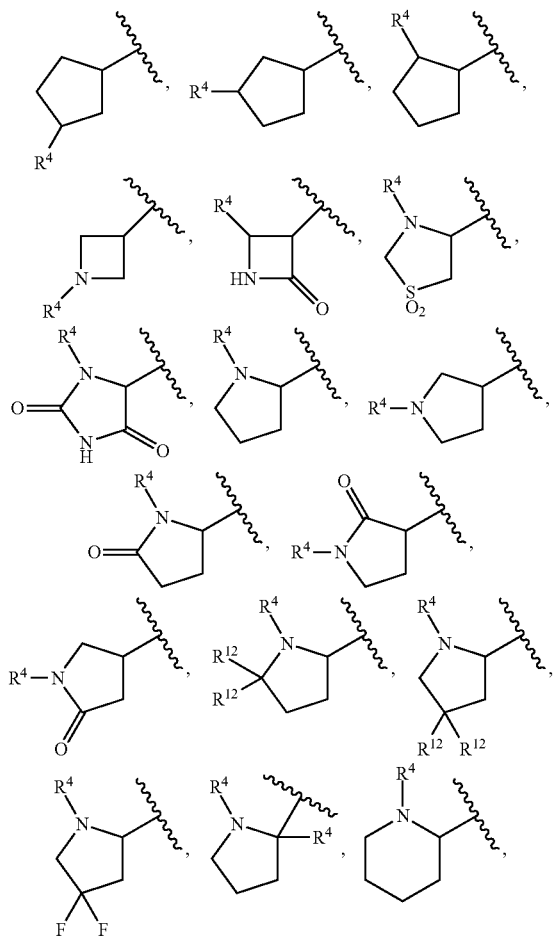

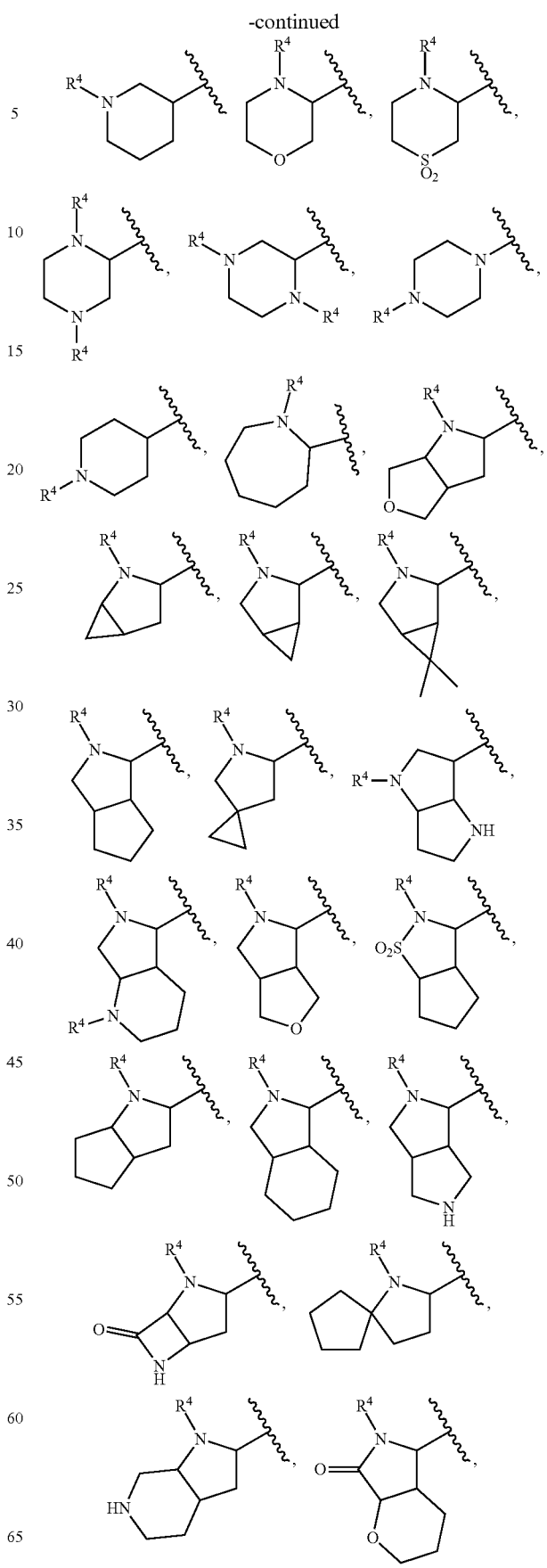

-continued
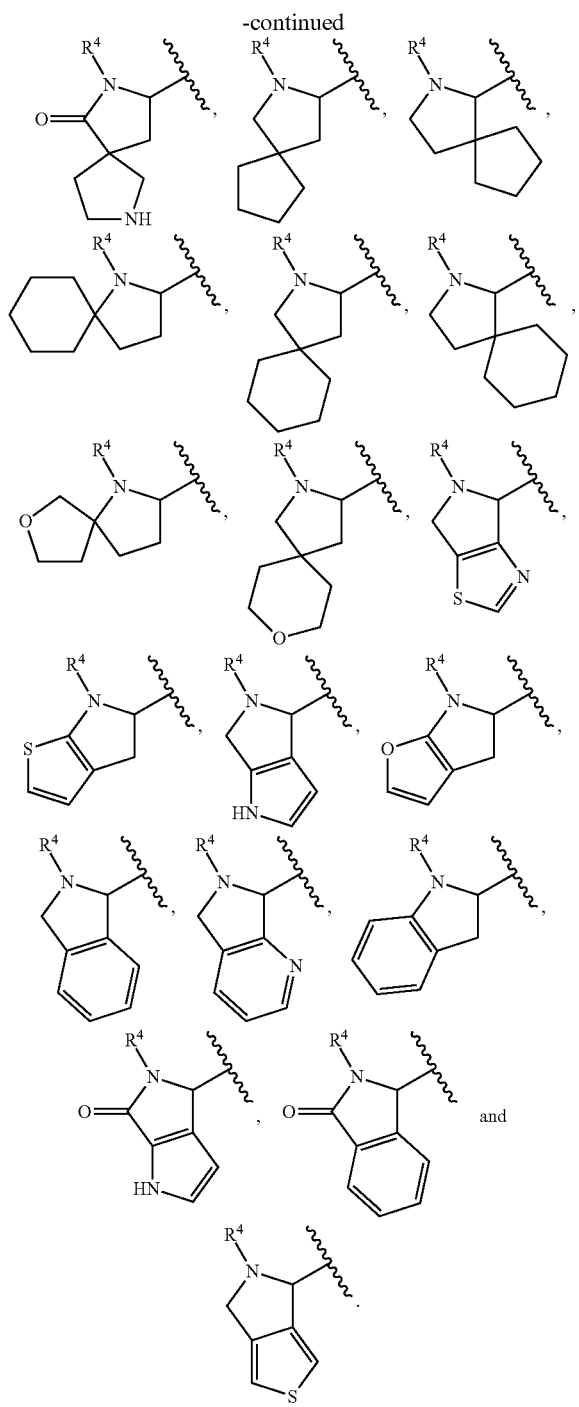
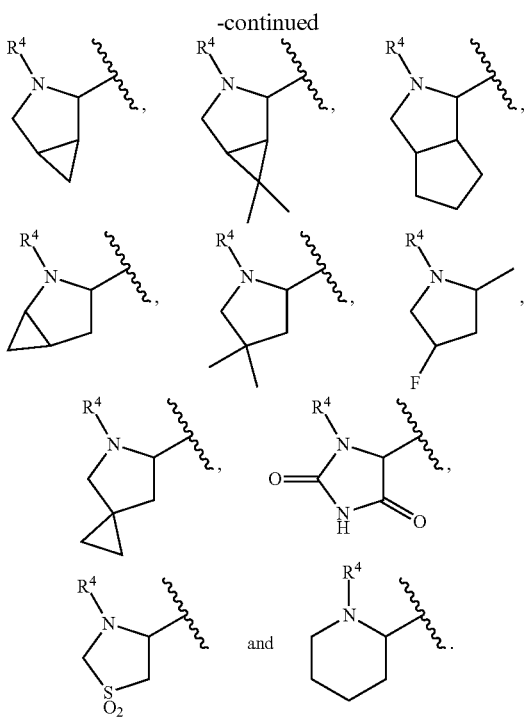
In another embodiment, A and D are each independently selected from:
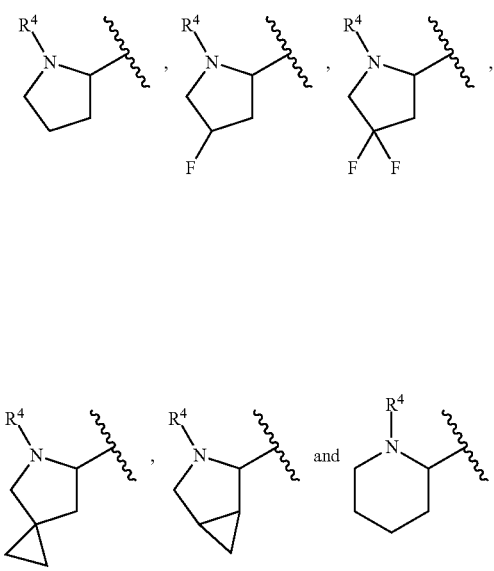
In another embodiment, A and D are each independently selected from:
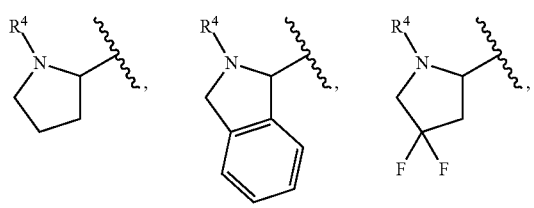
In yet another embodiment, A and D are each independently selected from:
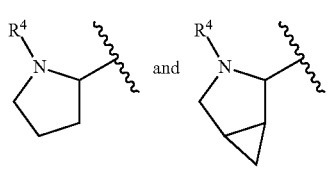

In another embodiment, A and D are each:

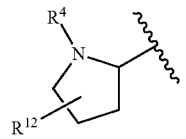

In one embodiment, A and D are each —C(R$^{12}$)N(R$^7$)(R$^{11}$).

In another embodiment, A and D are each independently selected from -alkylene-N(cycloalkyl)-C(O)—CH(alkyl)-NHC(O)O-alkyl, -alkylene-N(cycloalkyl)-C(O)—CH(cycloalkyl)-NHC(O)O-alkyl, -alkylene-N(cycloalkyl)-C(O)—CH(aryl)-NHC(O)O-alkyl and -alkylene-N(cycloalkyl)-C(O)—CH(heteroaryl)-NHC(O)O-alkyl.

In another embodiment, A and D are each independently:

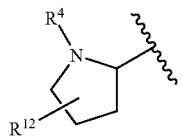

and each R$^4$ is independently —C(O)—[CH(R$^7$)]$_q$N(R$^6$)C(O)O—R$^1$.

In still another embodiment, A and D are each independently

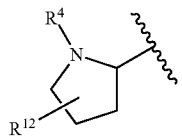

and each R$^4$ is independently

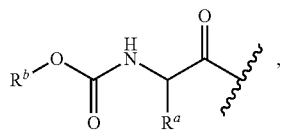

wherein R$^a$ is H, alkyl, -haloalkyl, cycloalkyl or aryl, and R$^b$ is alkyl.

In another embodiment, A and D are each independently

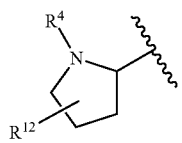

each R$^4$ is independently:

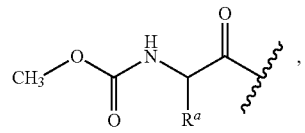

wherein R$^a$ is H, methyl, ethyl, propyl, isopropyl, t-butyl, cyclopropyl, —CH$_2$CH$_2$CF$_3$ or phenyl.

In another embodiment, A and D are each independently

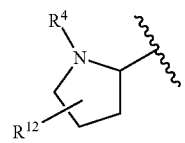

each R$^4$ is independently:

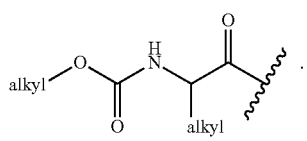

In one embodiment, A and D are each independently selected from:

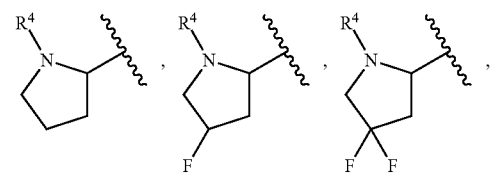

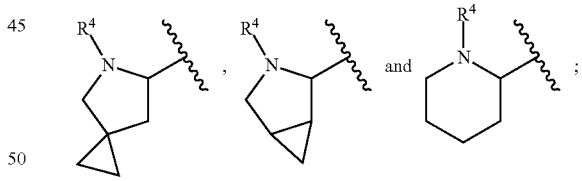

and each occurrence of R$^4$ is independently selected from:

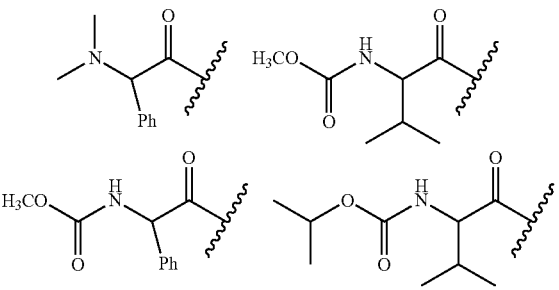

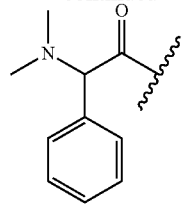
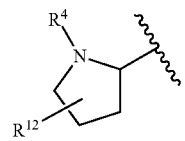

In another embodiment, A and D are each independently

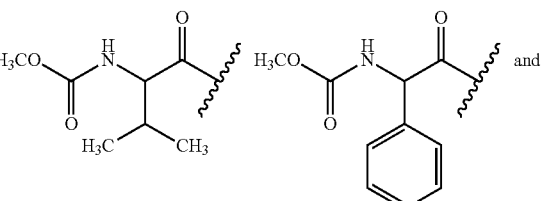

and each occurrence of $R^4$ is independently selected from:

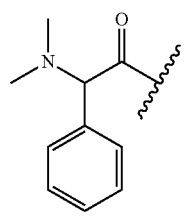

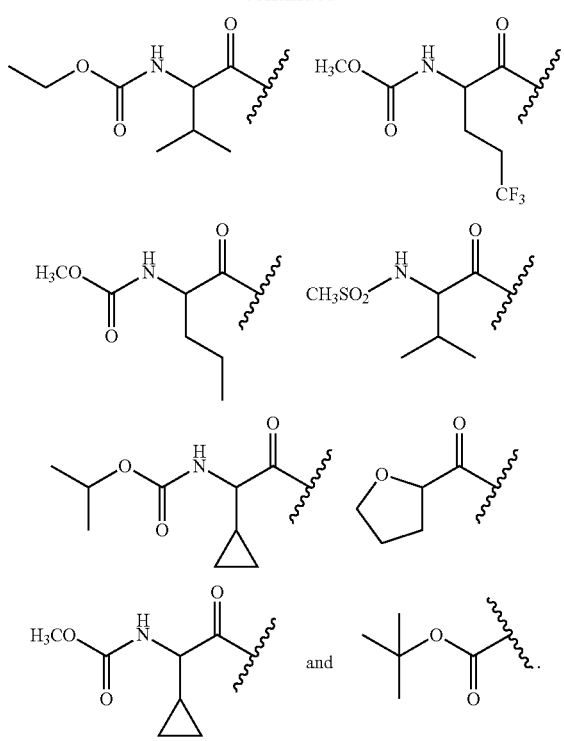

In another embodiment, A and D are each independently selected from:

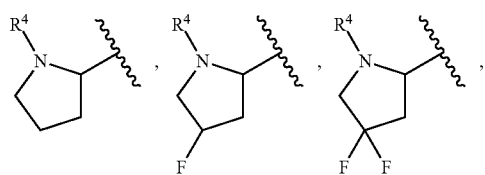

each occurrence of $R^4$ is independently selected from:

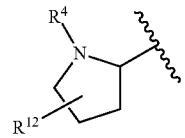

In still another embodiment, A and D are each independently:

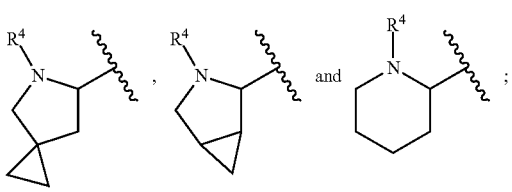

and each occurrence of $R^4$ is:

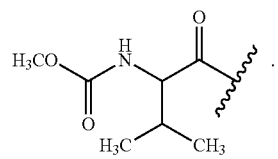

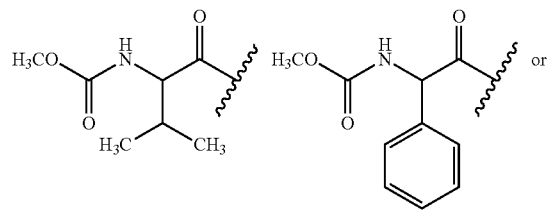

In another embodiment, A and D are each independently -alkylene-N(cycloalkyl)-C(O)—CH(alkyl)-NHC(O)O-alkyl.

In another embodiment, A and D are each independently -alkylene-N(cyclohexyl)-C(O)—CH(isopropyl)-NHC(O)O-methyl.

In a further embodiment, A and D are each independently -alkylene-N(aryl)-C(O)—CH(alkyl)-NHC(O)O-alkyl.

In one embodiment, one of A and D is -alkylene-N($R^7$)($R^{11}$) and the other is a 4 to 7-membered heterocycloalkyl.

In another embodiment, one of A and D is -alkylene-N($R^7$)($R^{11}$) and the other is:

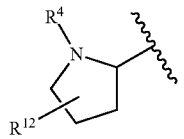

In one embodiment, $M^1$ is —[C($R^7$)$_2$]$_q$—.
In another embodiment, $M^1$ is —C($R^7$)$_2$C($R^7$)$_2$C($R^7$)$_2$—.
In another embodiment, $M^1$ is —C($R^7$)$_2$C($R^7$)$_2$—.
In still another embodiment, $M^1$ is —C($R^7$)$_2$—.
In another embodiment, $M^1$ is —CH$_2$—.
In another embodiment, $M^1$ is —CH$_2$CH$_2$—.
In yet another embodiment, $M^1$ is a bond.
In another embodiment, $M^1$ is —CH$_2$C($R^7$)$_2$CH$_2$—.
In a further embodiment, $M^1$ is —C($R^7$)=C($R^7$)—.
In another embodiment, $M^1$ is —CH=CH—.
In another embodiment, $M^1$ is —CH=N—.
In still another embodiment, $M^1$ is —N=CH—.
In another embodiment, $M^1$ is —[C($R^7$)$_2$]$_m$—O—[C($R^7$)$_2$]$_m$.
In another embodiment, $M^1$ is —C($R^7$)2OC($R^7$)$_2$—.
In yet another embodiment, $M^1$ is —CH$_2$OCH$_2$—.
In another embodiment, $M^1$ is —[C($R^7$)$_2$]$_m$—N($R^6$)-[C($R^7$)$_2$]$_m$—.
In a further embodiment, $M^1$ is —[C($R^7$)$_2$]—N($R^6$)—[C($R^7$)$_2$]—.
In another embodiment, $M^1$ is —CH$_2$N($R^6$)CH$_2$—.
In another embodiment, $M^1$ is —CH$_2$NHCH$_2$—.
In still another embodiment, $M^1$ is —NR$^6$—.
In another embodiment, $M^1$ is [C($R^7$)$_2$]m-S(O)$_2$—[C($R^7$)$_2$]$_m$—.
In another embodiment, $M^1$ is [C($R^7$)$_2$]—S(O)$_2$—[C($R^7$)$_2$]—.
In yet another embodiment, $M^1$ is —CH$_2$S(O)$_2$CH$_2$—.
In another embodiment, $M^1$ is —CH$_2$CH$_2$S(O)$_2$—.
In another embodiment, $M^1$ is —S(O)$_2$CH$_2$—.
In a further embodiment, $M^1$ is —S(O)$_2$—.
In another embodiment, $M^1$ is —S—.
In another embodiment, $M^1$ is —[C($R^7$)$_2$]$_m$—OC(O)N($R^6$)—[C($R^7$)$_2$]$_m$.
In yet another embodiment, $M^1$ is —OC(O)N($R^6$)—[C($R^7$)$_2$]$_m$—.
In another embodiment, $M^1$ is —OC(O)N($R^6$)CH$_2$—.
In another embodiment, $M^1$ is —OC(O)N($R^6$)—.
In still another embodiment, $M^1$ is —OC(O)NH—.
In another embodiment, $M^1$ is —[C($R^7$)$_2$]$_m$N($R^6$)C(O)N($R^6$)[C($R^7$)$_2$]$_m$—.
In another embodiment, $M^1$ is —N($R^6$)C(O)N($R^6$)[C($R^7$)$_2$]$_m$—.
In a further embodiment, $M^1$ is —N($R^{10}$)C(O)N($R^6$)CH$_2$—.
In another embodiment, $M^1$ is —N($R^6$)C(O)N($R^6$)—.
In another embodiment, $M^1$ is —NHC(O)NH—.
In still another embodiment, $M^1$ is —[C($R^7$)$_2$]$_m$—S(O)$_2$N($R^6$)—[C($R^7$)$_2$]$_m$—.
In another embodiment, $M^1$ is —S(O)$_2$N($R^6$)—[C($R^7$)$_2$]$_m$—.
In another embodiment, $M^1$ is —CH$_2$S(O)$_2$N($R^6$)CH$_2$—.

In yet another embodiment, $M^1$ is —S(O)$_2$N($R^6$)CH$_2$—.
In another embodiment, $M^1$ is —CH$_2$S(O)$_2$N($R^6$)—.
In a further embodiment, $M^1$ is —S(O)$_2$N($R^6$)—.
In another embodiment, $M^1$ is —S(O)$_2$NH—.
In another embodiment, $M^1$ is —[C($R^7$)$_2$]$_m$N($R^6$)S(O)$_2$N($R^6$)[C($R^7$)$_2$]$_m$—.
In still another embodiment, $M^1$ is —C($R^7$)$_2$N($R^6$)S(O)$_2$N($R^6$)C($R^7$)$_2$—.
In another embodiment, $M^1$ is —CH$_2$N($R^6$)S(O)$_2$N($R^6$)CH$_2$—.
In another embodiment, $M^1$ is —N($R^6$)S(O)$_2$N($R^6$)CH$_2$—.
In yet another embodiment, $M^1$ is —NHS(O)$_2$NHCH$_2$—.
In another embodiment, $M^1$ is —NHS(O)$_2$NH—.
In another embodiment, $M^1$ is a bond and $M^2$ is other than a bond.
In one embodiment, $M^2$ is —[C($R^7$)$_2$]$_q$—.
In another embodiment, $M^2$ is —C($R^7$)$_2$C($R^7$)$_2$C($R^7$)$_2$—.
In another embodiment, $M^2$ is —C($R^7$)$_2$C($R^7$)$_2$—.
In still another embodiment, $M^2$ is —C($R^7$)$_2$—.
In another embodiment, $M^2$ is —CH$_2$—.
In another embodiment, $M^2$ is —CH$_2$CH$_2$—.
In yet another embodiment, $M^2$ is a bond.
In another embodiment, $M^2$ is —CH$_2$C($R^7$)$_2$CH$_2$—.
In a further embodiment, $M^2$ is —C($R^7$)=C($R^7$)—.
In another embodiment, $M^2$ is —CH=CH—.
In another embodiment, $M^2$ is —CH=N—.
In still another embodiment, $M^2$ is —N=CH—.
In another embodiment, $M^2$ is —[C($R^7$)$_2$]$_m$—O—[C($R^7$)$_2$]$_m$.
In another embodiment, $M^2$ is —C(R)$_2$OC($R^7$)$_2$—.
In yet another embodiment, $M^2$ is —CH$_2$OCH$_2$—.
In another embodiment, $M^2$ is —[C($R^7$)$_2$]$_m$—N($R^6$)—[C($R^7$)$_2$]$_m$—.
In a further embodiment, $M^2$ is —[C($R^7$)$_2$]$_m$—N($R^6$)—[C($R^7$)$_2$]$_m$—.
In another embodiment, $M^2$ is —CH$_2$N($R^6$)CH$_2$—.
In another embodiment, $M^2$ is —CH$_2$NHCH$_2$—.
In still another embodiment, $M^2$ is —NR$^6$—.
In another embodiment, $M^2$ is [C($R^7$)$_2$]$_m$—S(O)$_2$—[C($R^7$)$_2$]$_m$—.
In another embodiment, $M^2$ is [C($R^7$)$_2$]—S(O)$_2$—[C($R^7$)$_2$]—.
In yet another embodiment, $M^2$ is —CH$_2$S(O)$_2$CH$_2$—.
In another embodiment, $M^2$ is —CH$_2$CH$_2$S(O)$_2$—.
In another embodiment, $M^2$ is —S(O)$_2$CH$_2$—.
In a further embodiment, $M^2$ is —S(O)$_2$—.
In another embodiment, $M^2$ is —S—.
In another embodiment, $M^2$ is —[C($R^7$)$_2$]$_m$—OC(O)N($R^6$)—[C($R^7$)$_2$]$_m$—.
In yet another embodiment, $M^2$ is —OC(O)N($R^6$)—[C($R^7$)$_2$]$_m$—.
In another embodiment, $M^2$ is —OC(O)N($R^6$)CH$_2$—.
In another embodiment, $M^2$ is —OC(O)N($R^6$)—.
In still another embodiment, $M^2$ is —OC(O)NH—.
In another embodiment, $M^2$ is —[C($R^7$)$_2$]$_m$N($R^6$)C(O)N($R^6$)[C($R^7$)$_2$]$_m$—.
In another embodiment, $M^2$ is —N($R^6$)C(O)N($R^6$)[C($R^7$)$_2$]$_m$—.
In a further embodiment, $M^2$ is —N($R^{10}$)C(O)N($R^6$)CH$_2$—.
In another embodiment, $M^2$ is —N($R^6$)C(O)N($R^6$)—.
In another embodiment, $M^2$ is —NHC(O)NH—.
In still another embodiment, $M^2$ is —[C($R^7$)$_2$]$_m$—S(O)$_2$N($R^6$)—[C($R^7$)$_2$]$_m$—.
In another embodiment, $M^2$ is —S(O)$_2$N($R^6$)—[C($R^7$)$_2$]$_m$—.

In another embodiment, M² is —CH₂S(O)₂N(R⁶)CH₂—.
In yet another embodiment, M² is —S(O)₂N(R⁶)CH₂—.
In another embodiment, M² is —CH₂S(O)₂N(R⁶)—.
In a further embodiment, M² is —S(O)₂N(R⁶)—.
In another embodiment, M² is —S(O)₂NH—.
In another embodiment, M² is —[C(R⁷)₂]ₘN(R⁶)S(O)₂N(R⁶)[C(R⁷)₂]ₘ—.
In still another embodiment, M² is —C(R⁷)₂N(R⁶)S(O)₂N(R⁶)C(R⁷)₂—.
In another embodiment, M² is —CH₂N(R⁶)S(O)₂N(R⁶)CH₂—.
In another embodiment, M² is —N(R⁶)S(O)₂N(R⁶)CH₂—.
In yet another embodiment, M² is —NHS(O)₂NHCH₂—.
In another embodiment, M² is —NHS(O)₂NH—.
In still another embodiment, M² is a bond and M¹ is other than a bond.
In one embodiment, M¹ and M² are each —C(R¹²)₂—.
In another embodiment, M¹ and M² are each —CH₂—.
In another embodiment; M¹ and M² are each —NH—.
In another embodiment, one of M¹ and M² is —CH₂— and the other is —NH—.
In another embodiment, one of M¹ and M² is a bond.
In another embodiment, one of M¹ and M² is a bond and the other is —CH₂—.
In another embodiment, one of M¹ and M² is a bond and the other is —NH—.
In still another embodiment, one of M¹ and M² is a bond and the other is —O—.
In one embodiment, X¹ is a bond.
In another embodiment, X¹ is —C(R⁵)=C(R⁵)—.
In another embodiment, X¹ is —N=C(R⁵)—.
In still another embodiment, X¹ is —C(R⁵)=NC—.
In another embodiment, X¹ is —C(R⁵)=N—.
In another embodiment, X¹ is —O—.
In yet another embodiment X¹ is —N(R⁶)—.
In another embodiment, X¹ is —S—.
In a further embodiment, X¹ is —S(O)₂—.
In another embodiment, X¹ is —C(R⁵)(CH(R⁵))ₘ—.
In another embodiment, X¹ is —N—.
In still another embodiment, X¹ is —N—CH(R⁵)CH(R⁵)—.
In another embodiment, X¹ is —C(R⁵)NHCH(R⁵)—.
In another embodiment, X¹ is —C(R⁵)CH(R⁵)NH—.
In yet another embodiment, X¹ is —C(R⁵)O—.
In another embodiment, X¹ is —C(R⁵)N(R⁶)—.
In a further embodiment, X¹ is —N—N(R⁶)—.
In another embodiment, X¹ is —C(R⁵)S—.
In another embodiment, X¹ is —C(R⁵)S(O)₂—.
In one embodiment, X² is a bond.
In another embodiment, X² is —C(R⁵)=C(R⁵)—.
In another embodiment, X² is —N=C(R⁵)—.
In still another embodiment, X² is —C(R⁵)=NC—.
In another embodiment, X² is —C(R⁵)=N—. In another embodiment, X² is —O—.
In yet another embodiment X² is —N(R⁶)—.
In another embodiment, X² is —S—.
In a further embodiment, X² is —S(O)₂—.
In another embodiment, X² is —(CH(R⁵))ₘC(R⁵)—.
In another embodiment, X² is —N—.
In still another embodiment, X² is —CH(R⁵)CH(R⁵)N—.
In another embodiment, X² is —CH(R⁵)NHC(R⁵)—.
In another embodiment, X² is —NHCH(R⁵)C(R⁵)—.
In yet another embodiment, X² is —O—C(R⁵)—.
In another embodiment, X² is —N(R⁶)C(R⁵)—.
In another embodiment, X² is —N(R⁶)—N—.
In a further embodiment, X² is —S—C(R⁵)—.

In another embodiment, X² is —S(O)₂C(R⁵)—.
In one embodiment, Z¹ is a bond.
In another embodiment, Z¹ is —C(R⁵)=C(R⁵)—.
In another embodiment, Z¹ is —N=C(R⁵)—.
In still another embodiment, Z¹ is —C(R⁵)=NC—.
In another embodiment, Z¹ is —C(R⁵)=N—.
In another embodiment, Z¹ is —O—.
In yet another embodiment Z¹ is —N(R⁶)—.
In another embodiment, Z¹ is —S—.
In a further embodiment, Z¹ is —S(O)₂—.
In another embodiment, Z¹ is —C(R⁵)(CH(R⁵))ₘ—.
In another embodiment, Z¹ is —N—.
In still another embodiment, Z¹ is —NCH(R⁵)CH(R⁵)—.
In another embodiment, Z¹ is —C(R⁵)NHCH(R⁶)—.
In another embodiment, Z¹ is —C(R⁵)CH(R⁵)NH—.
In yet another embodiment, Z¹ is —C(R⁵)O—.
In another embodiment, Z¹ is —C(R⁵)N(R⁶)—.
In a further embodiment, Z¹ is —N—N(R⁶)—.
In another embodiment, Z¹ is —C(R⁵)S—.
In another embodiment, Z¹ is —C(R⁵)S(O)₂—.
In one embodiment, Z² is a bond.
In another embodiment, Z² is —C(R⁵)=C(R⁵)—.
In another embodiment, Z² is —N=C(R⁵)—.
In still another embodiment, Z² is —C(R⁵)=NC—.
In another embodiment, Z² is —C(R⁵)=N—.
In another embodiment, Z² is —O—.
In yet another embodiment Z² is —N(R⁶)—.
In another embodiment, Z² is —S—.
In a further embodiment, Z² is —S(O)₂—.
In another embodiment, Z² is —(CH(R⁵))ₘC(R⁵)—.
In another embodiment, Z² is —N—.
In still another embodiment, Z² is —CH(R⁵)CH(R⁵)N—.
In another embodiment, Z² is —CH(R⁵)NHC(R⁵)—.
In another embodiment, Z² is —NHCH(R⁵)C(R⁵)—.
In yet another embodiment, Z² is —O—C(R⁵)—.
In another embodiment, Z² is —N(R⁶)C(R⁵)—.
In another embodiment, Z² is —N(R⁶)—N—.
In a further embodiment, Z² is —S—C(R⁵)—.
In another embodiment, Z² is —S(O)₂C(R⁵)—
In one embodiment, the group:

has the structure

-continued
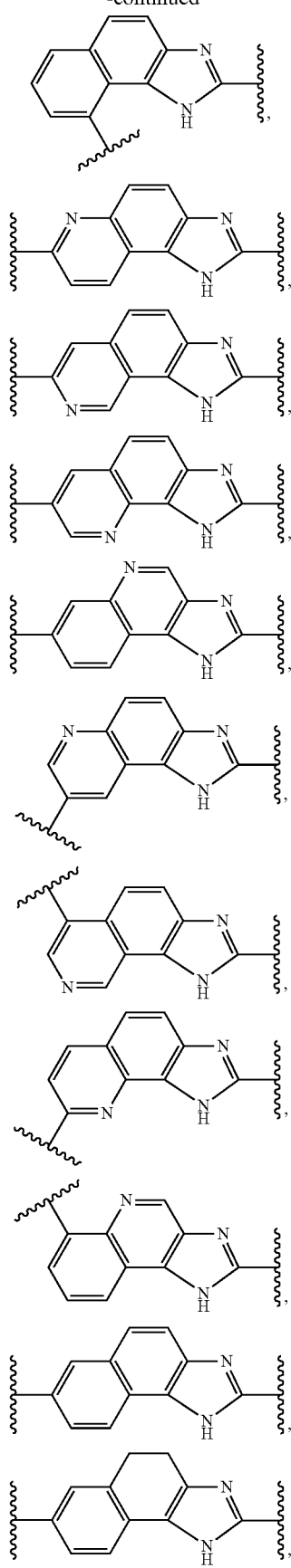
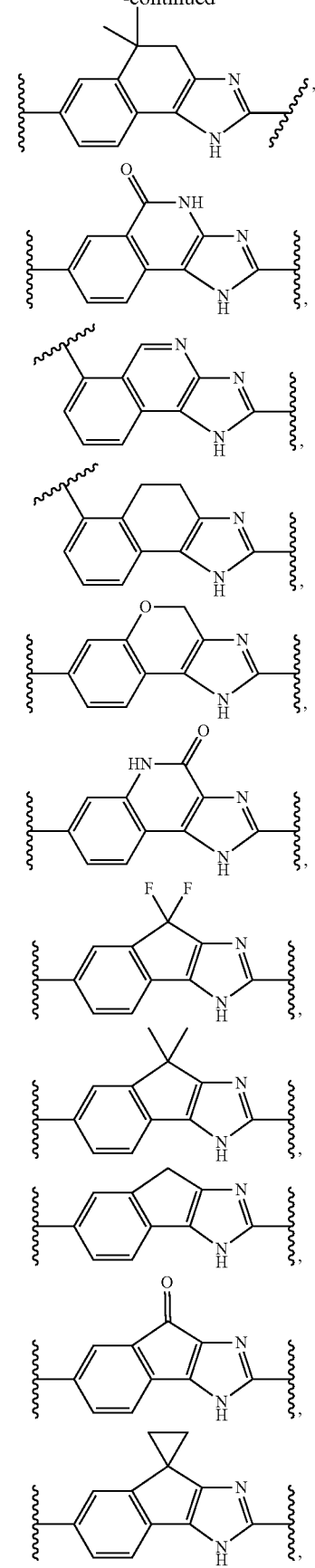

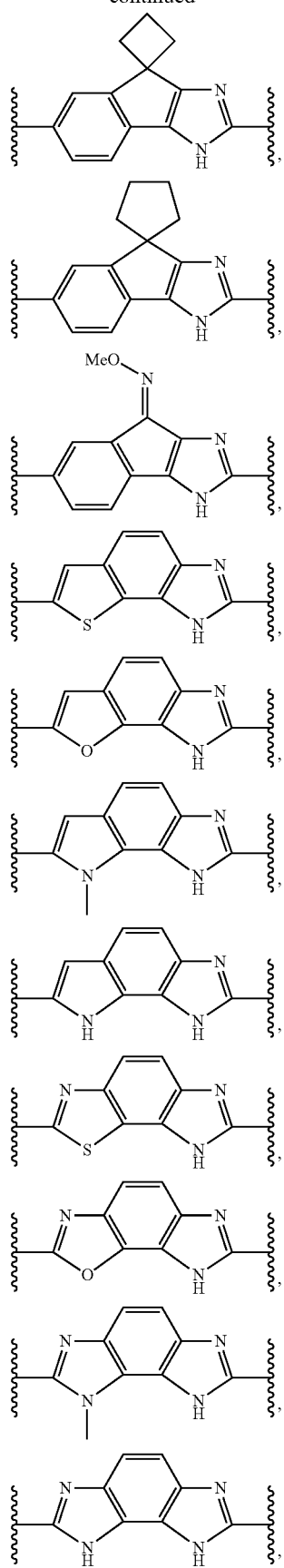
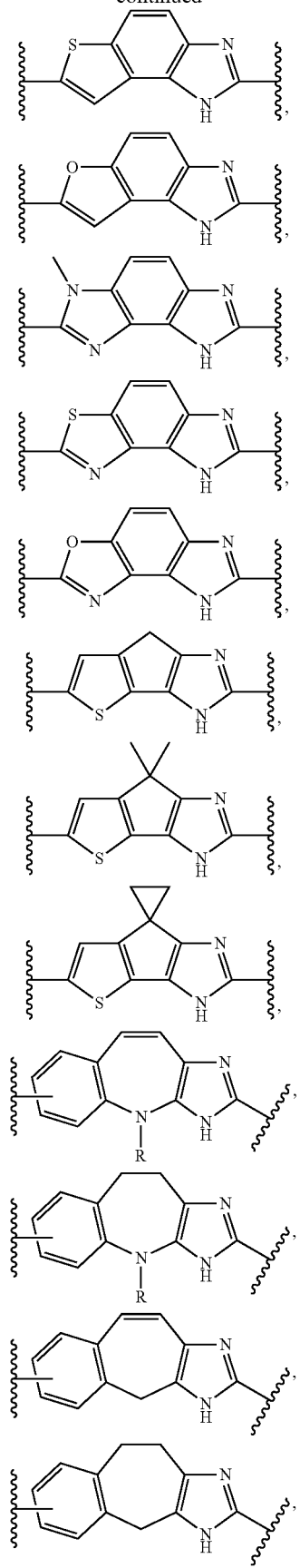

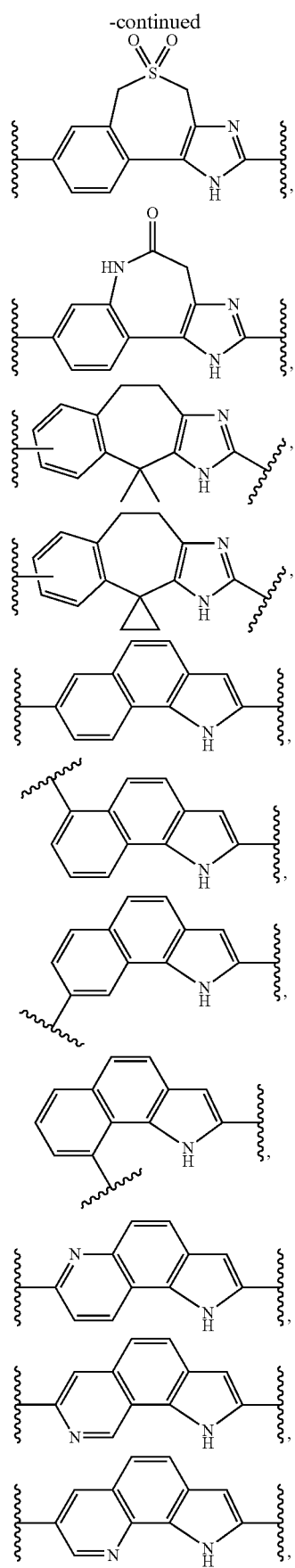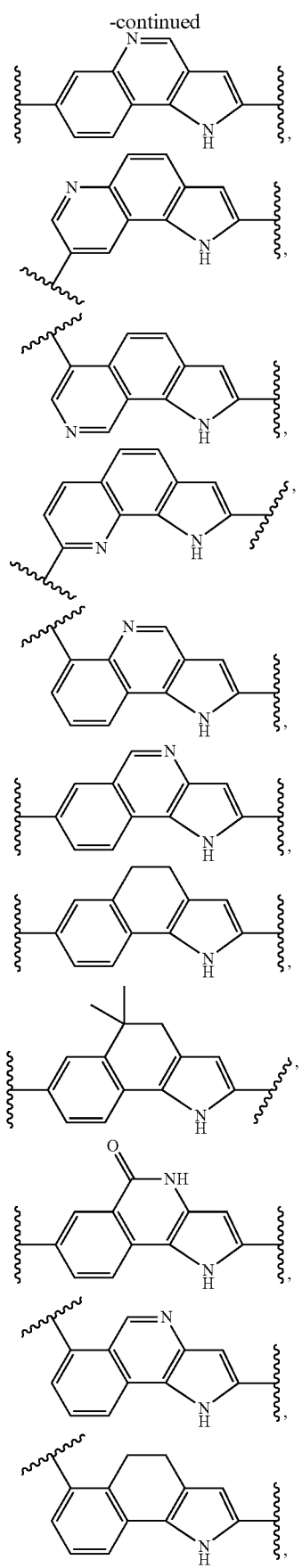

-continued
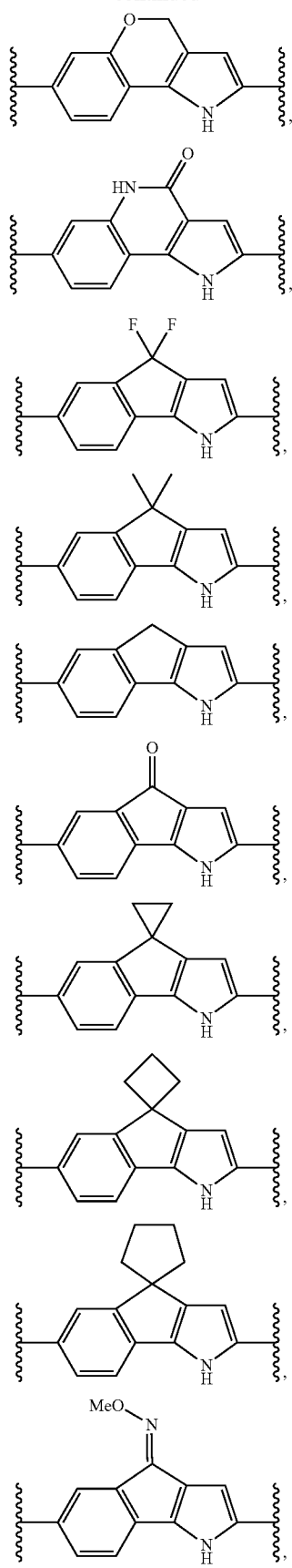
-continued
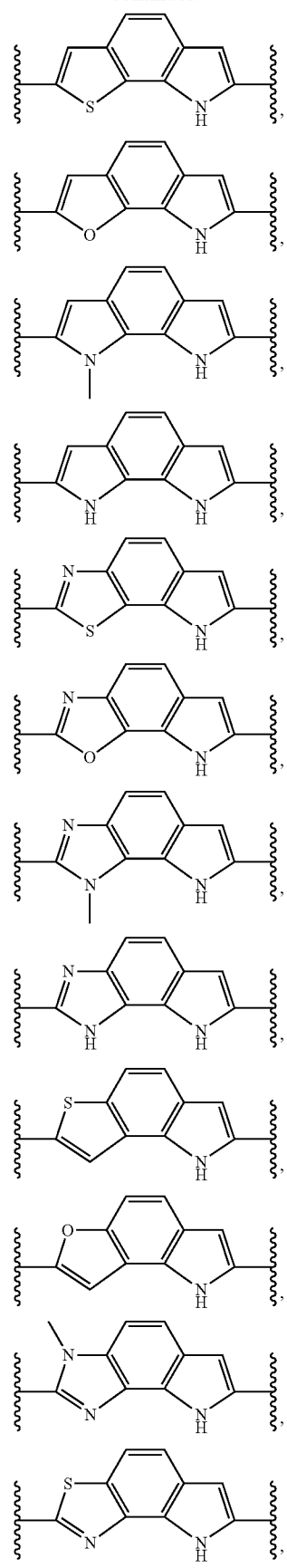

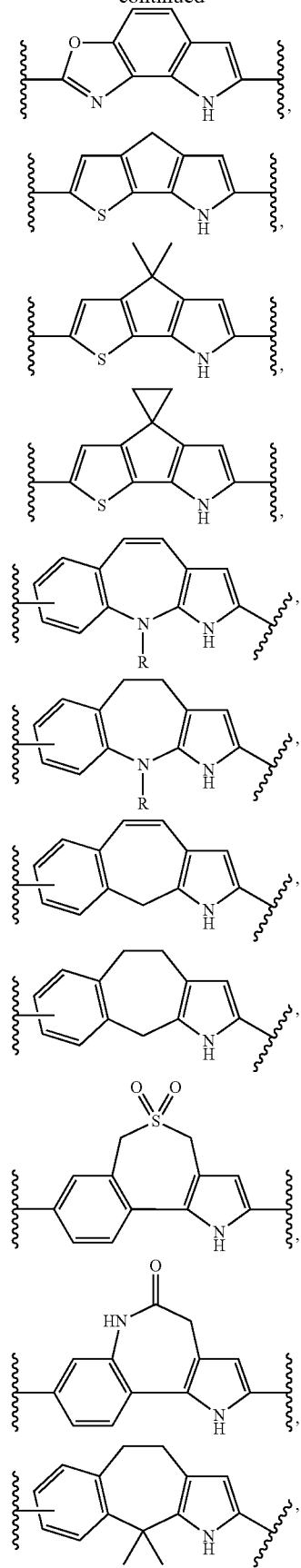
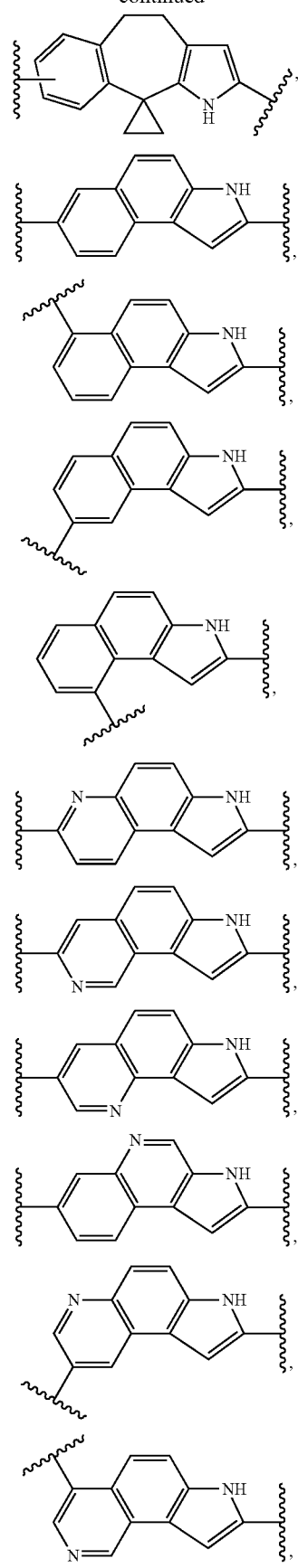

53
-continued
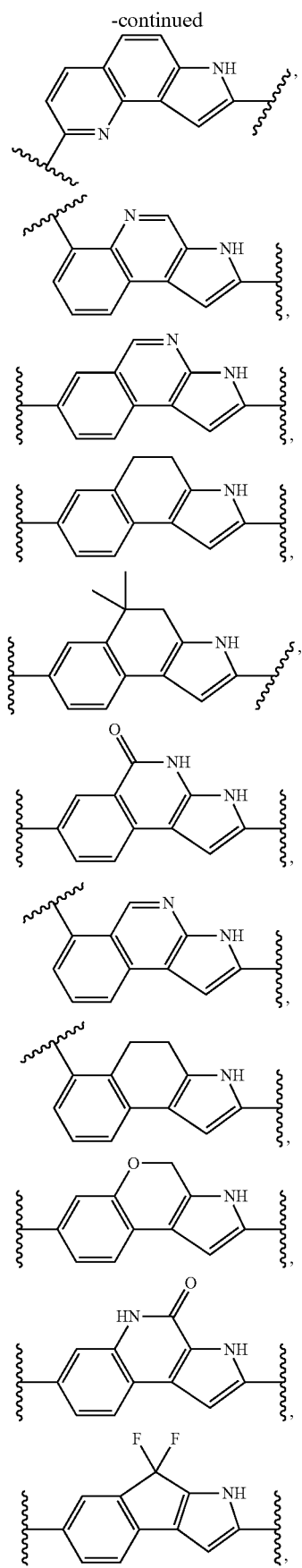
54
-continued
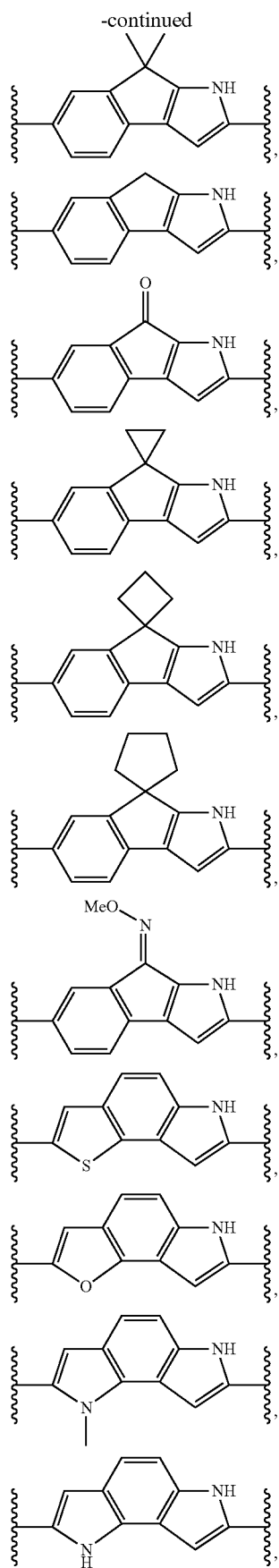

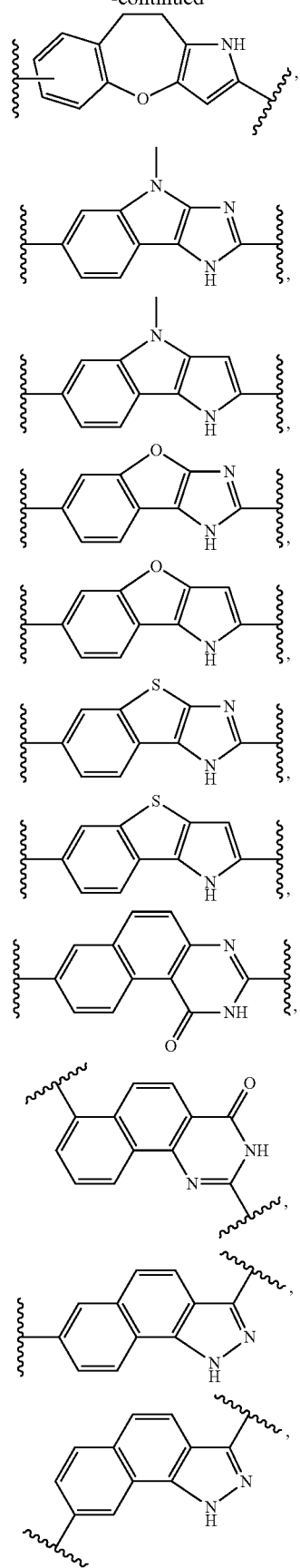
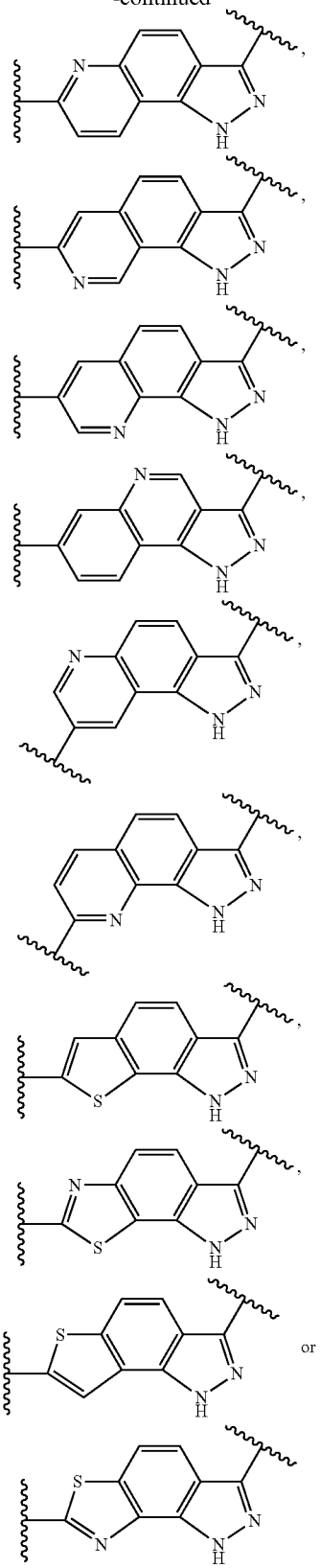
wherein either available bond on any of the above divalent groups can connect to either group flanking the above divalent groups.

In another embodiment, the group:
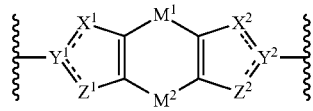
has the structure:
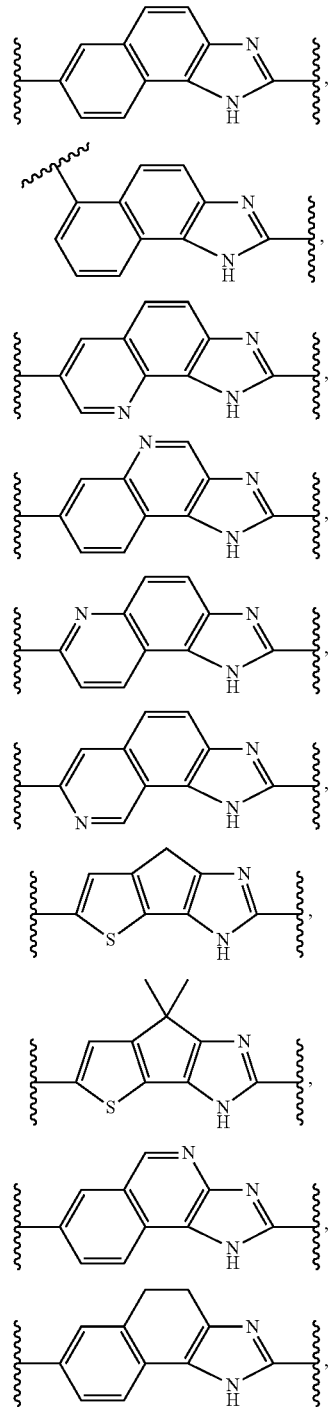
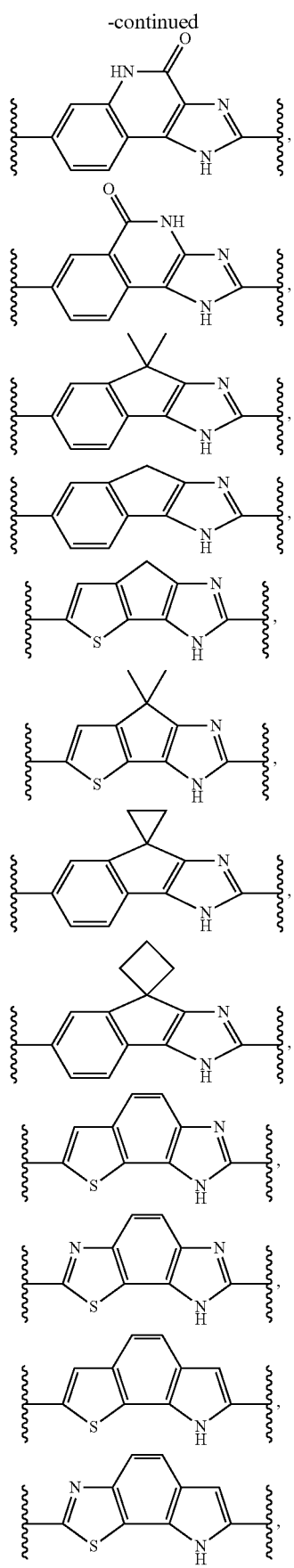

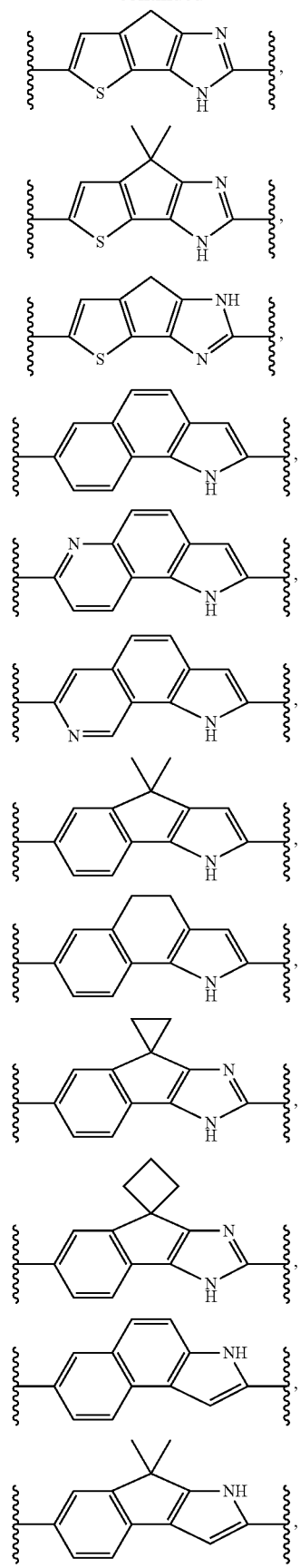
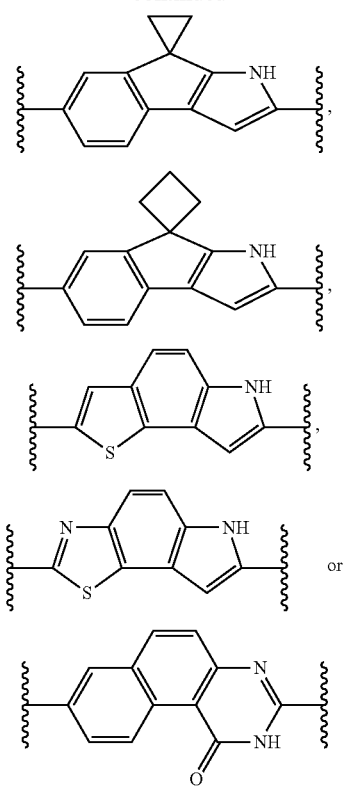
wherein either available bond on any of the above divalent groups can connect to either group flanking the above divalent groups.
In another embodiment, the group:
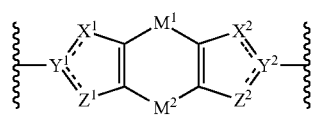
has the structure:
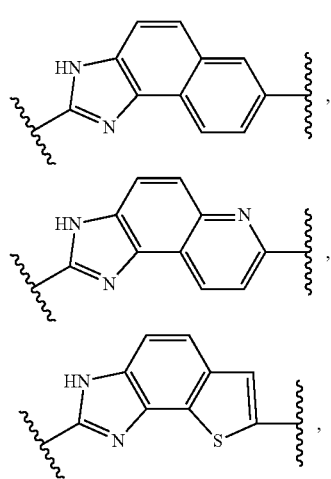

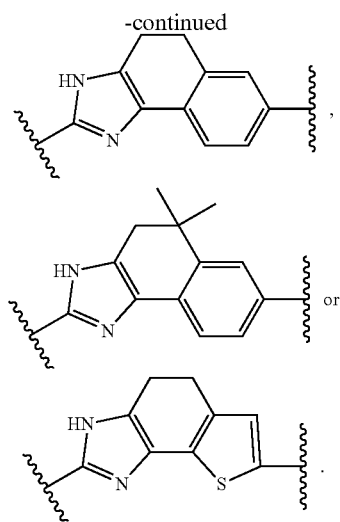

In one embodiment, $R^4$ is —$C_1$-$C_6$alkyl.
In another embodiment, $R^4$ is halo:
In another embodiment, $R^4$ is —C(O)—[C($R^5_2$)$]_q$N($R^6$)$_2$.
In still another embodiment, $R^4$ is —C(O)—[CH($R^5$)$]_q$N($R^6$)C(O)—$R^1$.
In another embodiment, $R^4$ is —C(O)—[CH($R^5$)$]_q$N($R^6$)C(O)O—$R^1$.
In another embodiment, $R^4$ is —C(O)—[CH($R^5$]$_q$C(O)O—$R^1$.
In yet another embodiment, $R^4$ is —C(O)[CH($R^5$]$_q$N($R^6$)SO$_2$—$R^1$.
In another embodiment, $R^4$ is -alkylene-N($R^6$)—[CH($R^5$]$_q$—N($R^6$)—C(O)O—$R^1$.
In one embodiment, each occurrence of $R^4$ is independently selected from:

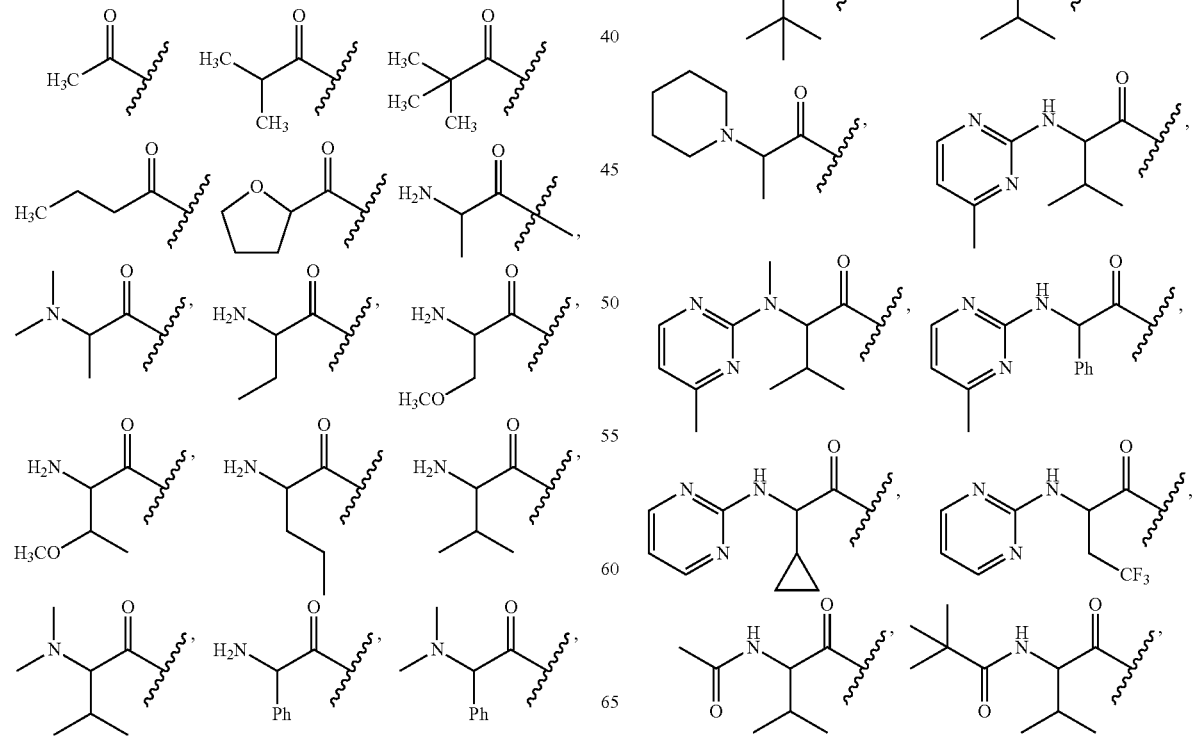

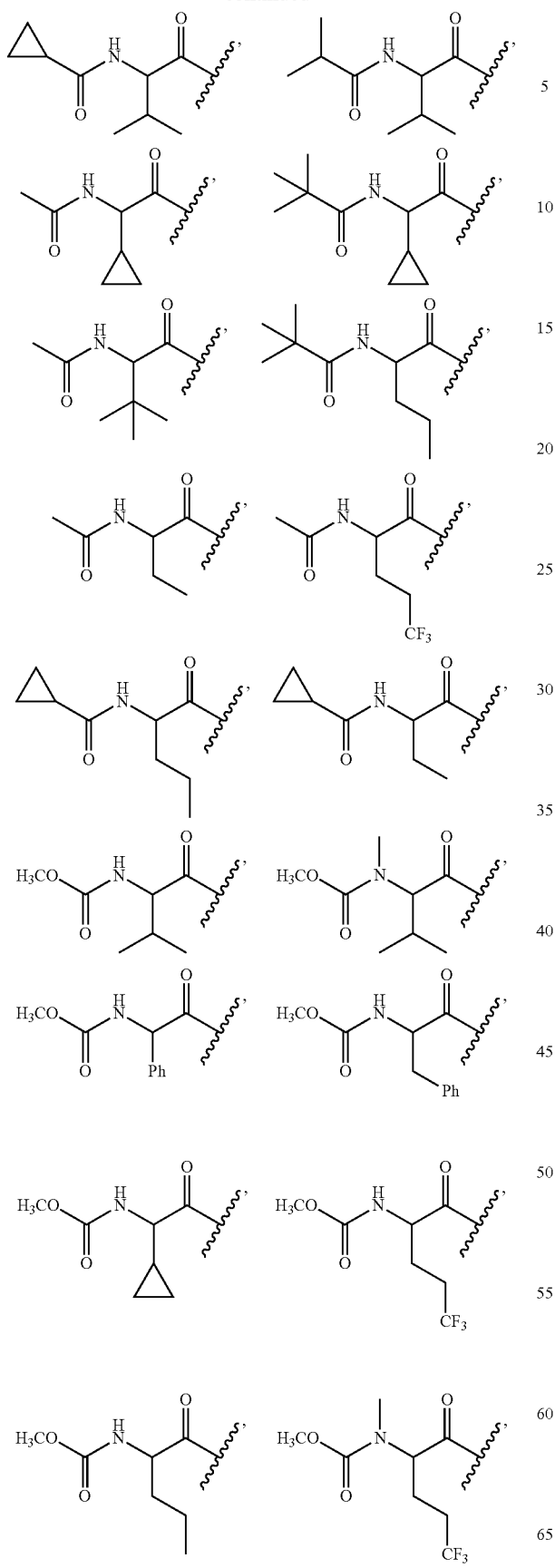
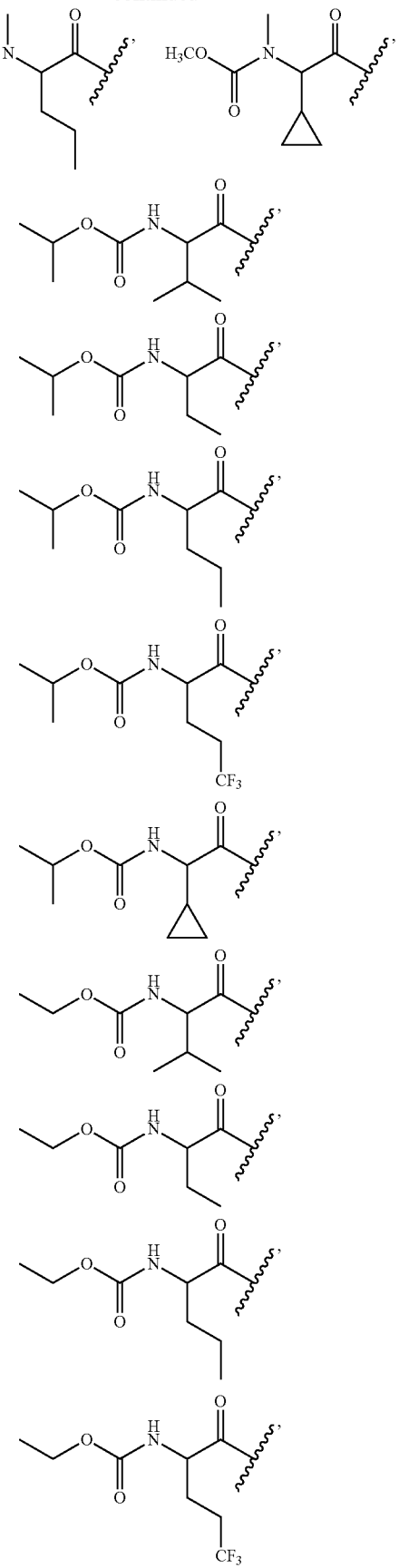

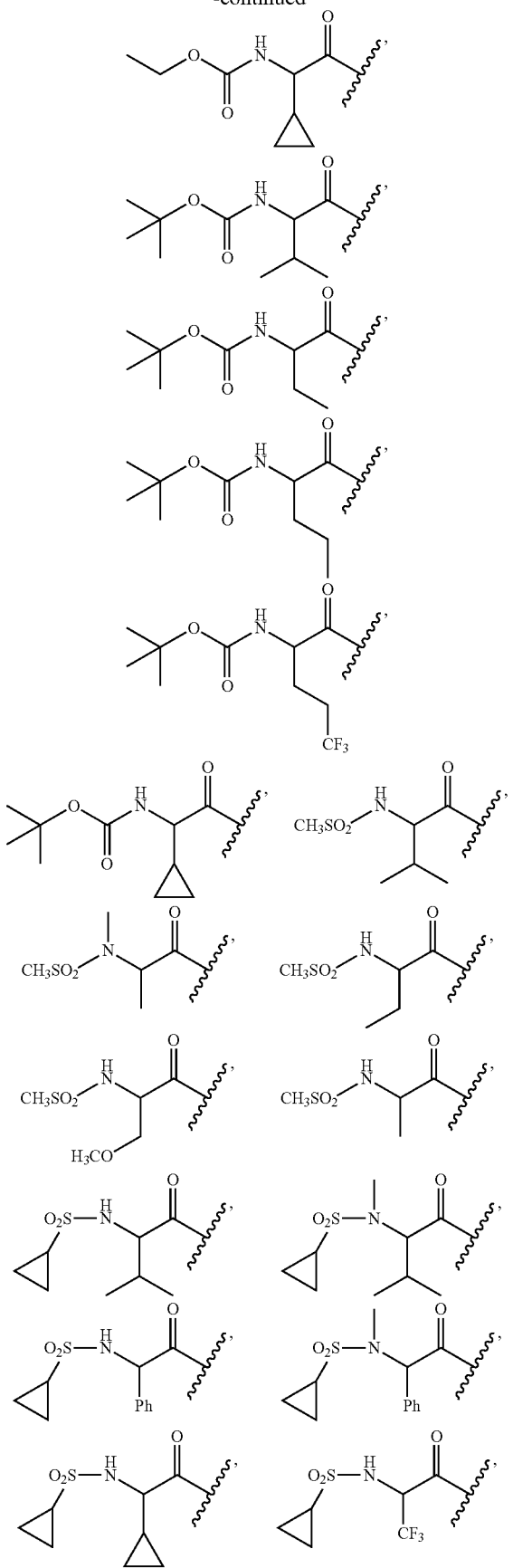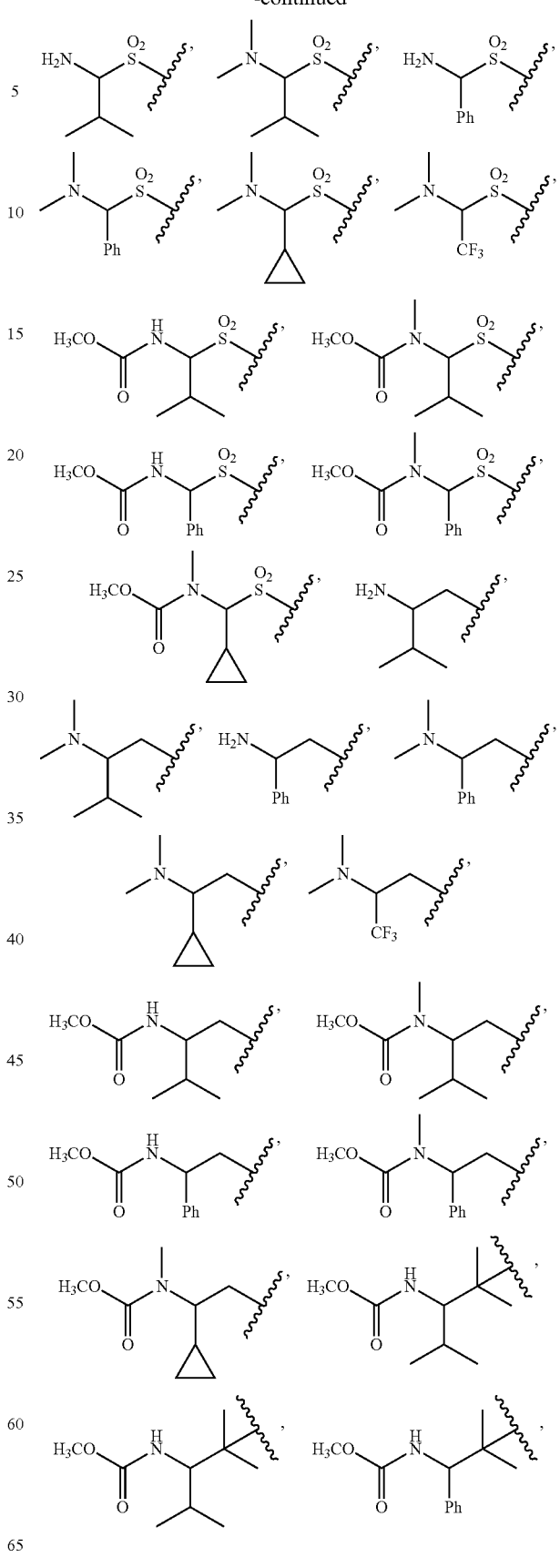

-continued

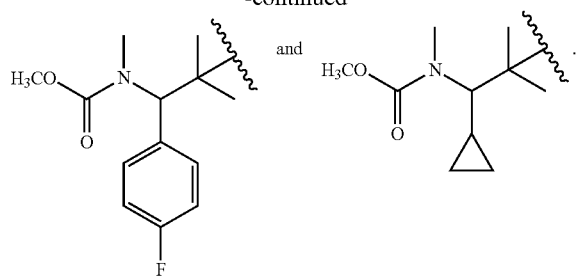
and

In another embodiment, each occurrence of R⁴ is independently selected from:

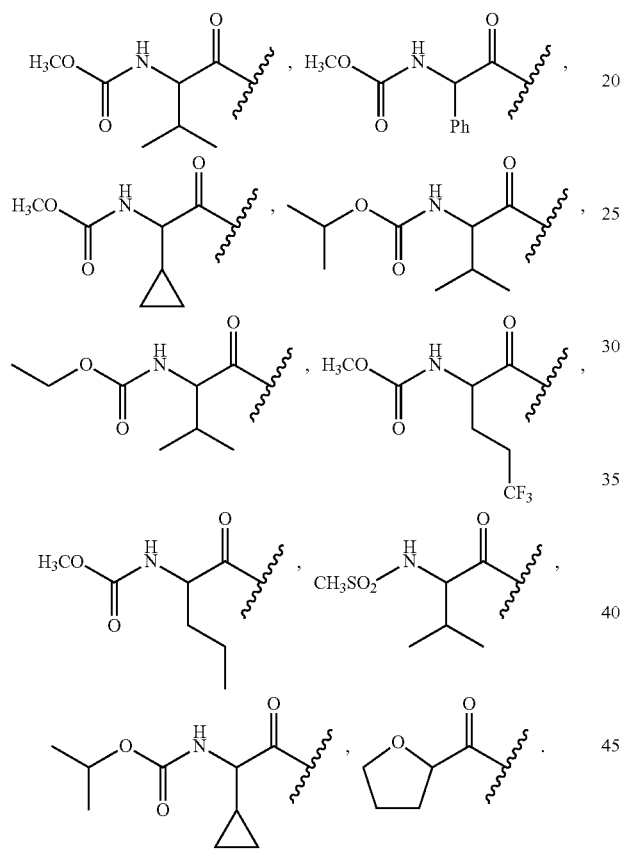

In another embodiment, each occurrence of R⁴ is independently —C(O)—[CH(R⁷)]$_q$N(R⁶)C(O)O—R¹.

In another embodiment, each occurrence of R⁴ is independently:

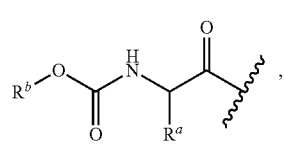

wherein R$^a$ is H, alkyl, haloalkyl, cycloalkyl or aryl, and R$^b$ is alkyl.

In another embodiment, each occurrence of R⁴ is independently:

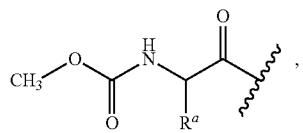

wherein R$^a$ is H, methyl, ethyl, propyl, isopropyl, t-butyl, cyclopropyl, —CH₂CH₂CF₃, or phenyl.

In another embodiment, each occurrence of R⁴ is independently:

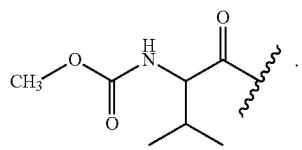 [SMILES: *C(=O)C(NC(=O)OC)C(C)C]

In one embodiment, a Compound of Formula (I) has the formula:

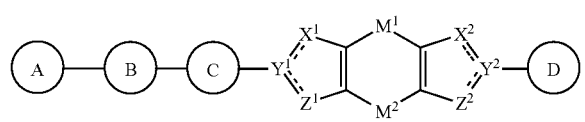

(Ia)

or a pharmaceutically acceptable salt thereof, wherein:

A is —C(R¹²)N(R⁷)(R¹¹),

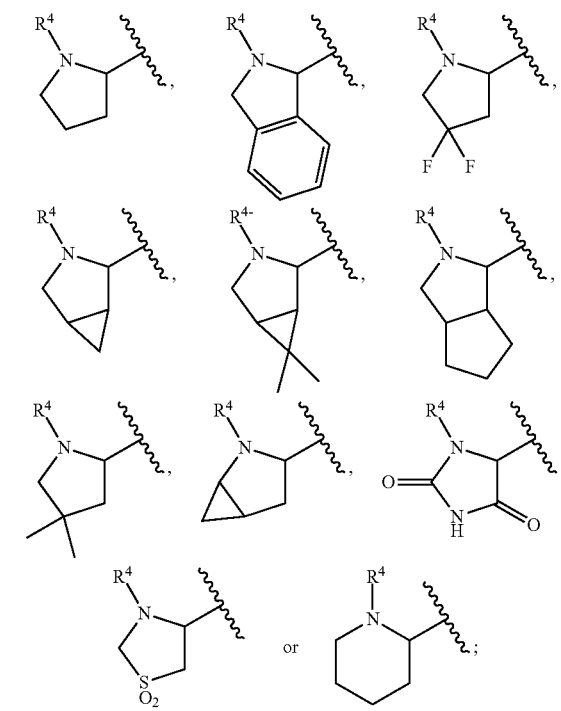

B is
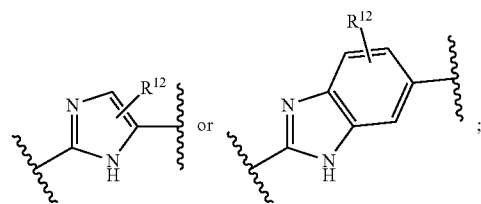
C is
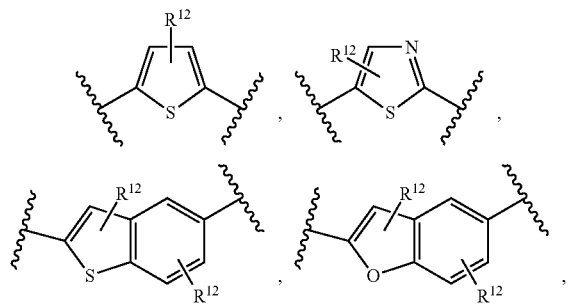
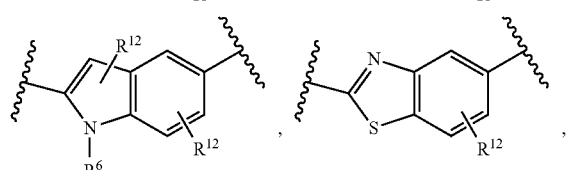
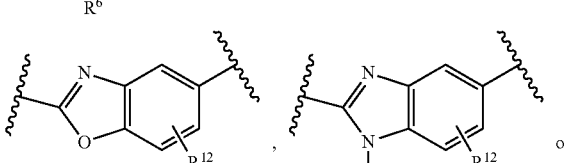
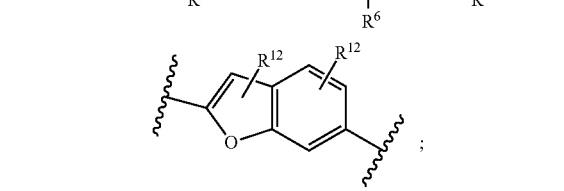
D is —C(R$^{12}$)N(R$^{7}$)(R$^{11}$),
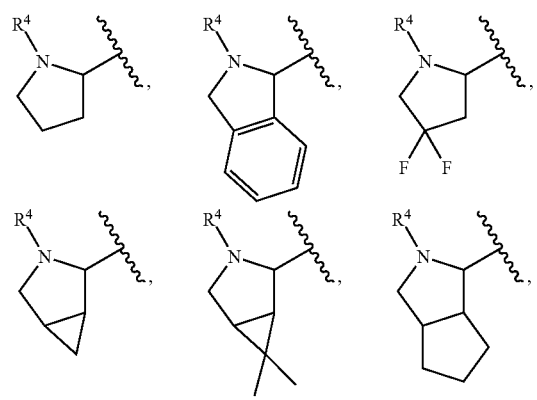
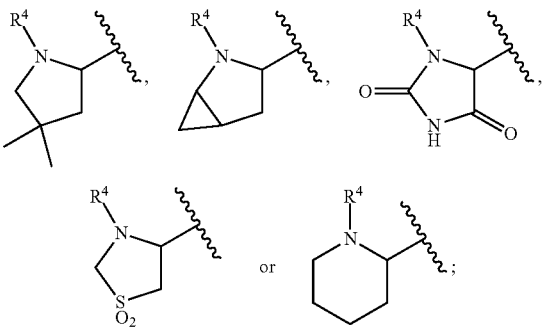
the group:
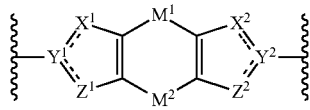
has the structure:
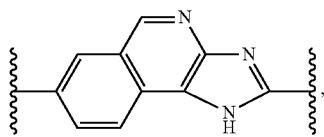
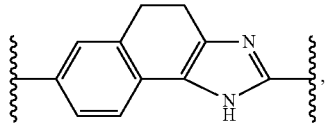
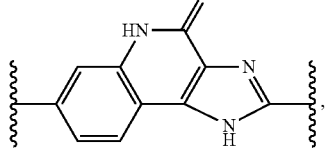
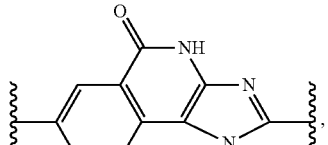
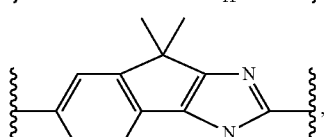
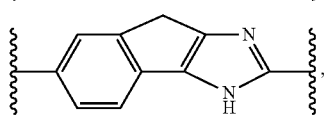
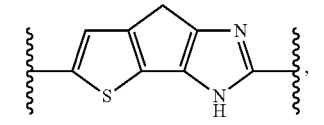

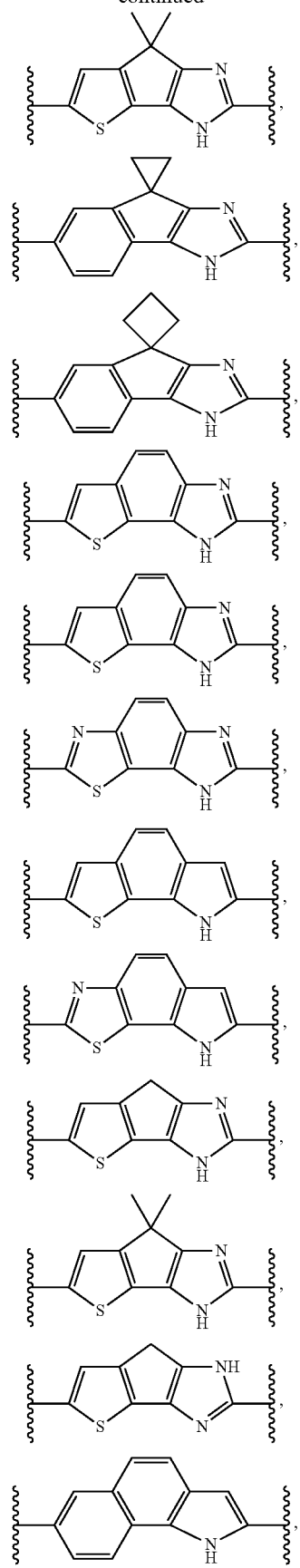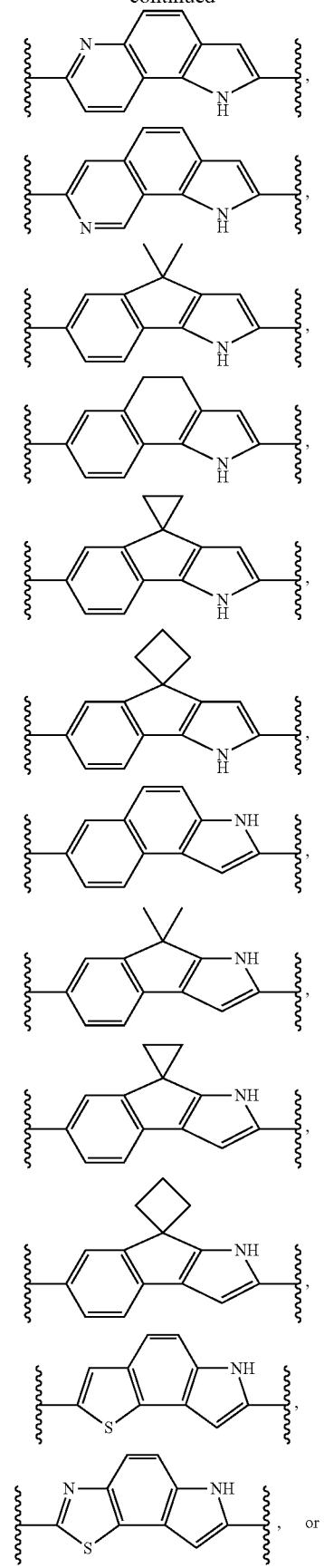

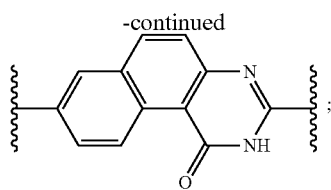

each occurrence of $R^1$ is independently $C_1$-$C_6$ alkyl, $C_1$-$C_6$ haloalkylraryl, 3 to 7 membered cycloalkyl, 4 to 7 membered heterocycloalkyl or heteroaryl, wherein an aryl, cycloalkyl, heterocycloalkyl or heteroaryl group can be optionally and independently substituted with up to three $R^2$ groups;

each occurrence of $R^2$ is independently $C_1$-$C_6$ alkyl, aryl, 3 to 7 membered cycloalkyl, 4 to 7 membered heterocycloalkyl, heteroaryl, halo, $C_1$-$C_6$ haloalkyl, —CN, —$OR^3$, —$N(R^3)_2$, —$C(O)R^{10}$, —$C(O)OR^3$, —$C(O)N(R^3)_2$, —NHC(O)$R^{10}$, —NHC(O)NH$R^3$, —NHC(O)O$R^3$, —OC(O)$R^{10}$, —$SR^3$ or —$S(O)_2R^{10}$;

each occurrence of $R^3$ is independently H, $C_1$-$C_6$ alkyl, $C_1$-$C_6$ haloalkyl, aryl, 3 to 7 membered cycloalkyl, 4 to 7 membered heterocycloalkyl or heteroaryl wherein an aryl, cycloalkyl, heterocycloalkyl or heteroaryl group can be optionally and independently substituted with up to three groups independently selected from hydroxy, halo, alkyl, aminoalkyl, and haloalkyl.

each occurrence of $R^4$ is independently H, —C(O)—[C($R^7$)$_2$]$_q$N($R^6$)$_2$, —C(O)—[C($R^7$)$_2$]$_q$N($R^6$)C(O)—$R^1$, —C(O)—[C($R^7$)$_2$]$_q$N($R^6$)C(O)O—$R^1$, —C(O)—[C($R^7$)$_2$]$_q$C(O)O—$R^1$, —C(O)[C($R^7$)$_2$]$_q$N($R^6$)SO$_2$—$R^1$ or -alkylene-N($R^6$)—[C($R^7$)$_2$]—N($R^6$)—C(O)O—$R^1$;

each occurrence of $R^5$ is independently H, $C_1$-$C_6$ alkyl, 3 to 7-membered cycloalkyl, aryl or heteroaryl;

each occurrence of $R^6$ is independently H, $C_1$-$C_6$ alkyl, 3 to 7-membered cycloalkyl, 4 to 7-membered heterocycloalkyl, aryl, or heteroaryl, wherein a cycloalkyl, heterocycloalkyl, aryl or heteroaryl group can be optionally and independently substituted with up to two $R^8$ groups, and wherein two $R^6$ groups that are attached to a common nitrogen atom, together with the nitrogen atom to which they are attached, can optionally join to form a 4 to 7-membered heterocycloalkyl group;

each occurrence of $R^7$ is independently H, $C_1$-$C_6$ alkyl, 3 to 7-membered cycloalkyl, 4 to 7-membered heterocycloalkyl, aryl, heteroaryl, wherein a cycloalkyl, heterocycloalkyl, aryl or heteroaryl group can be optionally and independently substituted with up to 3 substituents, which can be the same or different, and are selected from $C_1$-$C_6$ alkyl, halo, —$C_1$-$C_6$ haloalkyl, $C_1$-$C_6$ hydroxyalkyl, —OH, —C(O)NH—($C_1$-$C_6$ alkyl), —C(O)N($C_1$-$C_6$ alkyl)$_2$, —O—($C_1$-$C_6$ alkyl), —NH$_2$, —NH($C_1$-$C_6$ alkyl), —N($C_1$-$C_6$ alkyl)z and —NHC(O)—($C_1$-$C_6$ alkyl), and wherein two geminal $R^7$ groups, together with the common carbon atom to which they are attached, can optionally join to form —C(O)—, —C(S)—, —C(=N$R^9$)—, —C(=NO$R^9$)—, a 3 to 7-membered cycloalkyl- group or a 4 to 7-membered heterocycloalkyl group, such that no two adjacent —C($R^7$)$_2$— groups can join to form a —C(O)—C(O)—, —C(S)—C(S)—, —C(O)—C(S)— or —C(S)—C(O)— group;

each occurrence of $R^8$ is independently H or $C_1$-$C_6$ alkyl;

each occurrence of $R^9$ is independently H, $C_1$-$C_6$ alkyl, 3 to 7-membered cycloalkyl or 4 to 7-membered heterocycloalkyl;

each occurrence of $R^{10}$ is independently $C_1$-$C_6$ alkyl, $C_1$-$C_6$ haloalkyl, aryl, 3 to 7-membered cycloalkyl, 4 to 7-membered heterocycloalkyl or heteroaryl;

each occurrence of $R^{11}$ is independently —C(O)—[C($R^7$)$_2$]$_q$N($R^6$)$_2$, —C(O)—[C($R^7$)$_2$]$_q$N($R^6$)C(O)—$R^1$, —C(O)—[C($R^7$)$_2$]$_q$N($R^6$)C(O)O—$R^1$, —C(O)—[C($R^7$)$_2$]$_q$C(O)O—$R^1$, —C(O)[C($R^7$)$_2$]$_q$N($R^6$)SO$_2$—$R^1$ or -alkylene-N($R^6$)—[C($R^7$)$_2$]$_q$—N($R^6$)—C(O)O—$R^1$;

each occurrence of $R^{12}$ is H, $C_1$-$C_6$alkyl, 3 to 7-membered cycloalkyl, 4 to 7-membered heterocycloalkyl, aryl, heteroaryl, halo, $C_1$-$C_6$ haloalkyl, —CN, —$OR^3$, —$N(R^3)_2$, —$C(O)R^{10}$, —$C(O)OR^3$, —$C(O)N(R^3)_2$, —NHC(O)$R^{10}$, —NHC(O)NH$R^3$, —NHC(O)O$R^3$, —OC(O)$R^{10}$, —$SR^3$ or —$S(O)_2R^{10}$; and wherein two $R^{12}$ groups together with the carbon atoms to which they are attached, can optionally join to form a 5 to 7-membered cycloalkyl or 4 to 7-membered heterocycloalkyl group;

each occurrence of m is independently an integer ranging from 0 to 2; and each occurrence of q is independently an integer ranging from 1 to 4.

In one embodiment, for the Compounds of Formula (Ia), A and D are each:

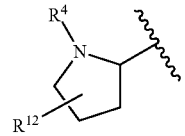

and each occurrence of $R^4$ is:

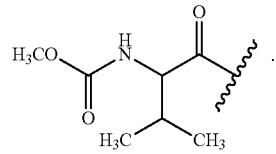

In another embodiment, for the Compounds of Formula (Ia), the group:

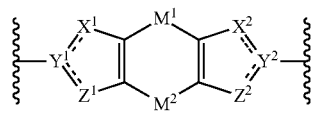

has the structure:

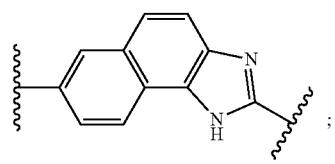 [SMILES: *c1ccc2c(ccc3nc(*)[nH]c32)c1]

and
C is a bond or:

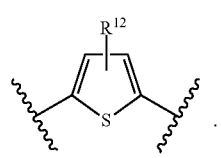

In another embodiment, for the Compounds of Formula (Ia), the group:

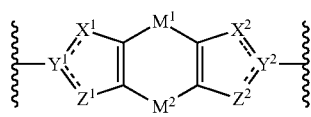

has the structure:

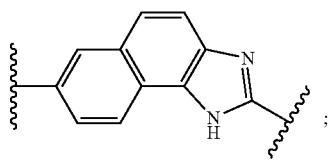 [SMILES: *c1ccc2c(ccc3nc(*)[nH]c32)c1]

C is a bond or:

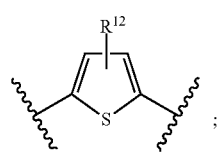

A and D are each:

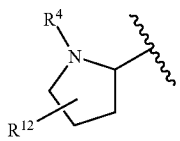

and each occurrence of $R^4$ is

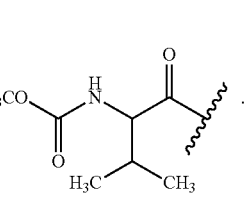

In one embodiment, variable A, B, C, D, $M^1$, $M^2$, $X^1$, $X^2$, $Y^1$, $Y^2$, $Z^1$ and $Z^2$ in the Compounds of Formula (I) are selected independently from each other.

In another embodiment, a Compound of Formula (I) is in purified form.

In another embodiment, a Compound of Formula (I) has one or more of its hydrogen atoms replaced with a deuterium atom.

Non-limiting examples of the Compounds of Formula (I) include compounds 1-45 as depicted below. These compounds can be made using the methods and Examples set forth herein.

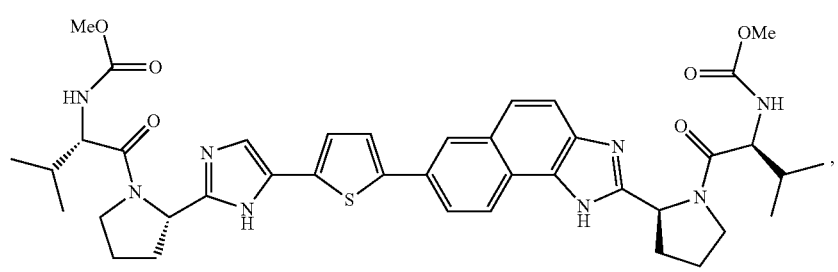

1

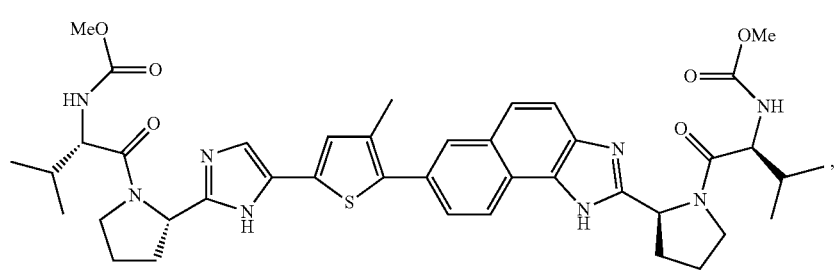

2

-continued
3
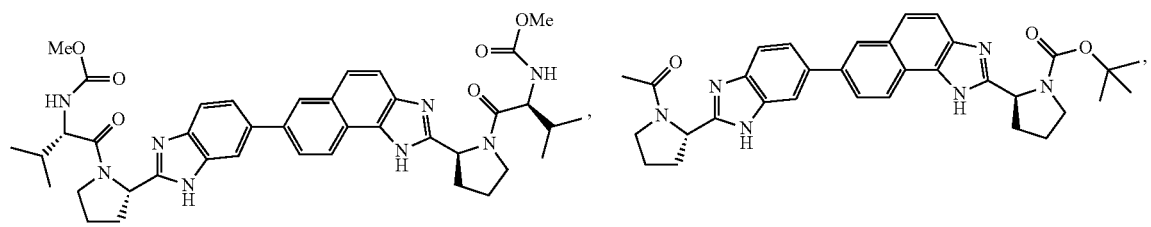
4
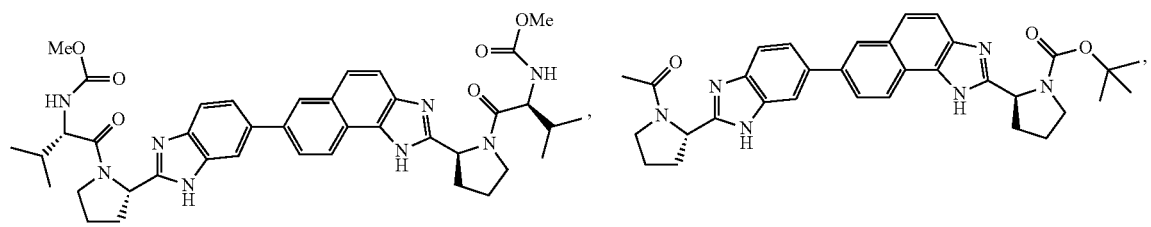
5
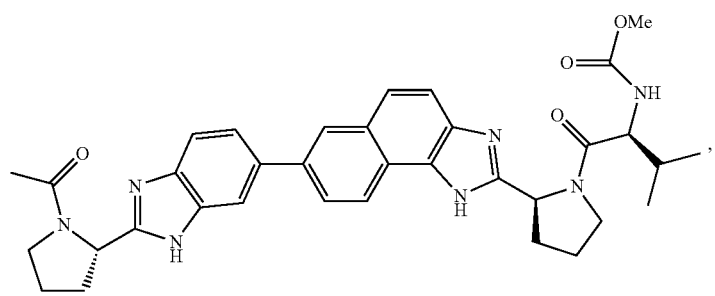
6
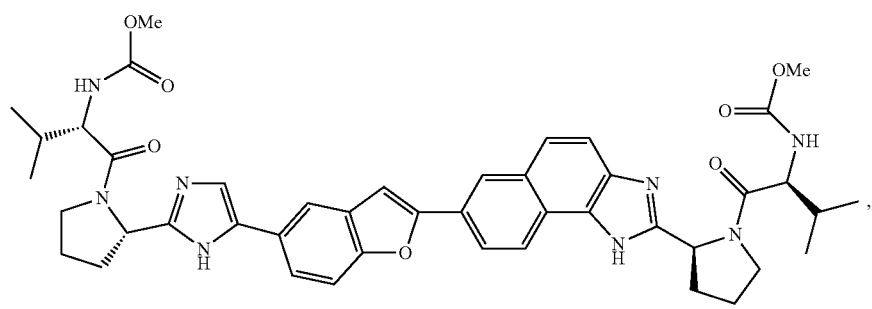
7
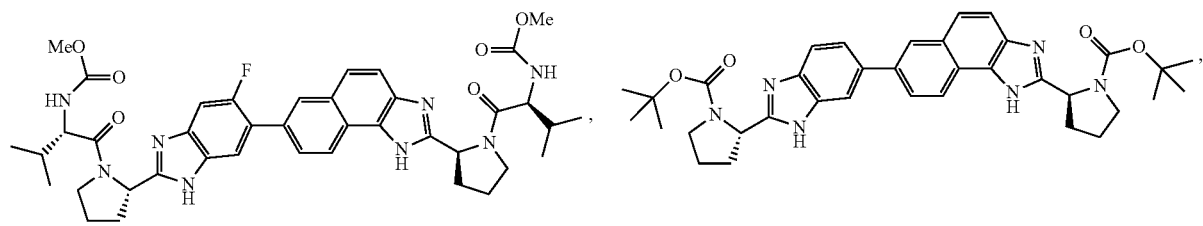
8
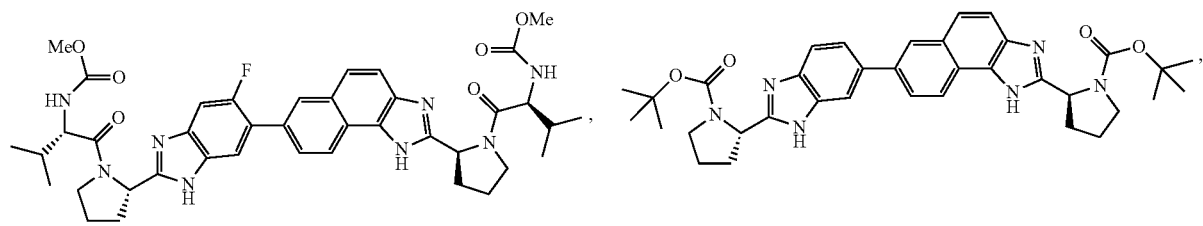
9
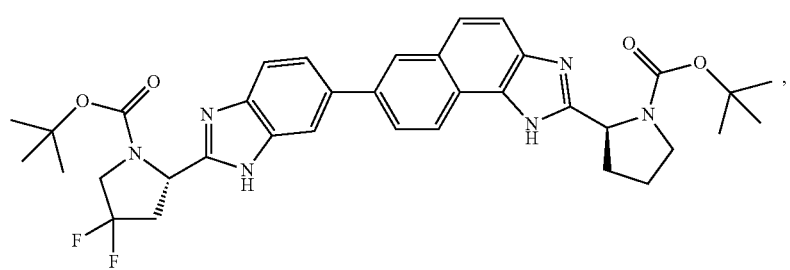

-continued
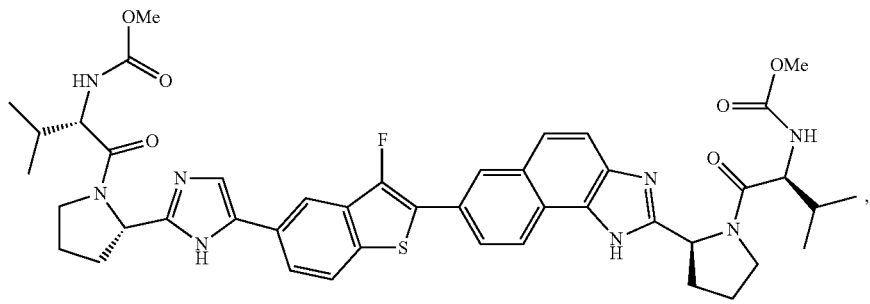
10
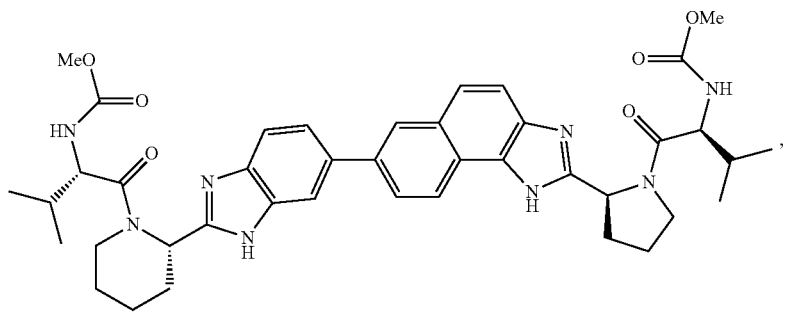
11
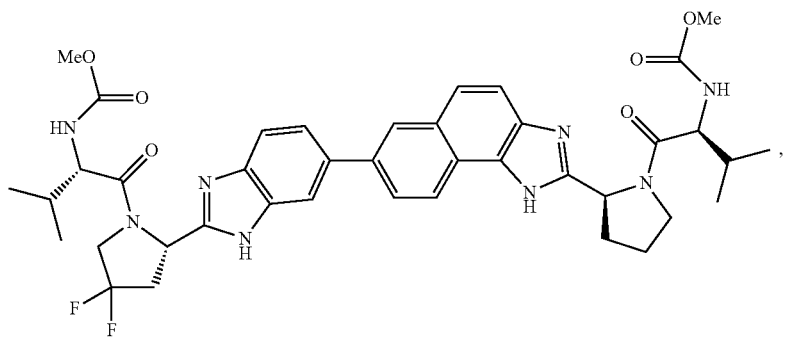
12
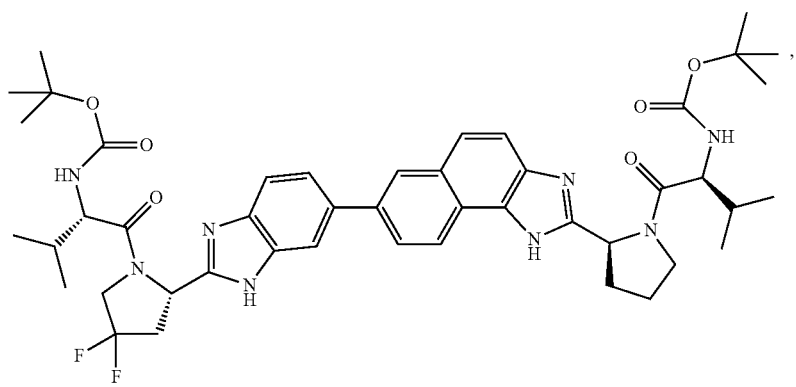
13
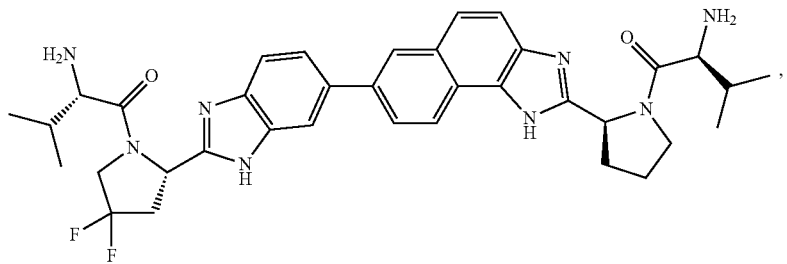
14

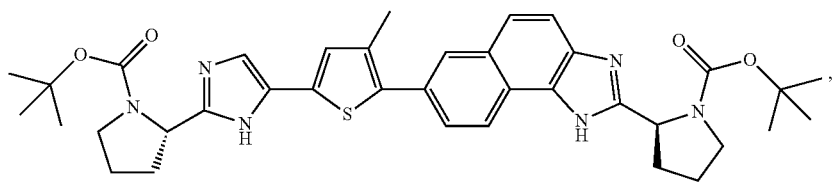
15
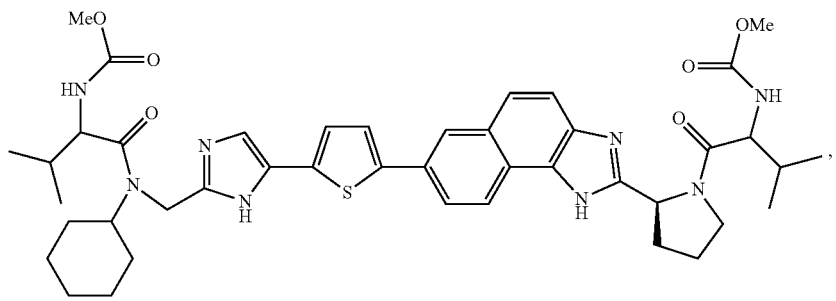
16
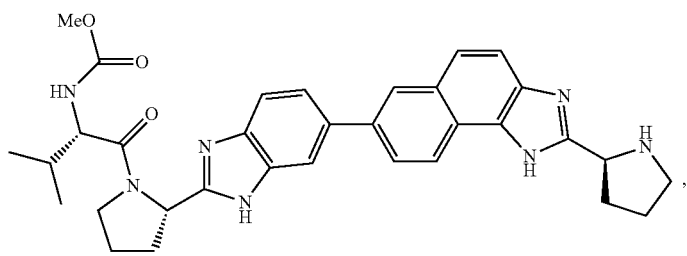
17
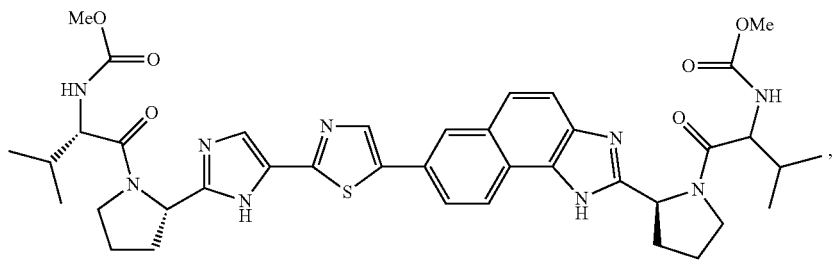
18
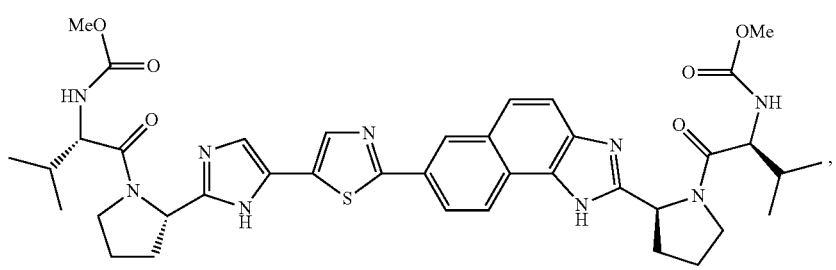
19
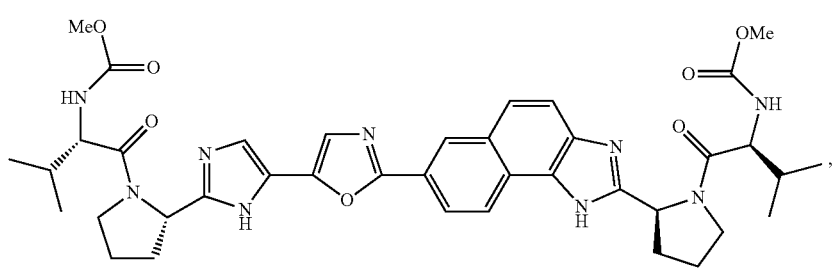
20

-continued
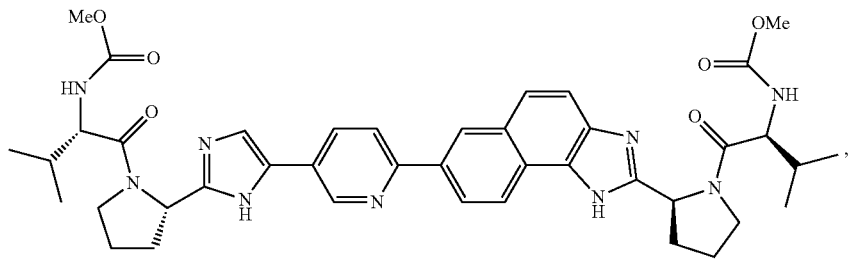
21
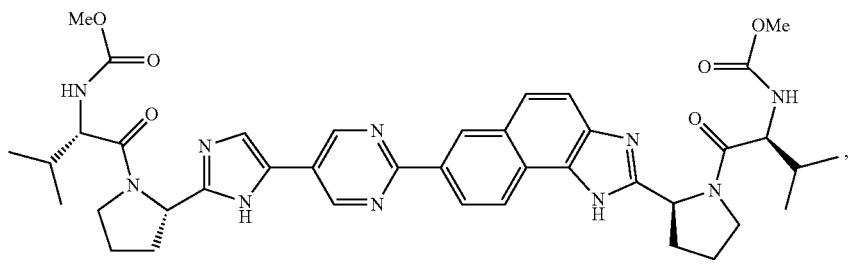
22
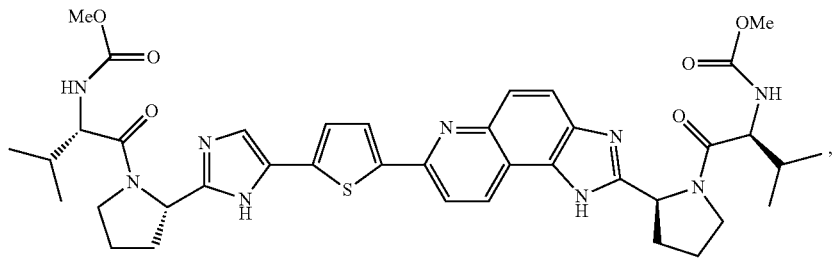
23
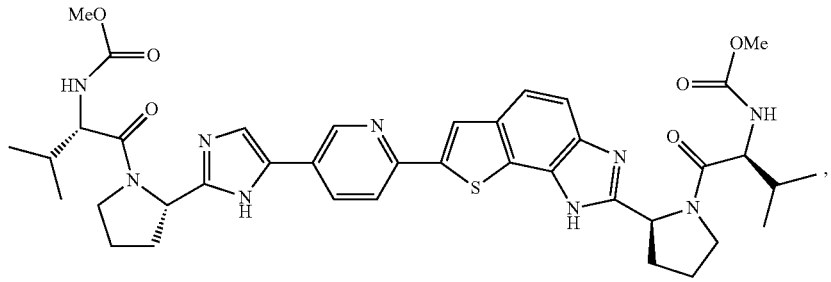
24
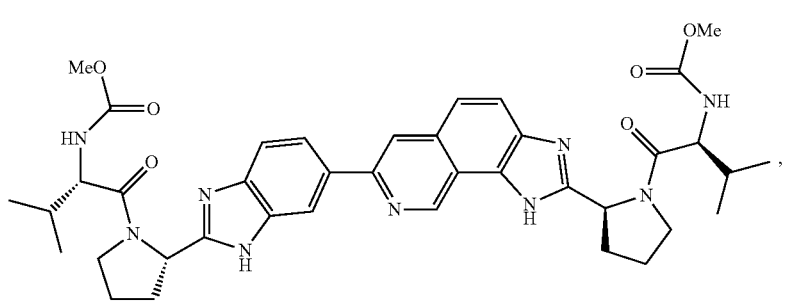
25
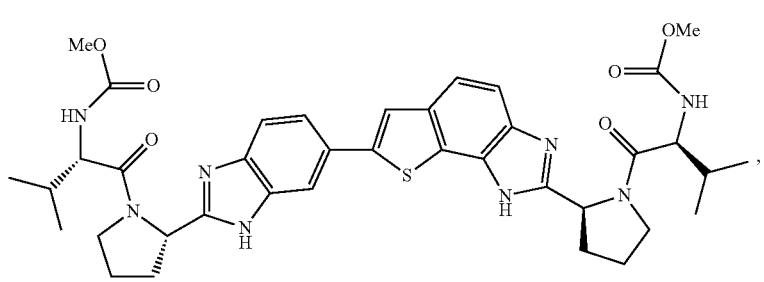
26

27
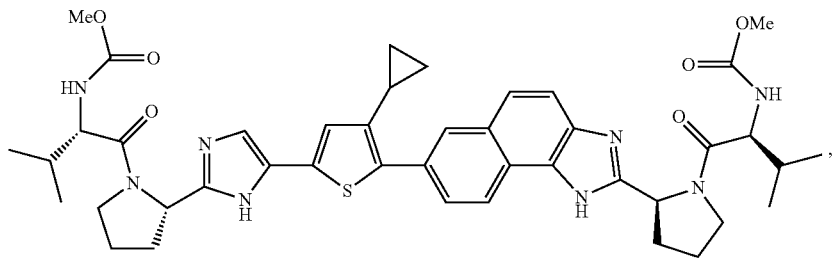
28
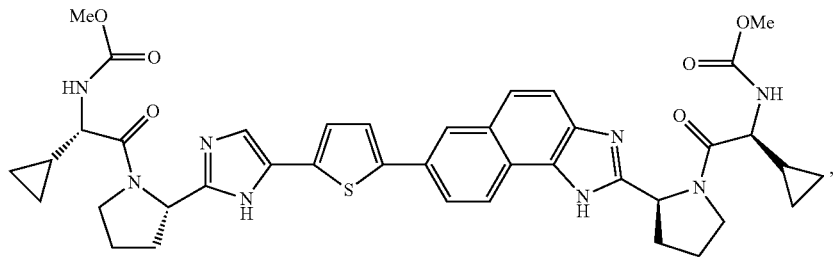
29
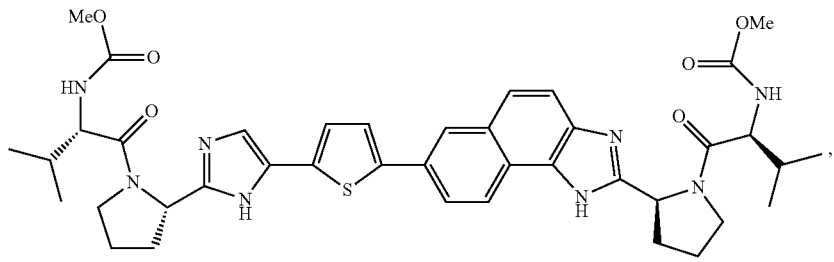
30
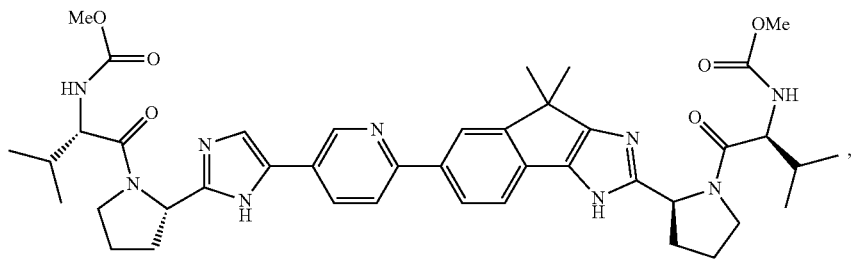
31
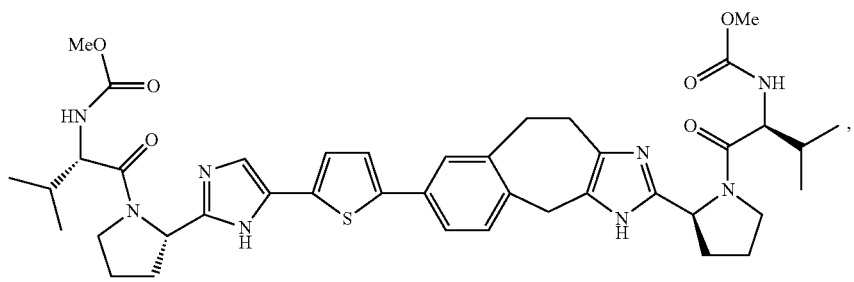

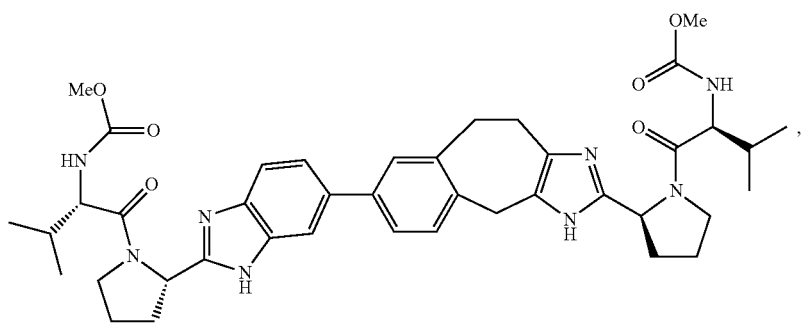
32
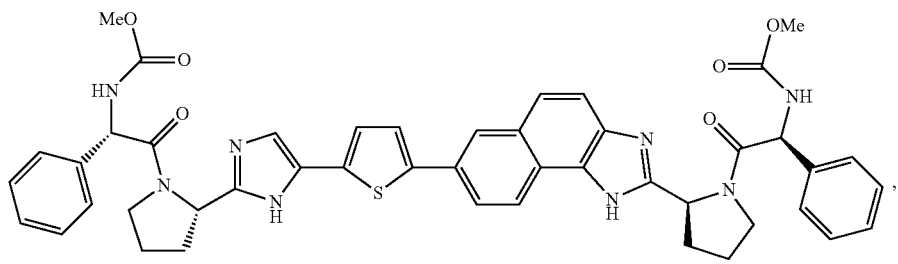
33
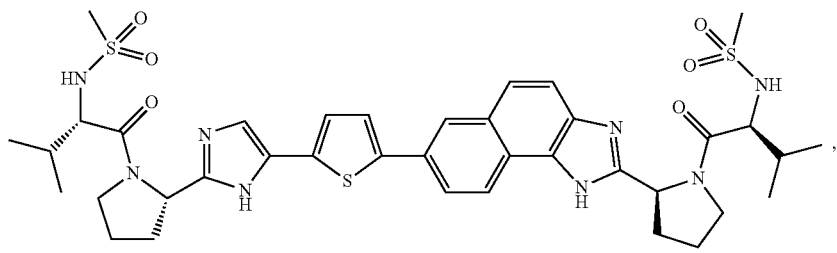
34
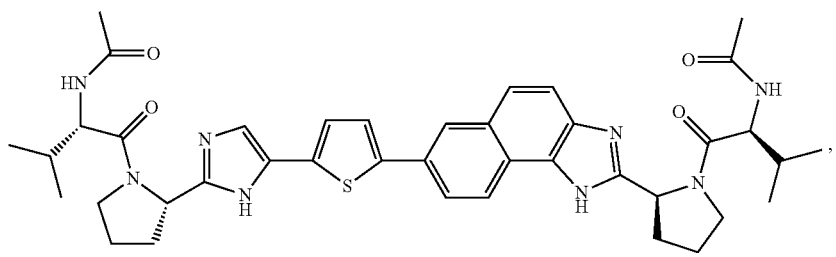
35
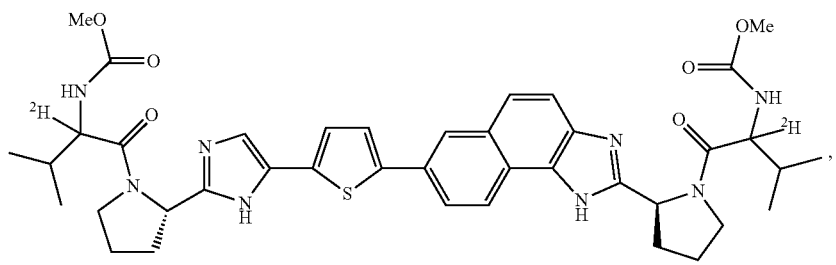
36
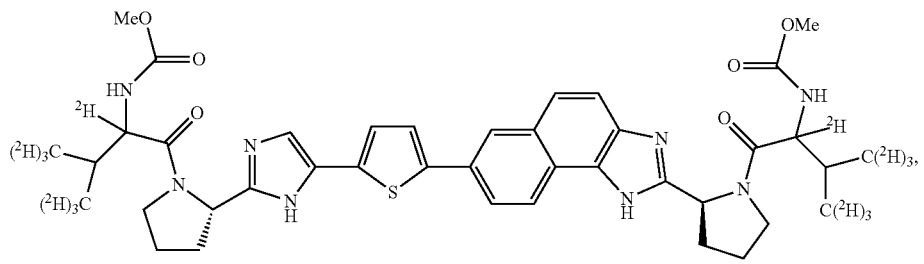
37

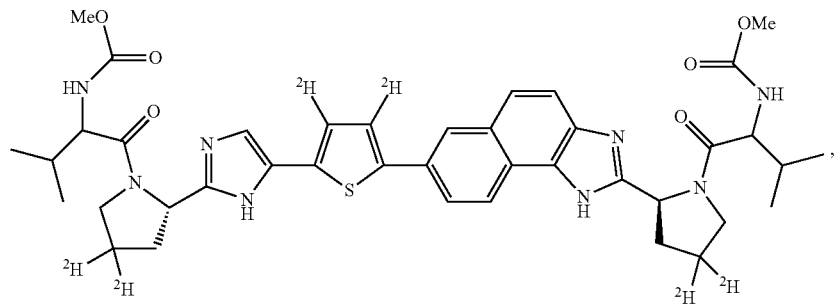
38
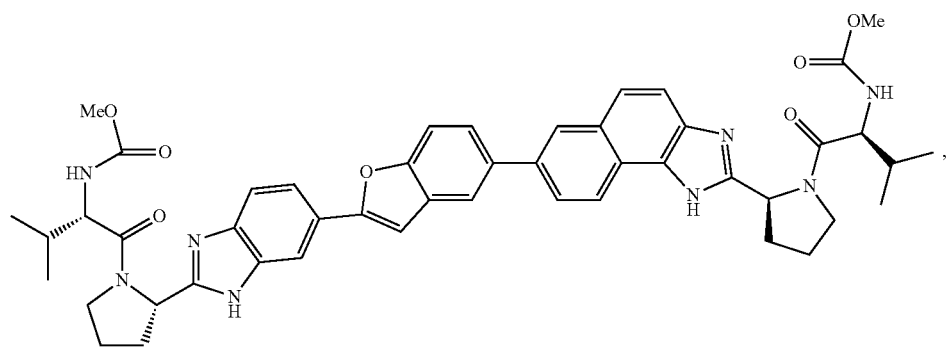
39
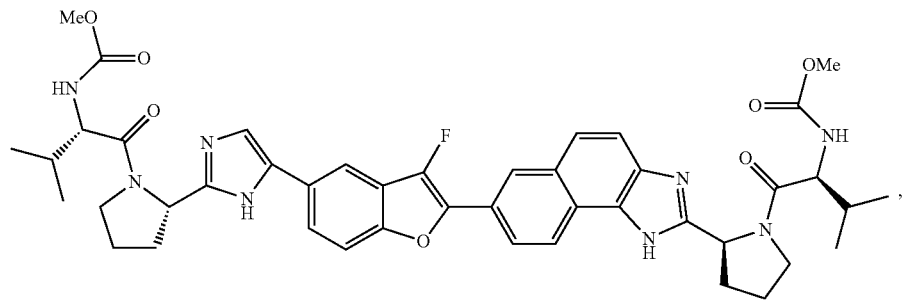
40
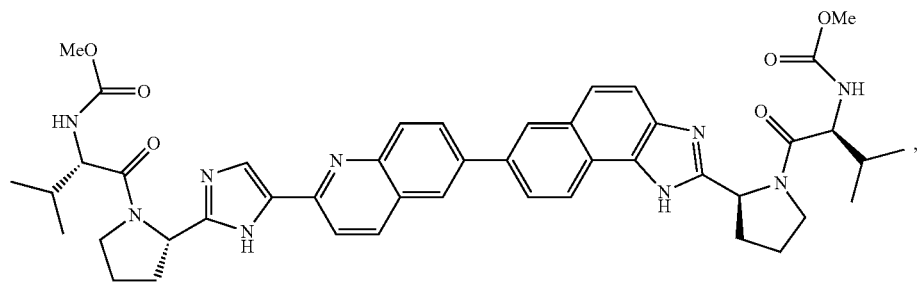
41
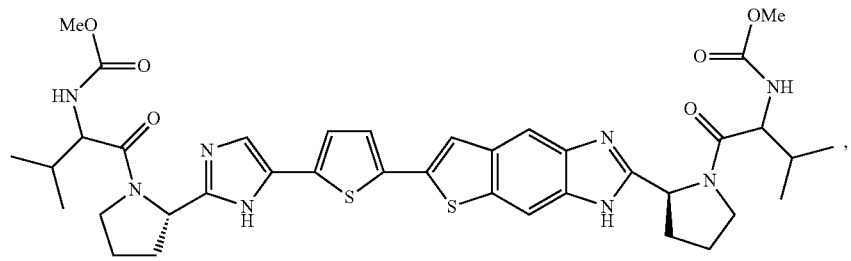
42

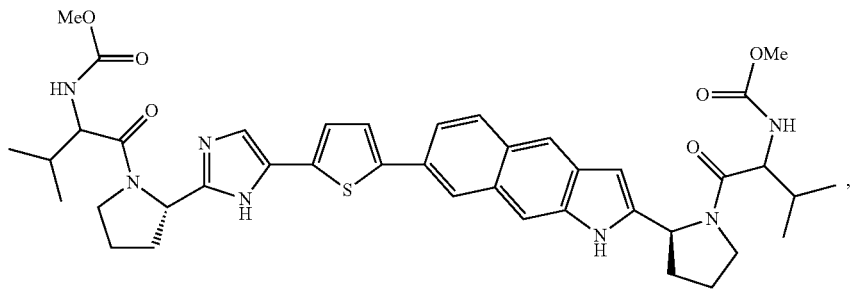

43

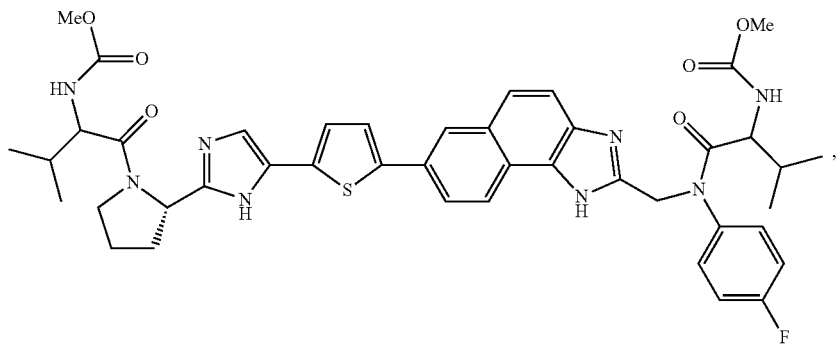

44

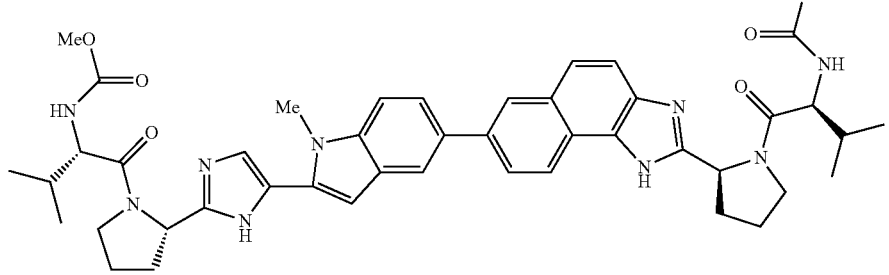

45 and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-8 below. Alternative synthetic -pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available which contain intact fused tricyclic tricyclic ring systems. These starting materials and intermediates are available from commercial suppliers such as Sigma-Aldrich (St. Louis, Mo.) and Acros Organics Co. (Fair Lawn, N.J.). Such starting materials and intermediates compounds are used as received. When such fused tricyclic moieties are not commercially available, they can be prepared using methods well-known to those skilled in the art of organic synthesis. Such synthetic methods include, but are not limited to, those described in Kricka et al., *J Chem.* *Soc. Perkin Trans I,* 859-863 (1973); Kricka et al., *Chem. Rew.,* 74, 101-123, (1974); Kurfuerst et al., *Coll. Czech. Chem. Comm.,* 54, 1705-1715, (1989); Saroja et al., *J. Org. Chem.* 69, 987-990, (2004); Fanta et al., *Synth.* 9-21, (1974), U.S. Patent Publication No. US2005038037; and International Publication No. WO02004039859.

Scheme 1 shows a method useful for making the naphtyl imidazole compounds of formula A7 and A8, which are useful intermediates for making the Compounds of Formula (I).

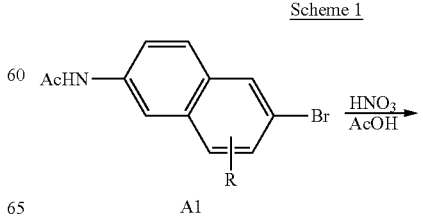

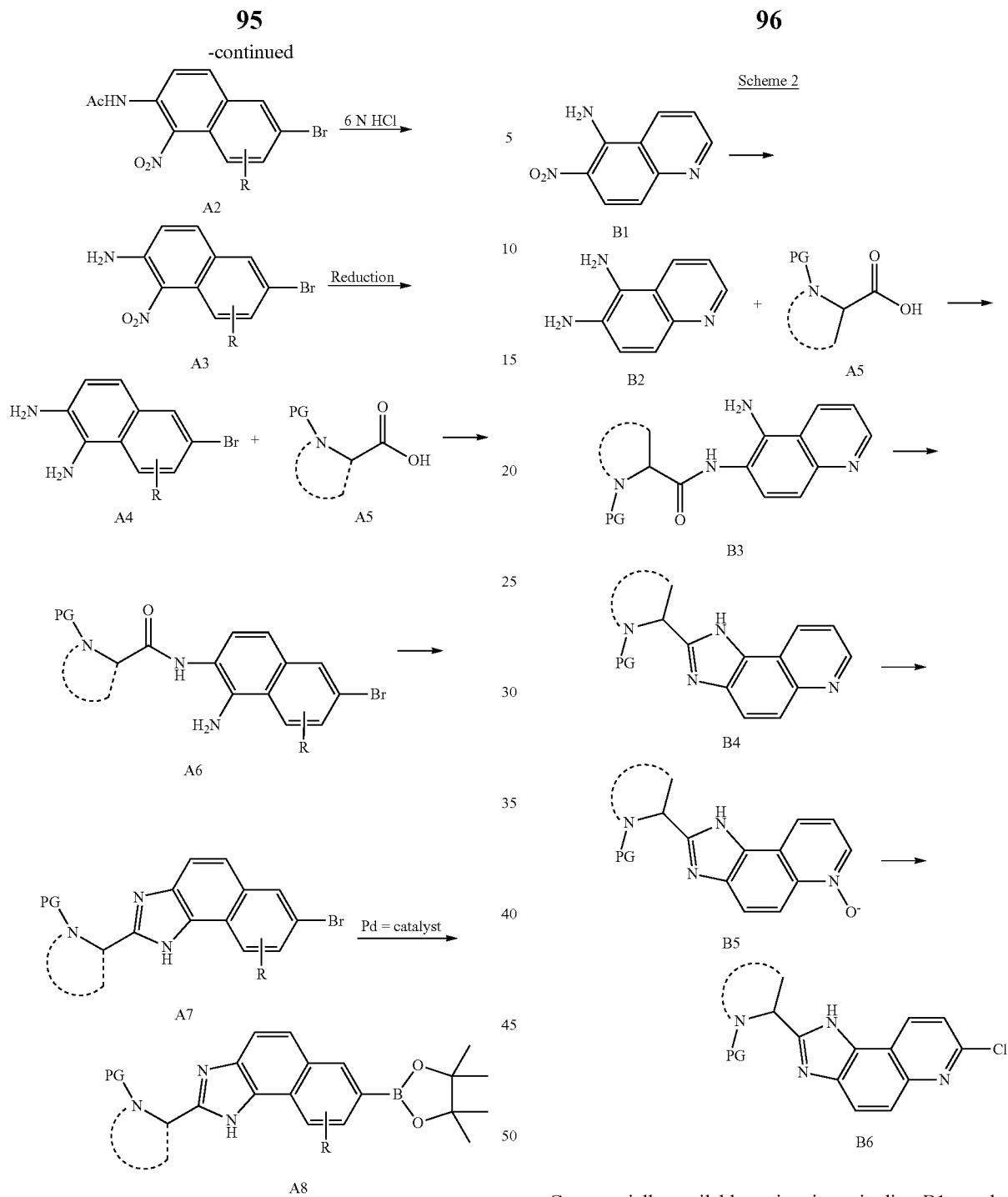

Nitration of bromonaphthal acetamide A1 provides nitro analog A2 (*J. Am. Chem. Soc,* 73:4297 (1997)). The removal of acetyl group under acidic conditions followed by reduction of the nitro group should afford diaminonaphthalene A4. Coupling of the aniline to a cyclic or acyclic N-protected α-amino acid A5 gives an amide of formula A6, which upon heating in acetic acid will cyclize to provide tricyclic bormonaphthalimidazole A7. The bromide could be converted to a boronate A5 with a palladium catalyst.

Scheme 2 shows a method useful for making the quinolineimidazole compounds of formula B6, which are useful intermediates for making the Compounds of Formula (I).

Commercially available aminonitroquinoline B1 can be reduced to diaminoquinoline B2, which is then coupled to a cyclic or acyclic N-protected α-amino acid A5 to providean amide B3. It can then be cyclized to quinolineimidazole B4 under acidic conditions. N-oxide B5 can then be obtained with m-chloroperbenzoic acid. Upon treatment with phosphorous oxychloride, B5 should give the desired chloroquinoline B6, which can used in Suzuki coupling reactions.

Scheme 3 shows a method useful for making the boronic acid compounds of formula C4, which are useful intermediates for making the Compounds of Formula (I), where in "C" is a monocyclic 5 to 6-membered heteroaryl (examples: thiophene or pyridine).

Scheme 3

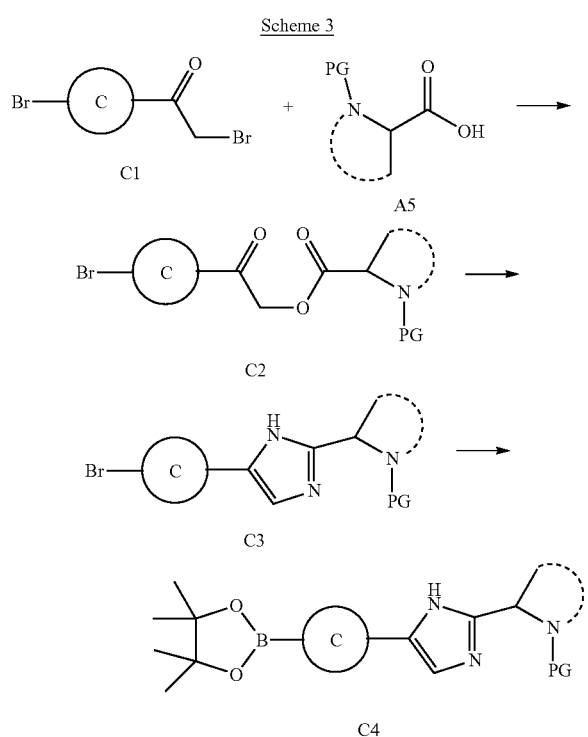

The Suzuki coupling partner C3 or C4 can be prepared from commercially available heteroaryl bromoacetyl compound of formula C1 (Scheme 3). When treated with an N-protected amino acid (PG-AA-OH) in the presence of an amine base, e.g., DIPEA, a ketoester C2 is formed. If heated together with ammonium acetate, the ketoester is converted to the desired imidazole derivative C3. The bromide can then be converted to a boronate C4 with a palladium catalyzed reaction.

Scheme 4 shows methods useful for making the compounds of formula C1 and C3, which are useful intermediates for making the Compounds of Formula (I), wherein variable C is other than a bond and B is an imidazole ring.

Scheme 4

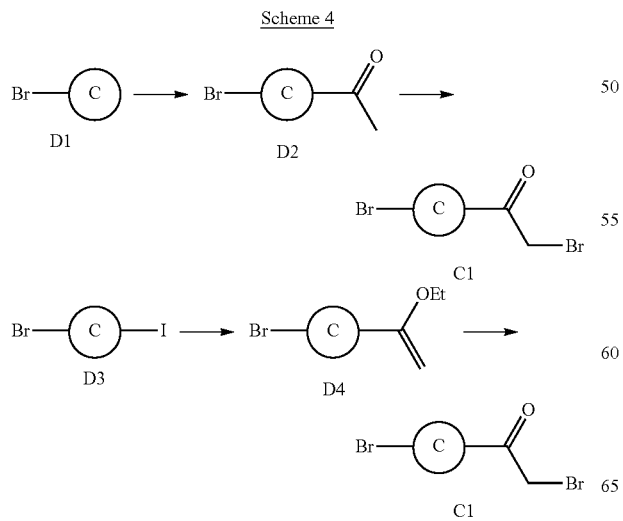

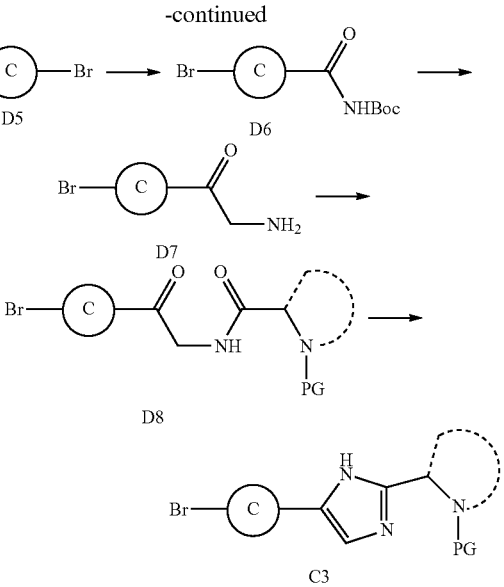

When heteroaryl bromoacetyl C1 is not commercially available, it can be prepared by performing Friedel-Crafts acylation on a heteroaryl bromide of formula D1 using well-known methods, (e.g., those described in Kricka et al., *J. Chem. Soc. Perkin Trans I,* 859-863 (1973), and Kricka et al, *Chem. Rew.,* 74, 101-123, (1974)) to provide the acylated products of formula D2. A compound of formula D2 can then be brominated using bromine, for example, to provide the compounds of formula C1.

On the other hand, bromo-iodo substituted heteroaromatic rings D3 can undergo a Stille coupling with (□-ethoxyvinyl) tributylstannane in the presence of a palladium catalyst using the methods including, but not limited to those described in Choshi et a., *J. Org. Chem.,* 62:2535-2543 (1997), and Scott et al., *J. Am. Chem. Soc.,* 106:4630 (1984)), to provide the ethyl-vinyl ether intermediate D4. Treating D4 with N-bromosuccimide gives the desired bromoacetyl intermediate C1, which can then be elaborated to advanced intermediates C3 or C4 for Suzuki coupling.

Alternatively, a heteroaromatic dibromide of formula D5 can be lithiated using n-butyl lithium and then quenched with N-Boc-glycine Weinreb amide to provide a Boc-protected □-keto amino compound of formula D6. Removal of the Boc group using TFA, for example, provides an amine compound of formula D7, which can-then be coupled with an N-protected amino acid using typical amide bond forming reagents such as HATU to provide a ketoamide compound of formula D8. Upon heated in the presence of ammonium acetate, compound D8 can be cyclized to the imidazole analog of formula C3.

Scheme 5 shows a method useful for making the boronic acid compounds of formula E4, which are useful intermediates for making the Compounds of Formula (I).

Scheme 5

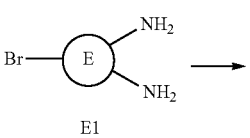

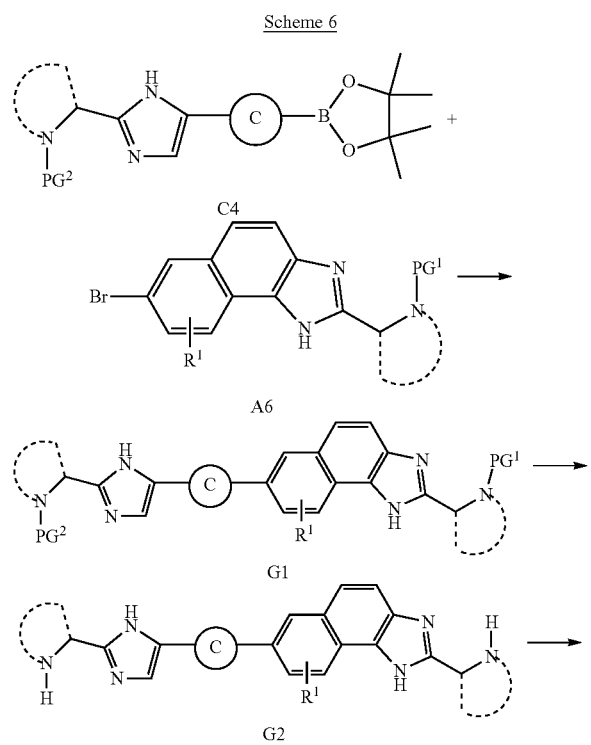

A heteroaromatic diamine E1 could be converted to a bicyclic imidazole E3 using the two step coupling-cyclization procedure described, for example, in Scheme 3. The corresponding boronate E4 can then easily be obtained from bromide E3 via well-known chemistry. Both E3 and E4 can be used as intermediate coupling partners in a Suzuki coupling process to provide the Compound of Formula (I).

Scheme 6 shows methods useful for making the Compounds of Formula (I) via a Suzuki Coupling process.

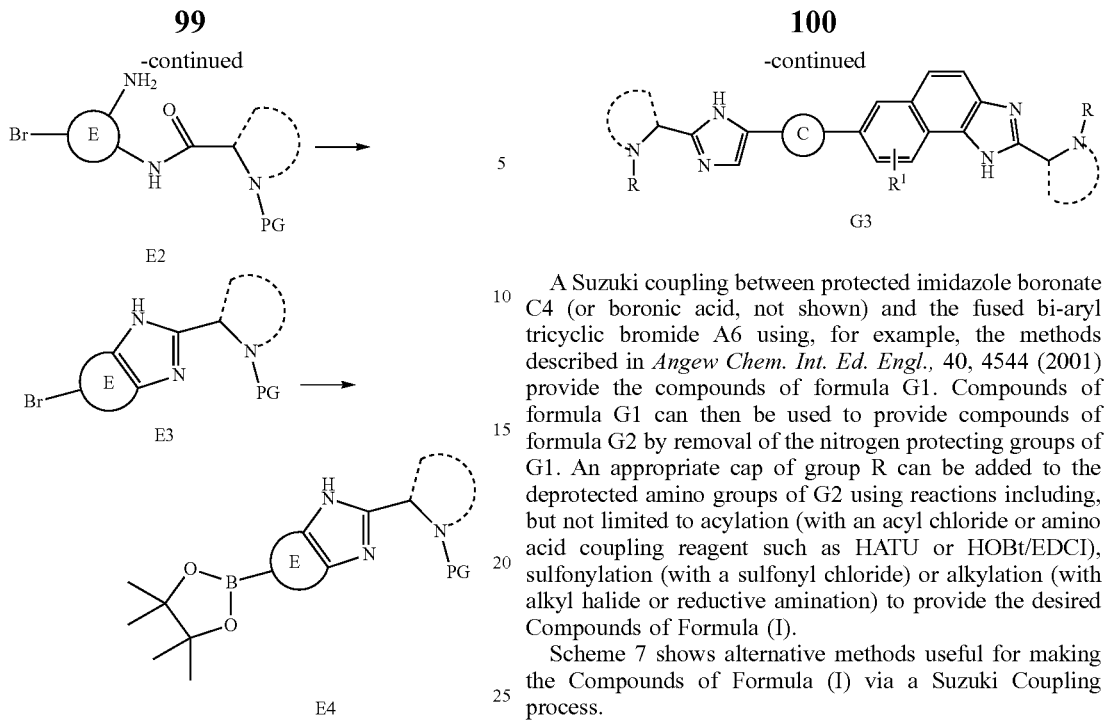

A Suzuki coupling between protected imidazole boronate C4 (or boronic acid, not shown) and the fused bi-aryl tricyclic bromide A6 using, for example, the methods described in *Angew Chem. Int. Ed. Engl.*, 40, 4544 (2001) provide the compounds of formula G1. Compounds of formula G1 can then be used to provide compounds of formula G2 by removal of the nitrogen protecting groups of G1. An appropriate cap of group R can be added to the deprotected amino groups of G2 using reactions including, but not limited to acylation (with an acyl chloride or amino acid coupling reagent such as HATU or HOBt/EDCI), sulfonylation (with a sulfonyl chloride) or alkylation (with alkyl halide or reductive amination) to provide the desired Compounds of Formula (I).

Scheme 7 shows alternative methods useful for making the Compounds of Formula (I) via a Suzuki Coupling process.

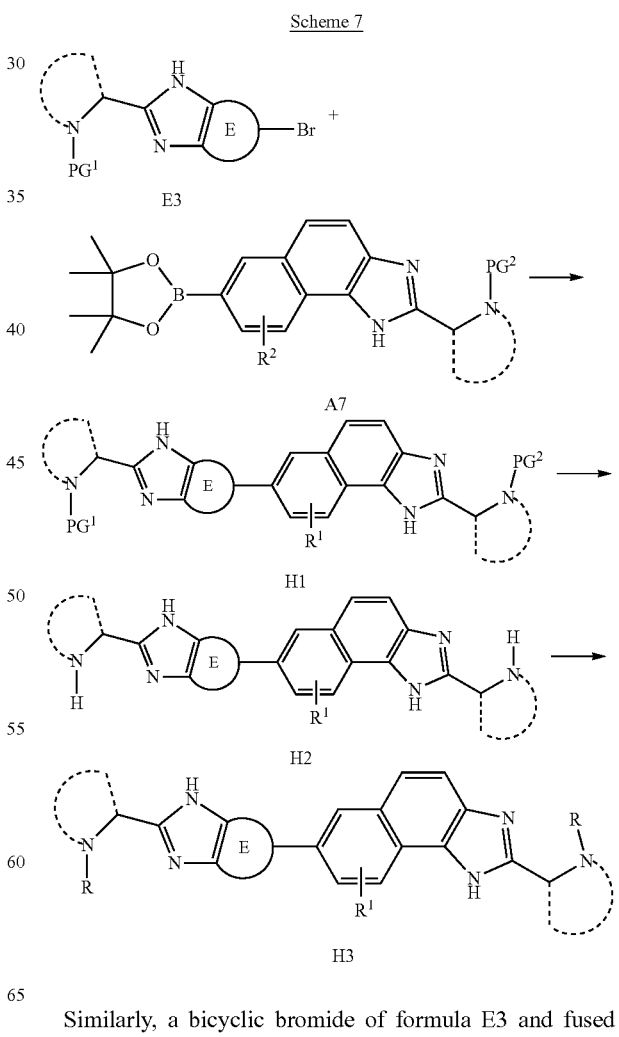

Similarly, a bicyclic bromide of formula E3 and fused tricyclic-boronate of formula A7 can be joined using the methods described in Scheme 6 above, to provide coupled-intermediates of formula H1. The compounds of formula H1 can then be further elaborated using, for example, the methods described in Scheme 6 above, to provide the Compounds of Formula (I), wherein C is a bond and B is a bicyclic heteroarylene group.

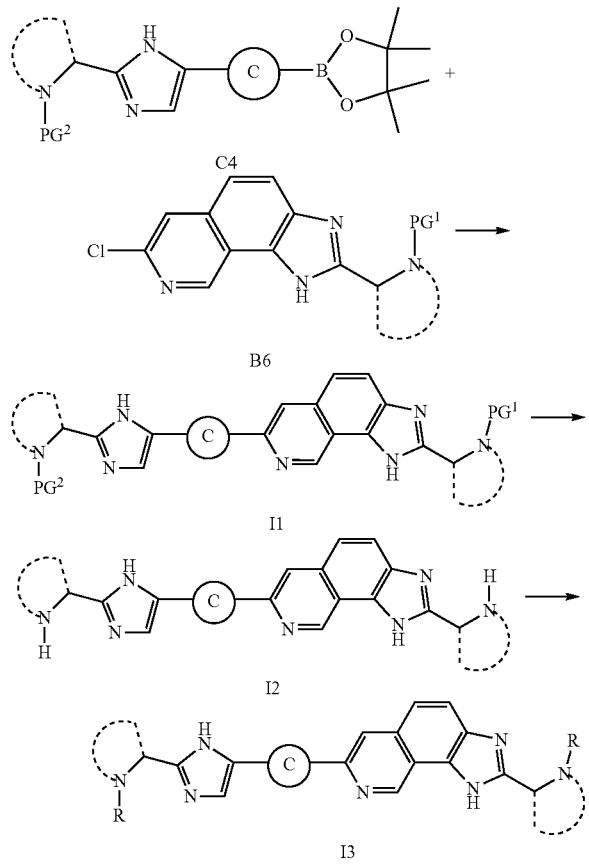

A boronate of formula C4 and chloroquinolineimidazole of formula B6 can be coupled under Suzuki coupling conditions similar to the methods described above to provide products of formula I1, which can be transformed to the final targets of formula I3, using methods well-known to those skilled in the art of organic synthesis, including those described in Scheme 6 above.

In some of bicyclic and fused tricyclic compounds contemplated in Schemes 1-8, the amino acids (such as, but not limited to proline, 4,4-difluoroproline, (S)-2-piperidine carboxylic acid, valine, alanine, norvaline, etc.) are incorporated as part of structures. Methods have been described in the general literature as well as in Banchard US 2009/0068140 (Published Mar. 9th 2009) for the preparation of such amino acid-derived intermediates.

One skilled in the art of organic synthesis will recognize that the synthesis of fused tricyclic cores in Formula (I) may require protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

One skilled in the art of organic synthesis will also recognize that one route for the synthesis of fused bi-aryl tricyclic cores in Formula (I) may be more desirable depending on the choice of appendage substituents. Additionally, one skilled in the art will recognize that in some cases the order of reactions may differ from that presented herein to avoid functional group incompatibilities and can amend the synthetic route accordingly.

One skilled in the art of organic synthesis will recognize that the synthesis of certain fused tricyclic cores in Formula (I) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g., HOBt; EDCI, DCC, HATU, PyBrop) with an amine.

The preparation of ring systems contemplated in this invention have been described in the literature and in compendia such as "Comprehensive Heterocyclic Chemistry" editions I, II and III, published by Elsevier and edited by A. R. Katritzky & R J K Taylor. Manipulation of the required substitution patterns have also been described in the available chemical literature as summarized in compendia such as "Comprehensive Organic Chemistry" published by Elsevier and edited by DH R. Barton and W. D. Ollis; "Comprehensive Organic Functional Group Transformations" edited by edited by A. R. Katritzky & R J K Taylor and "Comprehensive Organic Transformation" published by Wily-CVH and edited by R. C. Larock.

The starting materials used and the intermediates prepared using the methods set forth in the Schemes above may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 5-7 min—95% CH$_3$CN, 7 min—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound Int-1

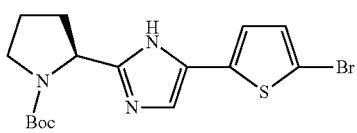

Int-1

Step A—Synthesis of Compound Int-1a

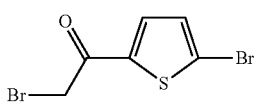

Int-1a

To a solution of 2-acetyl-5-bromothiophene (10.0 g, 48.8 mmol) in anhydrous $CH_2Cl_2$ (120 mL) at room temperature was added bromine (7.79 g, 48.8 mmol). The resulting reaction was allowed to stir at room temperature for 20 hours, then was concentrated in vacuo to provide Compound Int-1a as a yellow solid (14.0 g, quant.), which was used without further purification.

Step B—Synthesis of Compound Int-1b

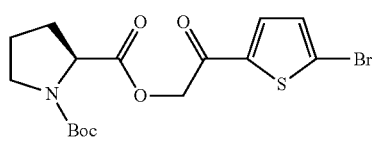

Int-1b

To a solution of Compound Int-1a (13.9 g, 48.8 mmol) and N-Boc-proline (22.1 g, 103 mmol) in anhydrous acetonitrile (250 mL) at room temperature was added diisopropylethylamine (18.0 mL, 101 mmol). The reaction was allowed to stir at room temperature for 16 hours, then EtOAc (500 mL) and water (500 mL) were added and the layers separated. The organic solution was washed with saturated aqueous sodium bicarbonate solution (500 mL), dried over $MgSO_4$, filtered and concentrated in vacuo to provide Compound Int-b (21.2 g, quant.), which was used without further purification.

Step C—Synthesis of Compound Int-1

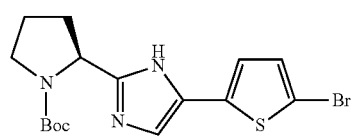

Int-1

A suspension of Compound Int-1b (11.7 g, 28.0 mmol) and $NH_4OAc$ (43 g, 559 mmol) in anhydrous toluene (200 mL) was heated to 100° C. and allowed to stir at this temperature for 12 hours. The reaction mixture was then cooled to room temperature and EtOAc (500 mL) and water (500 mL) were added. The layers were separated and the aqueous layer was extracted with EtOAc (2×200 mL). The combined organic extracts were dried over $MgSO_4$, filtered and concentrated in vacuo. The residue obtained was purified using flash chromatography on an ISCO 330 g Redi-Sep column (10-80% EtOAc/hexanes as eluent) to provide Compound. Int-1 (6.18 g, 56%). LRMS: $(M+H)^+=398.1, 400.1$.

Example 2

Preparation of Compound Int-2

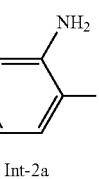

Int-2a

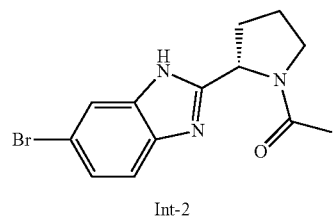

Int-2

To a 0° C. solution of Compound Int-2a (6.1 g, 32.7 mmol), N-acetyl-L-proline (5.4 g, 34.35 mmol) and HATU (13.7 g, 34.35 mmol) in anhydrous DMF (100 mL) was added diisopropylethylamine (16.91 mL, 96.9 mmol) dropwise over 15 minutes. The reaction was allowed to warm to room temperature with stirring for 3 hours. The reaction was then diluted with EtOAc (500 mL) and the organic layer washed with water (200 mL×2). The aqueous layer was back-extracted with EtOAc (100 mL×2) and the combined organic extracts were washed with brine, dried over $MgSO_4$, filtered and concentrated in vacuo. The residue obtained was purified using flash column chromatography on silica gel (1% -2% $MeOH/CH_2Cl_2$) to provide an intermediate amide (4.1 g) which was dissolved in glacial acetic acid and the resulting solution was heated to 70° C. and allowed to stir at this temperature for 1 hour. The reaction mixture was diluted with EtOAc (100 mL), cooled to 0° C. and saturated aqueous $Na_2CO_3$ solution was added slowly until the solution reached pH 8. The organic layer was then separated and the aqueous layer was extracted with EtOAc (250 mL×2). The combined organic layers were washed with water, then brine, dried over $MgSO_4$, filtered and concentrated in vacuo to provide Compound Int-2 (3.75 g, 38%) which was used without further purification. LCMS: $M^+=3018$.

Example 3

Preparation of Compound Int-3

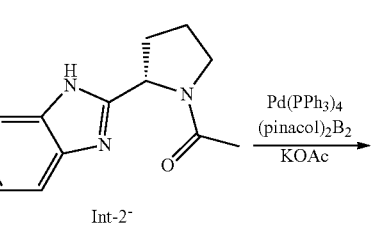

Int-2⁻

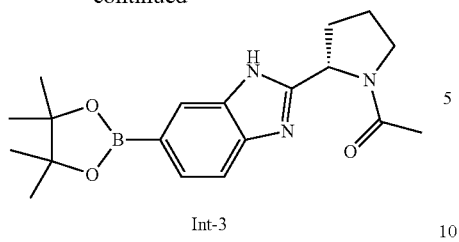

Int-3

Compound Int-2 (925 mg, 3 mmol), bis(pinacolato) diboron (1.6 g, 6.3 mmol), Pd(PPh$_3$)$_4$ (174 mg, 0.15 mmol), potassium acetate (736 mg, 7.5 mmol) and 1,4-dioxane (100 mL) were added to a 350 mL pressure vessel. The resulting mixture was degassed, purged with nitrogen heated to 80° C. and allowed to stir at this temperature for 17 hours. The reaction mixture was then cooled to room temperature, diluted with CH$_2$Cl$_2$ (300 mL) and filtered through a celite plug. The filtrate was washed with saturated aqueous NaHCO$_3$ solution (50 mL) and water (50 mL). The combined organic layers were washed with brine, dried over MgSO$_4$, filtered and concentrated in vacuo and the residue obtained was purified using flash column chromatography on silica gel (0-5% MeOH/CH$_2$Cl$_2$) to provide Compound Int-3 (750 mg, 70%, contains some pinacol impurity). MS: MH$^+$=356.2; $^1$H NMR (500 MHz, CD$_3$OD): δ 8.1-7.4 (m, 3 H), 5.3 (m,1 H), 3.9 (m, 1 H), 3.7 (m, 1H), 2.4 (m, 1 H), 2.0-2.2 (m, 6 H), 1.39 (bs, 12 H).

Example 4

Preparation of Compound Int-4

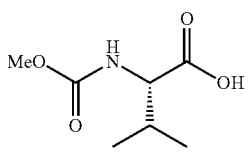

Int-4

To a solution of L-valine (10:0 g, 85.3 mmol) in 1 M aqueous NaOH solution (86 mL) at room temperature was added solid sodium carbonate (4.60 g, 43.4 mmol). The solution was cooled to 0° C. and methyl chloroformate (7.20 mL, 93.6 mmol) was added dropwise over 20 minutes. The reaction was then allowed to warm to room temperature and stirred for 4 hours. The reaction mixture was washed with diethyl ether (100 mL) and aqueous solution was cooled to 0° C. Concentrated hydrochloric acid (18 mL, 216 mmol) was added and the resulting solution was extracted with EtOAc (3×100 mL). The combined organic extracts were dried over MgSO$_4$, filtered and concentrated in vacua to provide Compound Int-4 (13.5 g, 90%), which was used without further purification.

The following intermediates can be prepared by the reaction of L-valine with isopropyl chloroformate, 2-methoxyethyl chloroformate or with 1-methylcyclopropyl hydroxysuccinimide respectively as above.

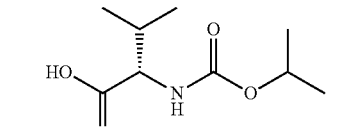

Int-1b

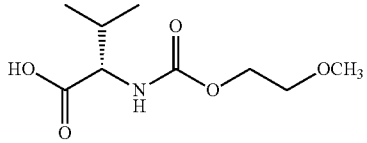

Int-1c

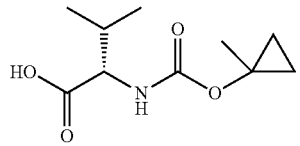

Int-d

Example 5

Preparation of Compound Int-5

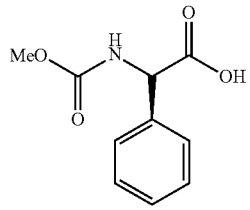

Int-5

To a 0° C. solution of D-phenylglycine (10.0 g, 66.1 mmol) and NaOH (21.2 g, 265 mmol) in water (60 mL) was added methyl chloroformate (10.2 mL, 133 mmol) dropwise over 20 minutes. The resulting reaction was allowed to stir at 0° C. for 1 hour and then acidified with concentrated hydrochloric acid (25 mL, 300 mmol). The acidic solution was extracted with EtOAc (3×100 mL) and the combined organic extracts were dried over MgSO$_4$, filtered and concentrated in vacuo to provide Compound Int-5 (12.6 g, 91%), which was used without farther purification.

Example 6

Preparation of Compound Int-6

Step A—Preparation of Compound Int-8a

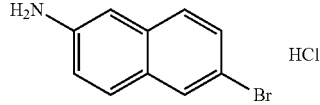

Int-6a

A mixture of 6-bromo-2-naphthoic acid (80.3 g, 319 mmol), diphenylphosphoryl azide (71 mL, 352 mmol) and triethylamine (50 mL, 358 mmol) in tert-butanol (400 mL) was heated to reflux and allowed to stir at this temperature for 15 hours. The reaction mixture was then cooled to room temperature and poured over saturated aqueous NaHCO₃ solution (600 mL) and stirred vigorously for 30 minutes. The resulting suspension was filtered, washed with water (200 mL) and dried in vacuo at 65° C. The resulting white solid was suspended in MeOH (500 mL) and cooled to −78° C., then HCl gas was bubbled into the mixture until saturated. The reaction mixture was then allowed to stir at room temperature for 15 hours, after which time the resulting solids were collected by filtration, then washed with ice-cold MeOH (100 mL) to provide Compound Int-6a as an off-white solid (74.8 g, 91%), which was used without further purification. ¹H NMR (DMSO-d₆) δ 10.5-10.0 (br s, 3H), 8.23 (s, 1H), 7.99 (d, J=9.0 Hz, 1H), 7.92 (d, J=9.0 Hz, 1H), 7.84 (s, 1H), 7.68-7.65 (m, 1H), 7.56-7.51 (m, 1H), LRMS: (M+2H)⁺=223.

Step B—Preparation of Compound Int-6b

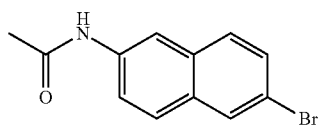

Int-6b

To the solution of Compound Int-6a (74.8 g, 289 mmol) and triethylamine (120 mL, 860 mmol) in CH₂Cl₂ (500 mL) at 0° C. was added acetic anhydride (27.5 mL, 292 mmol). The resulting reaction was warmed to room temperature and stirred at this temperature for 1.5 hours. The reaction mixture was filtered and the filtrate concentrated in vacuo. The resulting residue was triturated with hexanes (500 mL) and the resulting solids were filtered, washed with hexanes (100 mL) and dried in vacuo at 55° C. for 1 hour to provide Compound Int-6b as an off-white solid (60.6 g, 79%), which was used without further purification. ¹H NMR (DMSO-d₆) δ 10.1 (s, 1H), 8.30 (s, 1H), 8.09 (s, 1H), 7.85-7.76 (m, 2H), 7.62-7.53 (m, 2H), 2.10 (s, 3H). LRMS: (M+H)⁺=265.

Step C—Preparation of Compound Int-6c

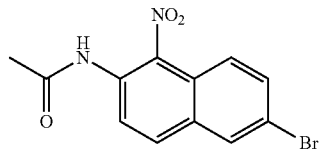

Int-6c

To a solution of Compound Int-6b (60.6 g, 229 mmol) and acetic anhydride (120 mL) in acetic acid (500 mL) at 0° C. was added a solution of fuming nitric acid (36 mL) in AcOH (84 mL) dropwise over 2 hours. The resulting reaction was warmed to room temperature and stirred vigorously at this temperature for 4.5 hours. The reaction mixture was filtered and the collected solids were washed with water (100 mL), then recrystallized from EtOH (1.4 L) to provide Compound Int-6c as an off-white solid (58.5 g, 83%), which was used without further purification. ¹H NMR (DMSO-d₆) δ 8.95 (br s, 1H), 8.46 (d, J=9.0 Hz, 1H), 8.00 (s, 1H), 7.92-7.87 (m, 2H), 7.72-7.67 (m, 1H), 2.28 (s, 3H).

Step D—Preparation of Compound Int-6d

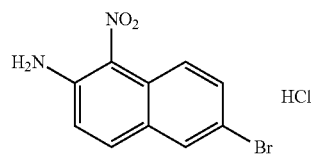

Int-6d

To a solution of Compound Int-6c (58.5 g, 189 mmol) in MeOH (150 mL) was added 6 N HCl (150 mL) and the resulting reaction was heated to 75° C. and allowed to stir at this temperature for 6 hours, then cooled to room temperature. The reaction mixture was filtered and the collected solids were rinsed with water (100 mL) and dried in vacuo at 55° C. for 2 hours to provide Compound Int-6d as a yellow solid (47.9 g, 95%), which was used without further purification. ¹H NMR (DMSO-d₆) δ 8.45 (d, J=9.6 Hz, 1H), 8.09-8.00 (m, 3H), 7.84 (d, J=9.6 Hz, 1H), 7.73-7.67 (m, 1H), 7.21 (d, J=9.6 Hz, 1H), 3.33 (br s, 1H).

Step E—Preparation of Compound Int-6e

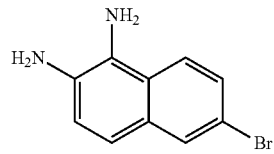

Int-6e

To a solution of Compound Int-6d (47.9 g, 179 mmol) and ammonium chloride (14.4 g, 269 mmol) in water (100 mL) and THF (250 mL) was added iron powder (50 g, 895 mmol). The resulting reaction was heated to 60° C. and allowed to stir vigorously at this temperature for 3 hours, then cooled to room temperature. The reaction mixture was filtered through a Celite pad and rinsed with MeOH until the Celite® was colorless. The combined filtrate and rinsings were concentrated in vacuo and the resulting residue was purified immediately on a silica gel plug (18 cm L×14 cm W) eluting with 1% MeOH/CH₂Cl₂ (7 L) to provide Compound Int-6e as a brown solid (40.5 g, 95%). ¹H NMR (DMSO-d₆) δ 7.85-7.79 (m, 2H), 7.32-7.29 (m, 1H), 7.03-6.96 (min, 2H), 4.86 (br s, 4H). LRMS: (M+H)⁺=238.

Step F—Preparation of Compound Int-6f

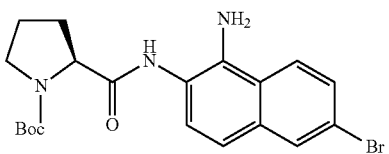

Int-6f

To a solution of Compound Int-6e (40.5 g, 171 mmol), 7-Boc-proline (45.0 g, 209 mmol) and N,N-diisopropylethylaine (90 mL, 517 mmol) in anhydrous DMF (1 L) at 0° C. was added HATU (78 g, 205 mmol). The resulting reaction was warmed to room temperature then stirred at this temperature for 9 hours. Water (1.5 L) was added to the reaction mixture and the resulting solution was extracted with MTBE (3×1.5 L). The combined organic extracts were washed with brine (3×1 L), dried over Na₂SO₄, filtered and concentrated in vacuo. The residue obtained was dissolved in MeOH (75 mL) and water (1.5 L) was added. The resulting heterogeneous mixture was allowed to stir vigorously for 2 hours, then filtered. The filter cake was washed with water (1 L) and dried in vacuo at 55° C. to provide Compound Int-6f as an off-white solid (66.5 g, 90%), which was used without further purification. $^1$H NMR (DMSO-$d_6$) δ 9.45-9.42 (m, 1H), 8.12-8.09 (m, 1H), 8.00 (s, 1H), 7.52-7.47 (m, 1H), 7.36-7.33 (m, 1H), 7.19-7:08 (m, 1H), 5.58 (s, 1H), 5.45 (s, 1H), 4.35-4.21 (m, 1H), 3.45-3.31 (m, 2H), 2.33-2.13 (m, 1H), 2.0-1.75 (m, 3H), 1.46-1.38 (m, 9H).

Step G—Preparation of Compound Int-6

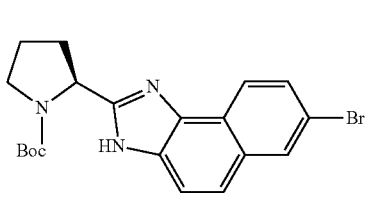

Int-6

A solution of Compound Int-6f (66.5 g, 153 mmol) and AcOH (500 mL) was heated to 60° C. and allowed to stir at this temperature for 1 hour. The reaction mixture was cooled to room temperature, water (1 L) was added and the mixture was adjusted to pH 8 using solid sodium carbonate. The aqueous mixture was extracted with $CH_2Cl_2$ (2×1 L) and the combined organic extracts were dried over $Na_2SO_4$, filtered and concentrated in vacuo to provide Compound Int-6 as a crude brown solid (63.7 g, quant.), which was used without further purification. $^1$H NMR (DMSO-$d_6$) δ 13.0-12.5 (m, 1H), 8.34 (d, J=9.0 Hz, 1H), 8.25-8.23 (m, 1H), 7.78-7.60 (m, 3H), 5.11-4.93 (m, 1H), 3.70-3.56 (m, 1H), 3.51-3.39 (m, 1H), 2.45-2.24 (m, 1H), 2.13-1.85 (m, 3H), 1.49-0.95 (m, 9H). LRMS: (M+H)$^+$=416.

Example 7

Preparation of Compound Int-7

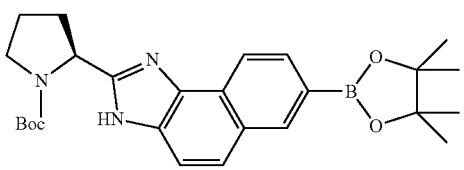

Int-7

To a solution of Compound Int-6 (21 g, 50.4 mmol), bis(pinacolato)diboron (14.1 g, 55.5 mmol) and KOAc (7.5 g, 76.4 mmol) in 1,4-dioxane (20 mL) was added a premixed solution of Pd(dba)$_2$ (1.16 g, 2.01 mmol) and tricyclohexylphosphine (1.14 g, 4.06 mmol) in 1,4-dioxane (10 mL). The resulting reaction was heated to 100° C. and allowed to stir at this temperature for 4 hours, then cooled to room temperature. The reaction mixture was filtered through Celite, and the Celite was rinsed with $CH_2Cl_2$ (100 mL) and the combined filtrate and washing was concentrated in vacuo. The residue obtained was purified using flash chromatography on an ISCO 330 g Redi-Sep column using a gradient of 0-70% EtOAc/hexanes as eluent to provide Compound Int-7 as a yellow solid (19 g, 82%). $^1$H NMR (DMSO-$d_6$) δ 13.0-12.5 (m, 1H), 8.40-8.36 (m, 2H), 7.84-7.63 (m, 3H), 5.13-4.93 (m, 1H), 3.73-3.57 (m, 1H), 3.51-3.41 (m, 1H), 2.44-2.25 (m, 1H), 2.18-1.95 (m, 3H), 1.40-1.02 (m, 21H). LRMS: (M+H)$^+$=464.

Example 8

Preparation of Compound Int-8

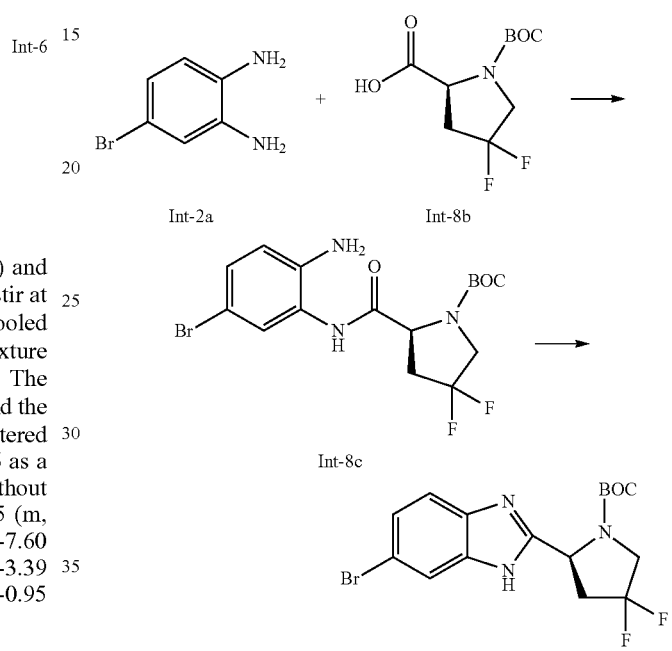

Step A—Synthesis of Compound Int-8c

A solution of Compound Int-2a (7.35 g, 39.3 mmol), Compound Int-8b (9.88 g, 39.3 mmol) and diisopropylethylamine (10 mL, 57.5 mmol) in DMF (40 mL) was cooled to 0° C. HATU (15.0 g, 39.45 mmol) was added slowly, then the reaction mixture was allowed to warm to room temperature and stirred for 19 hours. The reaction mixture was then diluted with ethyl acetate (300 mL) and washed with brine (3×100 mL), and the organic phase was dried over sodium sulfate, filtered and concentrated in vacuo. The residure obtained was purified using a 330 g ISCO silica column (0-5% methanol in dichloromethane as eluent) to provide Compound Int-8c as a brown gel (15:1 g, 91%).

Step B—Synthesis of Compound Int-8

Compound Int-8c (15.1 g, 35.9 mmol) was dissolved in acetic acid (50 mL) in a 500 mL flask. The resulting solution was heated to 60° C. and allowed to stir at this temperature for 4 hours, then cooled to room temperature and concentrated in vacuo. The resulting residue was dissolved in dichloromethane (200 mL), dried (sodium sulfate and sodium carbonate), filtered and concentrated in vacuo to provide Compound Int-8 as a brown solid (11.0 g, 76%), which was used without further purification. LCMS anal. calcd. for: $C_{16}H_{18}BrF_2N_3O_2$ 401.1. Found: 402.2 (M+H)$^+$.

Example 9

Preparation of Compound Int-9

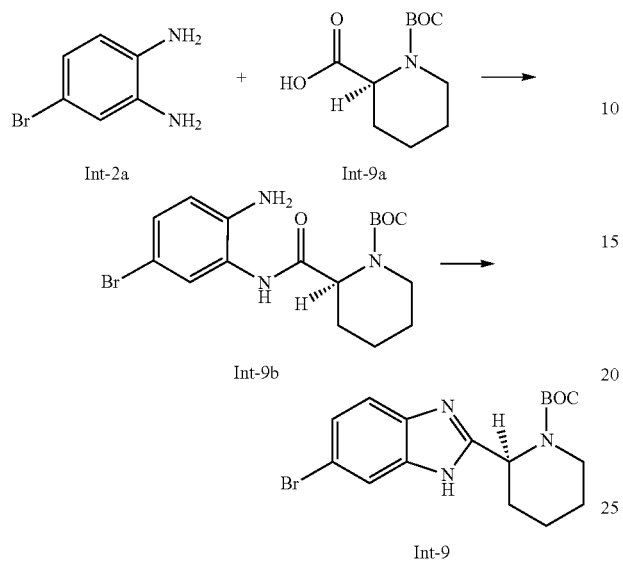

Step A—Synthesis of Compound Int-9b

Using the method described in Example 8, Step A, Compounds Int-2a and Int-9a were coupled to provide Compound Int-9b as a brown gel (12.5 g, 81%).

Step B—Synthesis of Compound Int-9

Using the method described in Example 8, Step B, Compound Int-9a was converted to Compound Int-9 as a brown solid (11.20 g, 93%), which was used without purification.

Example 10

Preparation of Compound Int-10

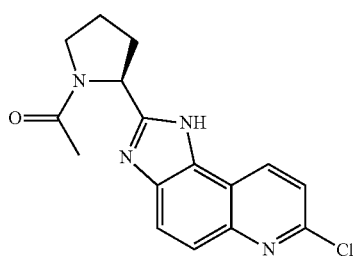

Step A—Synthesis of Compound Int-10a

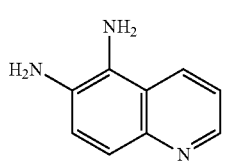

To a solution of 50% palladium on carbon (10% wet, 250 mg) in absolute ethanol (100 mL) under nitrogen atmosphere, was added 5-amino-6-nitroquinoline (5.00 g, 26.4 mmol). With stirring, the solution was placed in vacuo for 30 seconds and then was put under $H_2$ atmosphere using a hydrogen gas-filled balloon. The reaction was allowed to stir for 2 hours, then the reaction flask was evacuated in vacuo and placed under nitrogen atmosphere. The reaction mixture was then sonicated for 10 minutes and methanol (50 mL) was added. The resulting solution was then placed under $H_2$ atmosphere again and allowed to stir for 2 hours. After evacuating the flask of hydrogen, the reaction mixture was filtered through a Celite pad and the pad was washed with methanol (2×200 mL). The combined filtrate and washings were concentrated in vacua and the resulting residue was dissolved in $CH_2Cl_2$ (75 mL). The resulting solution was purified using an ISCO 330-g Redi-Sep column (0-10% methanol/$CH_2Cl_2$ as eluent) to provide Compound Int-10a as a yellow solid (3.76 g, 89%).

Step B—Synthesis of Compound Int-10b

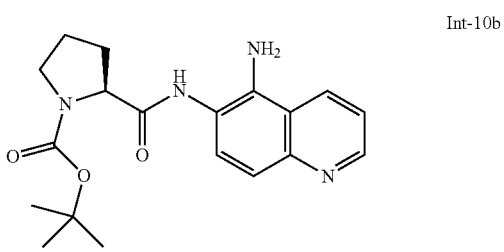 [SMILES: CC(C)(C)OC(=O)N1CCC[C@H]1C(=O)Nc1ccc2ncccc2c1N]

To a solution of Compound Int-10a (1.00 g, 6.28 mmol), HATU (2.63 g, 6.91 mmol) and N,N-diisopropylethylamine (3.28 mL, 18.8 mmol) in anhydrous DMF (20 mL) was added Boo-Pro-OH (1.49 g, 6.91 mmol). The resulting reaction was placed under nitrogen atmosphere and was allowed to stir at room temperature for 17 hours. The reaction mixture was then partitioned between EtOAc (100 mL) and saturated aqueous NaCl solution (100 mL). The aqueous layer was extracted with EtOAc (4×100 mL) and the combined organic extracts were washed with brine (4×100 mL). The resulting solution was dried over $Na_2SO_4$, filtered and concentrated in vacuo. The resulting residue was dissolved in $CH_2Cl_2$ (10 mL) and was purified via chromatography using an ISCO 80-g Redi-Sep column (0-5% methanol/$CH_2Cl_2$ as eluent) to provide Compound Int-10b as an orange oil (0.713 g, 32%). ESI-LRMS: (M+H—$C_4H_9O_2)^+$=257.

Step C—Synthesis of Compound Int-10c

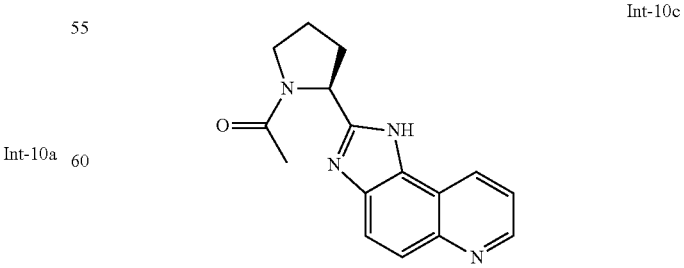

A solution of compound Int-10b (3.00 g, 8.41 mmol) in $CH_3COOH$ (70 mL) was places under nitrogen atmosphere, heated to reflux and allowed to stir at this temperature for 18 hours. The reaction mixture was cooled to room temperature, then was concentrated in vacuo. The oily residue obtained was diluted with CH$_2$Cl$_2$ and the solution was neutralized using saturated aqueous NaHCO$_3$ solution (125 mL). The resulting biphasic mixture was allowed to stir for 1 hour and then separated. The aqueous layer was extracted with CH$_2$Cl$_2$ (2×200 mL) and the combined organic extracts were concentrated in vacuo to provide Int-10c as an orange foam (2.04 g, 86%), which was used without further purification. $^1$H NMR (CDCl$_3$) δ 11.61 (br s, 0.32H), 11.04 (br s, 0.68H); 8:93-8.85 (m, 1.68 H), 8.38-8.30 (m, 0.32H), 8.08-7.70 (m, 2H), 7.53-7.40 (m, 1H), 5.51-5.43 (m, 1H), 3:64-3.51 (m, 2H), 3.34-3.13 (m, 1H), 2.51-2.11 (m, 6H). LCMS: (M+H)$^+$=281.

Step D—Synthesis of Compound Int-10d

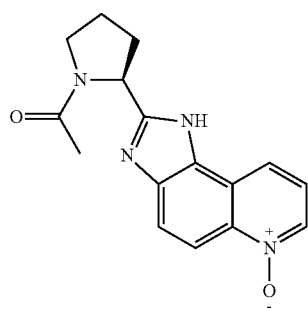

To a 0° C. solution of Compound Int-10c (2.03 g, 7.24 mmol) in C1H$_2$Cl$_2$ (75 mL) under nitrogen, was added 3-chloroperoxybenzoic acid (1.50 g, 8.69 mmol). The resulting reaction was allowed to warm to ambient temperature while stirring for 18 hours, then the reaction mixture was cooled to 0° C. and quenched by adding 10% Na$_2$SO$_3$ solution (25 mL). The organic solvent was removed in vacuo and the remaining aqueous solution was directly purified using an ISCO 80 g Redi-Sep column (0-10% CH$_3$OH/CH$_2$Cl$_2$ as the eluent) to provide a bright yellow foam product. This material underwent a second flash chromatography purification using an ISCO 80 g Redi-Sep column (0-10% CH$_3$OH/CH$_2$Cl$_2$ as the eluent) to provide Compound Int-10d as a light yellow foam (1.85 g, 86%). $^1$H NMR (CDCl$_3$) δ 11.69 (br s, 0.17H), 11.12 (br s, 0.83H), 8.59-8.38 (m, 2.83H), 8.04-7.96 (d, J=9.5 Hz, 0.17H), 7.88-7.81 (d, J=8.2 Hz, 0.17H); 7.75-7.67 (d, J=9.4-Hz, 0.83H), 7.36-7.23 (m, 1H), 5.43-5.34 (m, 1H), 3.56-3.48 (m, 2H), 3.24-3.06 (m, 1H), 2.43-2.06 (m, 6H).

Step E—Synthesis of Compound Int-10

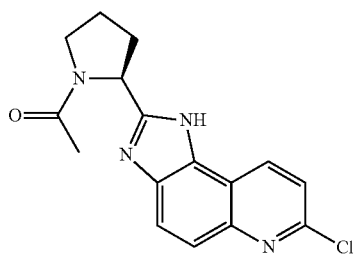

To a 0° C. solution of Compound Int-10d (1.84 g, 6.20 mmol) in CH$_2$Cl$_2$ (20 mL) under nitrogen, was added triethylamine (1.04 mL, 7.45 mmol). The resulting reaction was allowed to stir for 10 minutes, then a solution of phosphoryl chloride (1.14 g, 7.45 mmol) in CH$_2$Cl$_2$ (10 mL) was added dropwise over 10 minutes. The reaction was allowed to stir for an additional 1.75 hours at 0° C. then was quenched by the dropwise addition of water (3.0-mL). The resulting reaction mixture was neutralized to pH 7 using 2N NaOH (~15 mL), then loaded directly onto a 120 g Redi-Sep column and purified using 0-10% CH$_3$OH/CH$_2$Cl$_2$ as the eluent to provide a yellow solid product. The yellow solid product (containing both isomers of Compound Int-10) was then separated into individual isomers using semi-preparative HPLC (Luna C18, CH$_3$CN/water with 0.05% TFA). The isomerically clean fractions were combined with saturated NaHCO$_3$ solution (10 mL) and the organic solvent was removed in vacuo. The remaining aqueous portion was extracted with EtOAc (3×100 mL) and the combined organic extracts were dried over Na$_2$SO$_4$, filtered and concentrated in vacuo. The resulting residue was dissolved in a mixture of CH$_3$CN and water and the solution was freeze-dried overnight to provide Compound Int-10 as an off-white solid (463 mg, 23%). $^1$H NMR (CDCl$_3$) δ 11.10 (br s, 1H), 8.87 (br s, 1H), 7.89-7.68 (m, 2H), 7.53-7.42 (d, J=8.6 Hz, 1H), 5.52-5.40 (d, J=8.0 Hz, 1H), 3.69-3.53 (m, 2H), 3.26 (br s, 1H), 2.52-2.11 (m, 6H).

Example 11

Preparation of Compound Int-11

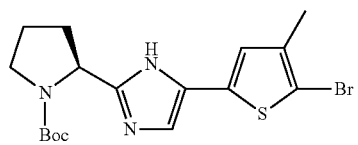

Step A—Synthesis of Compound Int-11a

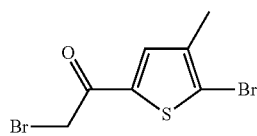

To a solution of 5-bromothiophene-2-carboxylic acid (7.6 g, 34.4 mmol) in anhydrous CH$_2$Cl$_2$ (270 mL) at room temperature was added oxalyl chloride (3.80 mL, 44.5 mmol) dropwise. The resulting reaction was allowed to stir at room temperature for 1.5 hours, then heated to reflux and allowed to stir at this temperature for 1 hour. The reaction mixture was cooled to room temperature, concentrated in vacuo, and the residue obtained was dissolved in anhydrous acetonitrile (180 mL) and cooled to −15° C. (Trimethylsilyl)diazomethane solution in hexane (25.8 mL, 2 M, 51.6 mmol) was added dropwise over 20 minutes and the resulting reaction was allowed to stir at −15° C. for 1 hour. Hydrobromide solution in acetic acid (7.2 mL, 33 wt %, 41.6 mmol) was then added to the cooled reaction mixture dropwise and the resulting reaction was allowed to stir at −15° C. for additional 20 minutes. The reaction mixture was concentrated in vacuo and the residue obtained was dissolved in enthyl acetate (300 mL) and washed with water, saturated aqueous sodium bicarbonate solution and brine (200 mL each). The organic phase was dried over MgSO$_4$, filtered and concentrated in vacuo to provide Compound Int-11a as a light yellow solid (6.5 g, 63%), which was used without further purification.

Step B-C—Synthesis of Compound Int-11

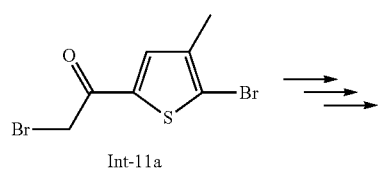
Int-11a

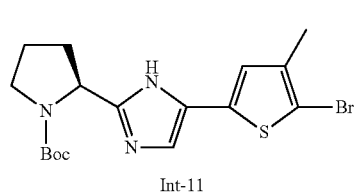
Int-11

Compound Int-11 was synthesized from Int-11a according to the methods described in Example 1, Steps B and C. Int-11a: LRMS: (M+H)$^+$=414.2.

Example 12

Preparation of Compound 1

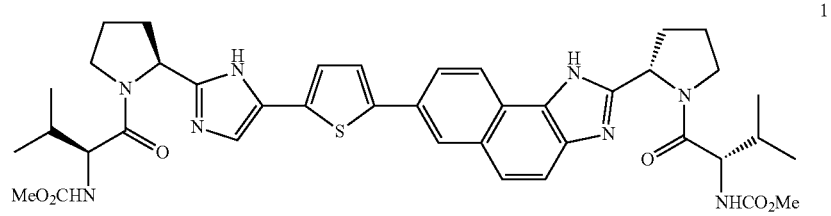
1

Step A—Preparation of Compound 12A

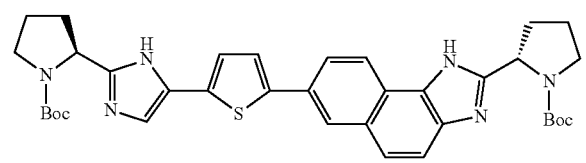
12A

A solution of Compound Int-1 (200 mg), Compound Int-7 (280 mg, 1.2 eq.), Pd(PPh$_3$)$_4$ (702 mg, 0.1 eq.) and Na$_2$CO$_3$ (1.3 g, 2 eq.) in a 2:1 mixture of DME:H$_2$O (5 mL) was heated to 100° C. and allowed to stir at this temperature for 15 hours, then cooled to room temperature. The reaction mixture was diluted with brine (5 mL) and extracted with CH$_2$Cl$_2$ (3×5 mL). The combined organic extracts were dried (Na$_2$SO$_4$), filtered and concentrated in vacuo. The residue obtained was purified using flash chromatography on an ISCO Redi-Sep column using 0-4% MeOH/CH$_2$Cl$_2$ as the eluent to provide Compound 12A as a brown solid (225 mg, 57%). LRMS: (M+H)$^+$=655.5.

Step B—Preparation of Compound 12B

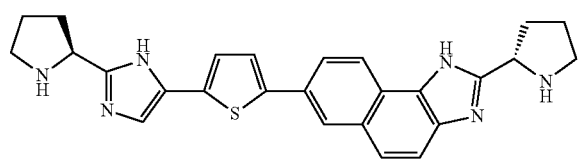
12B

A solution of Compound 12A (220 mg) in TFA (1 mL) and CH$_2$Cl$_2$ (3 mL) was allowed to stir at room temperature for 1.5 hours, then the reaction mixture was concentrated in vacuo. The solid residue obtained was purified using flash chromatography on an ISCO Redi-Sep column (0-20% MeOH/CH$_2$Cl$_2$ with 2% NH$_4$OH as the eluent) to provide Compound 12B as an orange solid (225 mg, quant.). LRMS: (M+H)$^+$=455.3.

Step C—Preparation of Compound 1

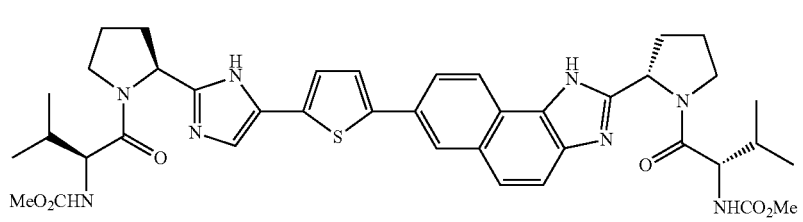

1

A solution of Compound 12B (220 mg), Compound Int-4 (130 mg, 2.5 eq.) and DIPEA (6.1 eq.) in anhydrous DMF (100 mL) was cooled to 0° C. To the cooled solution was added HATU (2.4 eq.) and the resulting reaction was allowed to warm to room temperature on its own and stirred at this temperature for 15 hours. Water (10 mL) was added to the reaction mixture and the resulting solution was extracted with tert-butyl methyl ether (2×10 mL). The combined organic extracts were washed with brine (20 mL), dried over $Na_2SO_4$, filtered and concentrated in vacuo. The resulting residue was purified using flash chromatography on an ISCO Redi-Sep column (0-5% MeOH/$CH_2Cl_2$ as the eluent) and the collected product was lyophilized to provide Compound 1 as a brown solid (110 mg, 43%). LRMS: $(M+H)^+=769.5$.

Example 13

Preparation of Compound 2

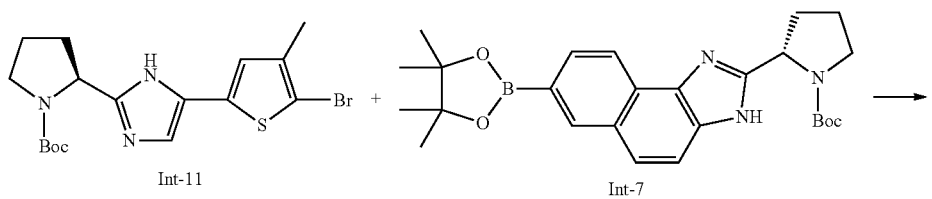

13A

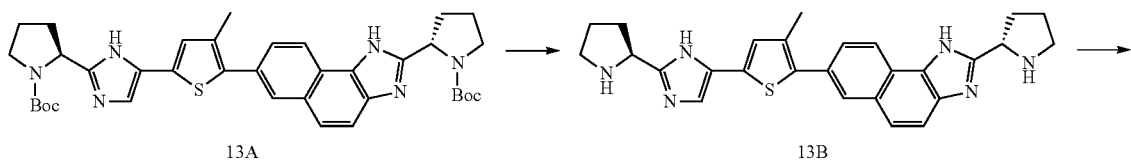

13B

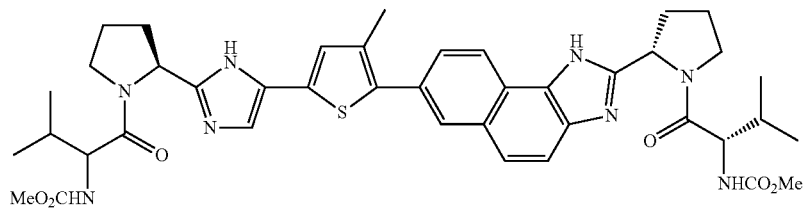

2

Compound 2 was synthesized from Compounds Int-11 and Int-7 using the methods described above in Example 12, Steps A-C. LRMS for compound 2: $(M+H)^+=783.5$.

Example 14

Preparation of Compound 4

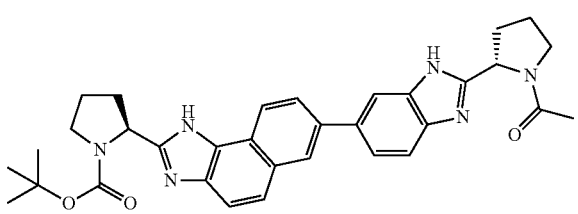

4

Step A—Preparation of Compound 4

To a solution of Compound Int-2 (1.11 g, 3.60 mmol) and Compound Int-7 (2.00 g, 4.32 mmol) in a 2:1 mixture of argon-degassed 1,2-dimethoxyethane:water (30 mL) at room temperature was added tetrakis(triphenylphosphine) palladium(0) (0.417 g, 0.36 mmol) and sodium-carbonate (0.764 mg. 7.20 mmol). The resulting reaction was allowed to stir in a sealed tube at 100° C. for 4 hours, then cooled to room temperature and was poured into a mixture of saturated aqueous sodium chloride solution (50 mL) and CH$_2$Cl$_2$ (50 mL). The aqueous layer was extracted with CH$_2$Cl$_2$ (2×50 mL) and the combined organic extracts were dried over Na$_2$SO$_4$, filtered and concentrated in vacuo. The residue obtained was purfied using an ISCO 120-g Redi-Sep column using 0-5% methanol/CH$_2$Cl$_2$ as the eluent to provide Compound 4 as a yellow solid (0.862 g, 43%). LRMS (M+H)$^+$=565.

Example 15

Preparation of Compound 6

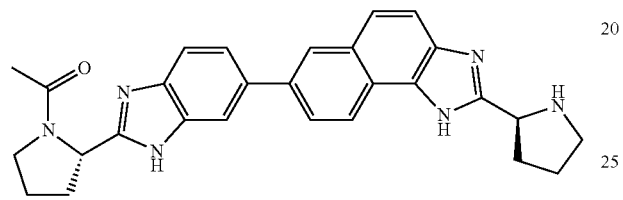

6

To a solution of Compound 4 (0.500 g, 0.88 mmol) in CH$_2$Cl$_2$ (20 mL) was added trifluoroacetic acid (5.92 g, 51.9 mmol). The resulting reaction was allowed to stir at room-temperature for 1 hour, then was concentrated in vacuo to provide Compound 6, which was used without further purification.

Example 16

Preparation of Compound 5

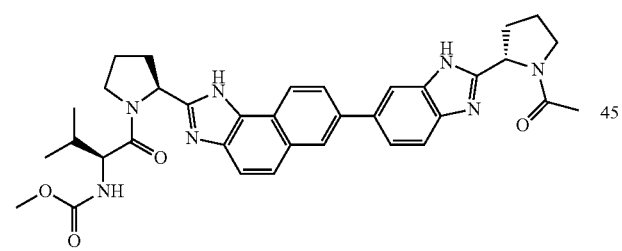

5

To a solution of Compound 6 in DMF (10 mL) was added HATU (0.404 g, 1.06 mmol), followed by Compound Int-4 (0.186 g, 1.06 mmol). The reaction mixture was cooled to 0° C., N,N-diisopropylethylamine (0.801 g, 6.20 mmol) was added, and the reaction was allowed to warm to room temperature on its own, then stirred for an additional 16 hours. The reaction mixture was then poured into a mixture of water (100 mL) and ethyl acetate (100 mL) and the aqueous layer was extracted with CH$_2$Cl$_2$ (2×100 mL). The combined organic extracts were dried-over Na$_2$SO$_4$, filtered and concentration in vacuo to provide a residue which was purified using an ISCO 120-g Redi-Sep column using 0-10% methanol/CH$_2$Cl$_2$ as eluent to provide Compound 5 as a white solid (0.341 g, 62%). $^1$H NMR (CD$_3$OD) δ 9.55 (s, 1H), 8.21. (m, 2H), 7.83 (m, 2H), 7.77-7.50 (m, 4H), 5.32 (m, 2H), 4.53 (s, 1H), 4.26 (m, 1H), 4.15-3.75 (m, 3H), 3.73-3.50 (m, 4H), 2.60-1.89 (m, 8H), 2.18 (s, 3H), 1.00-0.71 (m, 6H). LRMS (M+H)$^+$=622.

Example 17

Preparation of Compound 17

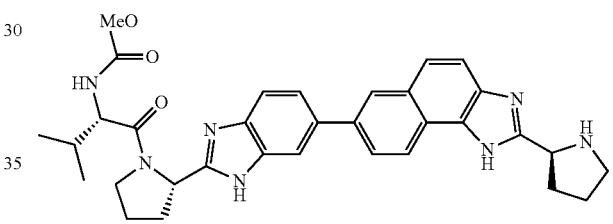

17

A solution of Compound 5 (0.279 g, 0.449 mmol) in 6 N aqueous HCl (5 mL) was heated to 90° C. and allowed to stir at this temperature for 2 hours. The reaction was cooled to room temperature and concentrated in vacuo to provide Compound 17, which was used without further purification.

Example 18

Preparation of Compound 3

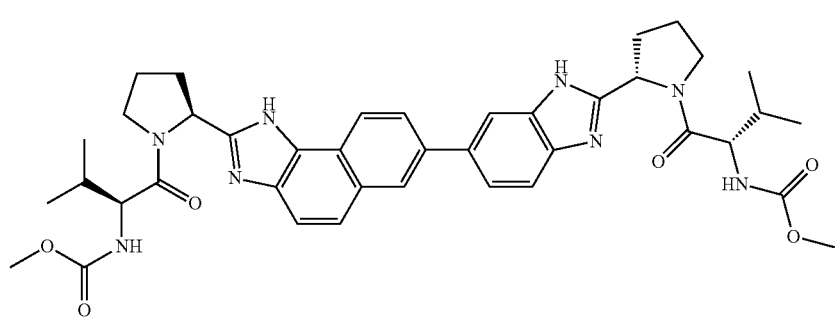

3

To a solution of Compound 17 in DMF (5 mL) was added HATU (0.165 g, 0.434 mmol), followed by (S)-2-(methoxycarbonylamino)-3-methylbutanoic acid (0.076 g, 0.432 mmol). The resulting reaction was cooled to 0° C. and N,N-diisopropylethylamine (0.076 g, 3.60 mmol) was added with vigorous stirring. The reaction was allowed to warm to room temperature, then was stirred at this temperature for 16 hours. Water (100 mL) and EtOAc (100 mL) were added and the resulting solution was extracted with EtOAc (2×50 mL). The combined organic extracts were washed with saturated aqueous NaCl solution (2×150 mL) dried over $Na_2SO_4$, filtered and concentrated in vacuo. The resulting residue was purified using an ISCO 40-g-Redi-Sep column using 0-5% methanol/$CH_2Cl_2$ as the eluent to provide a white solid (0.127 g). This white solid material was then further purified using reverse phase HPLC with 10-100% acetonitrile/water (both with 0.1% TFA). After collection the fractions containing product, the acetonitrile was removed in vacuo and the remaining solution was basified with saturated aqueous sodium bicarbonate solution (20 mL) and extracted with $CH_2C_2$(50 mL). The resulting solution was dried over $Na_2SO_4$, filtered and concentrated in vacuo and the residue obtained was dissolved in $CH_2Cl_2$ (3 mL) and a solution of 4 N HCl in 1,4-dioxane (75 □L) was added. The suspension was allowed to stir for 1 hour at room temperature, then concentrated in vacuo. The resulting residue was dissolved in a 1:1 mixture of acetonitrile:water (5 mL) and the resulting solution was lyophilized for 17 hours to provide Compound 3 as a white solid (104 mg, 29%). $^1$H NMR (DMSO-$d_6$) δ 8.80 (d, J=8.4 Hz, 1H), 8.53 (s, 1H), 8.16 (t, J=7.8 Hz, 3H), 8.09 (d, J=8.7 Hz, 1H), 7.89 (d, J=9.0 Hz, 2H), 7.30 (m, 2H), 5.30 (m, 2H), 4.26-3.70 (m, 6H), 3.55 (s, 6H), 3.69-3.20 (m, 4H), 2.44 (m, 1H), 2.28 (m, 4H), 2.07 (m, 4H), 1.28 (m, 1H), 0.88-0.82 (d, J=6.9 Hz, 6H), 0.79 (m, 6H). LRMS (M+H)$^+$=737.

Example 19

Preparation of Compound 9

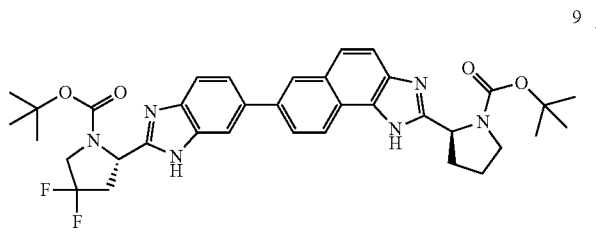

A solution of Compound Int-8 (1.2 g, 2.59 mmol), Compound Int-7 (1.5 g, 3.73 mmol), Pd(dppf)$_2$Cl$_2$ dichloromethane complex (300 mg, 0.363 mmol), aqueous sodium carbonate solution (1.5M, 4.0 mL, 6.0 mmol), and 1,4-dioxane (25 mL) was degassed. The degassed solution was put under nitrogen atmosphere, heated to reflux and allowed to stir at this temperature for 7 hours. The reaction mixture was cooled to room temperature and concentrated in vacuo, and the resulting residue was purified using a 120 g ISCO silica column on Combi-Flash with 0-5%-methanol in dichloromethane as the eluent to provide Compound 9 as a brown solid (870 mg, 51%). LCMS for: $C_{36}H_{40}F_2N_6O_4$ (M+H)$^+$: 659.4.

Example 20

Preparation of Compound 12

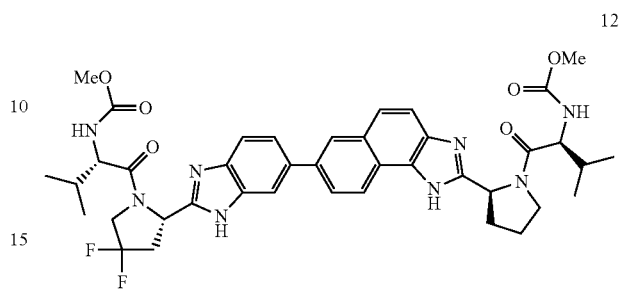

Step A—Preparation of Compound 20A

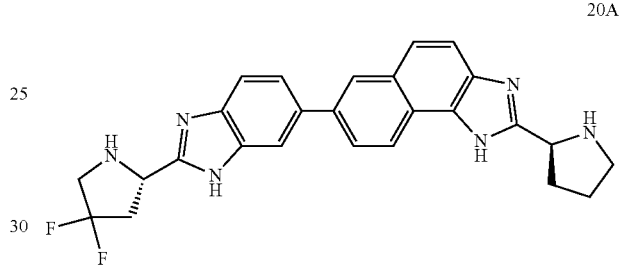

Compound 9 (860 mg, 1.31 mmol) was dissolved in dichloromethane (5 mL) and trifluoroacetic acid (5 mL). The resulting solution was allowed to stir at room temperature for 17 hours and then concentrated in vacuo to provide Compound 20A as a brown solid (750 mg), which was used for the next reaction without purification.

Step B—Preparation of Compound 12

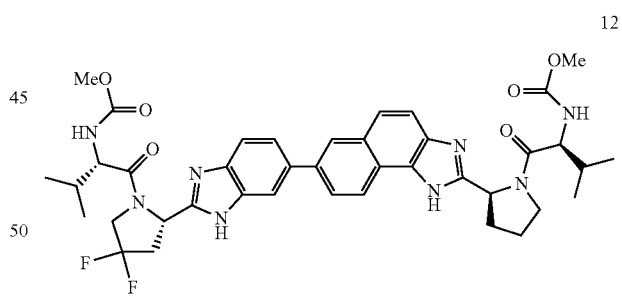

A solution of Compound 20A (360 mg, 0.785 mmol), Compound Int-4 (300 mg, 1.71 mmol), diisopropylethylamine (0.5 mL, 3.74 mmol), HATU (680 mg, 1.78 mmol), and DMF (4 mL) were added to a 100 mL flask at 0° C. The cold bath was removed and the reaction was allowed to stir at room temperature overnight. The reaction mixture was then poured into a mixture of water (10 mL) and ethyl acetate (10 mL) and the aqueous layer was extracted with $CH_2Cl_2$ (2×10 mL). The combined organic extracts were dried over $Na_2SO_4$, filtered and concentration in vacua to provide a residue which was purified using Gilson reverse phase chromatography (0-90% acetonitrile in water with 0.1% TFA as eluent) to provide Compound 12 as a white solid (415 mg, 68%). LCMS for $C_{40}H_{46}F_2N_8O_6$ (M+H)$^+$: 772.4.

Example 21

Preparation of Compound 13

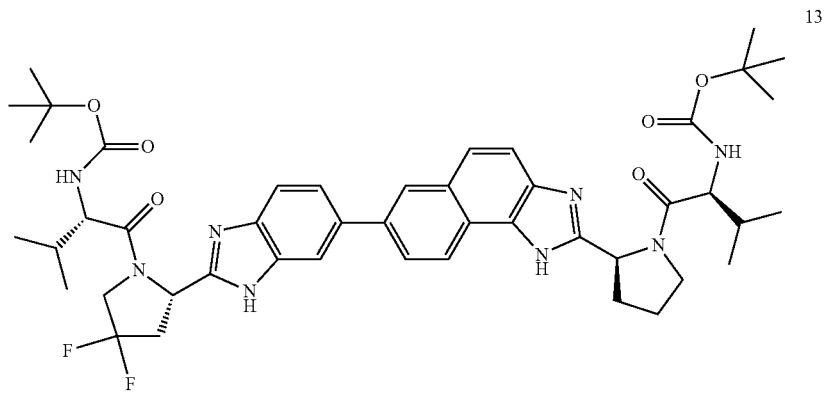 [SMILES: CC(C)[C@H](NC(=O)OC(C)(C)C)C(=O)N1CC(F)(F)C[C@H]1c1nc2ccc(-c3ccc4c(ccc5nc([C@@H]6CCCN6C(=O)[C@@H](NC(=O)OC(C)(C)C)C(C)C)[nH]c54)c3)cc2[nH]1]

Using the method described in Example 21, Compound 20A (190 mg, 0.414 mmol) and L-Boc-valine-OH (220 mg, 1.01 mmol) were coupled to provide Compound 13 as a white solid (180 mg, 51%). LCMS for $C_{46}H_{48}F_2N_8O_6$ (M+H)$^+$: 857.5.

Example 22

Preparation of Compound 14

Compound 13 (140 mg, 0.163 mmol) was dissolved in dichloromethane (4 mL) and trifluoroacetic acid (4 mL) was added. The resulting reaction was allowed to stir at room-temperature for 6 hours, then was concentrated in vacuo. The residue obtained was purified using Gilson reverse phase chromatography (0-90% acetonitrile in water with 0.1% TFA as an eluent) to provide Compound-14 as a white solid (66 mg, 62%). LCMS for $C_{36}H_{42}F_2N_8O_2$ (M+H)$^+$: 657.4.

Example 23

Preparation of Compound 8

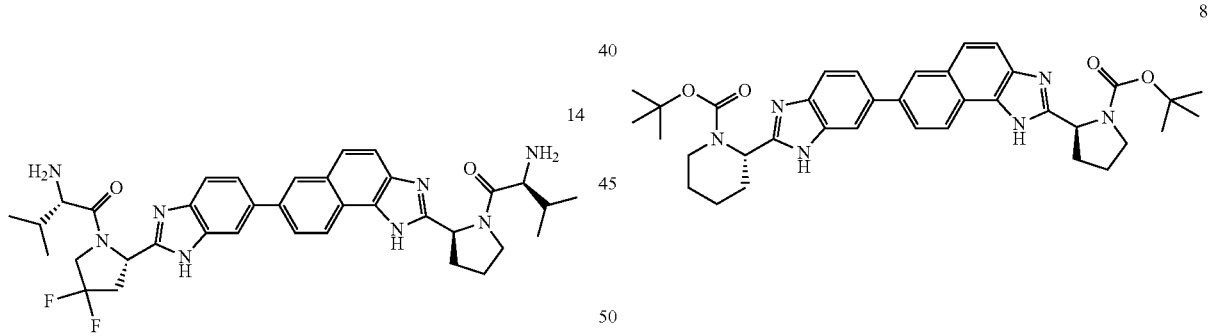

Compound Int-9 (1.2 g, 2.59 mmol), Compound Int-7 (1.4 g, 3.68 mmol), Pd(dppf)$_2$Cl$_2$ dichloromethane complex (300 mg, 03163 mmol), a solution of sodium carbonate (1.5M, 4.0 mL, 6.0 mmol), and 1,4-dioxane (25 mL) was degassed. The degassed solution was placed under nitrogen atmosphere, heated to reflux, and allowed to stir at this temperature for 7 hours. The reaction mixture was cooled to room temperature and concentrated in vacuo, and the residue obtained was purified using a 120 g ISCO silica column on Combi-Flash with 0-5% methanol in dichloromethane as an eluent to provide Compound 8 as a brown solid (980 mg, 59%). LCMS for: $C_{37}H_{44}N_6O_4$ (M+H)$^+$: 637.4.

Example 24

Preparation of Compound 11

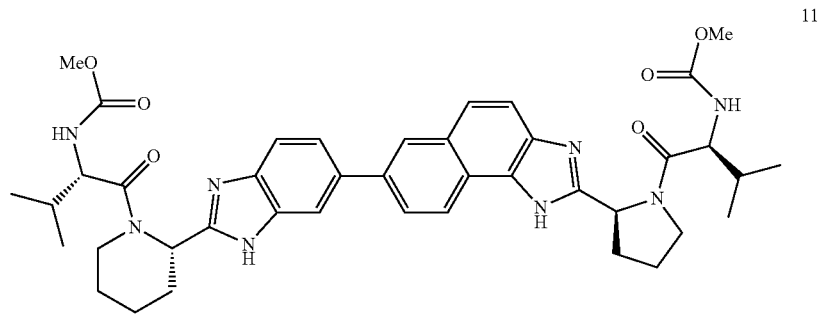 [SMILES: COC(=O)N[C@H](C(=O)N1CCCC[C@H]1c1nc2ccc(-c3ccc4c(ccc5nc([C@@H]6CCCN6C(=O)[C@@H](NC(=O)OC)C(C)C)[nH]c54)c3)cc2[nH]1)C(C)C]

Step A—Preparation of Compound 24A

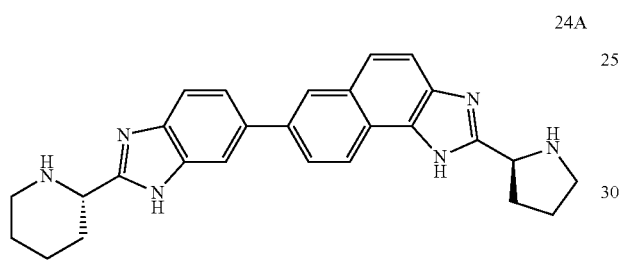

Using the method described in Example 22, Compound 8 (970 mg, 1.52 mmol) was converted to Compound 24A as a brown solid (880 mg), which was used without further purification.

Step B—Preparation of Compound 11

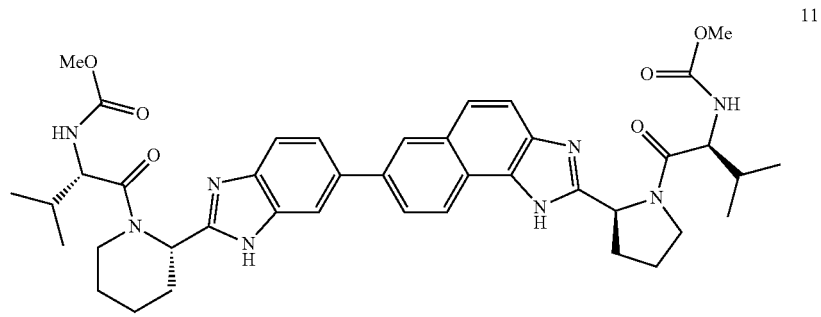 [SMILES: COC(=O)N[C@H](C(=O)N1CCCC[C@H]1c1nc2ccc(-c3ccc4c(ccc5nc([C@@H]6CCCN6C(=O)[C@@H](NC(=O)OC)C(C)C)[nH]c54)c3)cc2[nH]1)C(C)C]

A solution of Compound 4A (560 mg, 1.28 mmol), Compound Int-4 (500 mg, 2.85 mmol), diisopropylethylamine (0.9 mL, 6.75 mmol) and HATU (1.08 g, 2.48 mmol) in DMF was cooled to 0° C. The resulting solution was allowed to stir for about 15 hours, during which time, it came to room temperature on its own. The reaction mixture was then directly purified using Gilson reverse phase chromatography (0-90% acetonitrile in water with 0.1% TFA as an eluent) to provide Compound 11 as a white solid (358 mg, 37%). LCMS for: $C_{41}H_{50}N_8O_6$ (M+H)$^+$: 751.4.

Example 25

Preparation of Compound 7

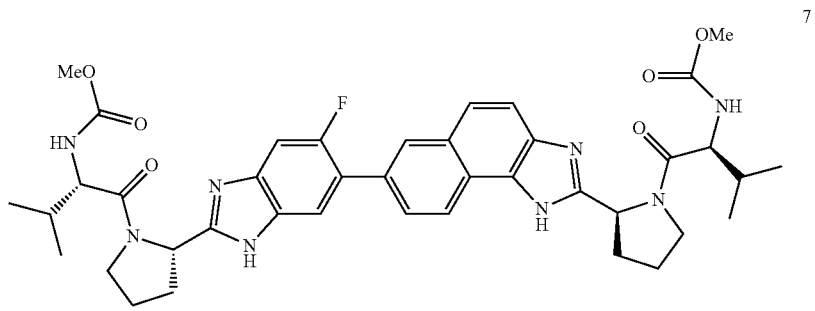 [SMILES: COC(=O)N[C@H](C(=O)N1CCC[C@H]1c1nc2cc(F)c(-c3ccc4c(ccc5nc([C@@H]6CCCN6C(=O)[C@@H](NC(=O)OC)C(C)C)[nH]c54)c3)cc2[nH]1)C(C)C]

Step A—Preparation of Compound 25B

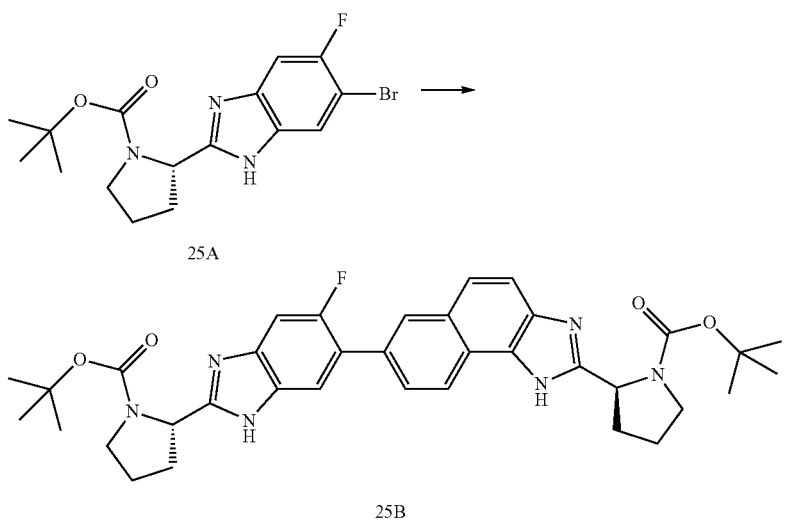

Compound 25A (400 mg, 1.4 mmol, prepared using the methods described in Example 2), Compound Int-2, bis(pinacolato)diboron (428 mg, 1.68 mmol), $Pd_2(dba)_3$—$CHCl_3$ (146 mg, 0.14 mmol), X-phos (134 mg, 0.28 mmol) and KOAc (412 mg, 4.2 mmol) were-suspended in 1,4-dioxane in a 50 mL sealed tube. The reaction mixture was degassed, then heated at 110° C. and allowed to stir at this temperature for 16 hours. The reaction mixture was cooled to room temperature, and Compound Int-6 (291 mg, 0.7 mmol), $Pd(dppf)_2Cl_2$ (115 mg, 0.14 mmol), $K_2CO_3$ (483 mg, 3.5-mmol), and $H_2O$ (1.0 mL) were added. The resulting reaction was then heated to 100° C. and allowed to stir at this temperature for 1 hour. The reaction mixture was then cooled to room temperature and diluted with $CH_2$—$Cl_2$ (100 mL) and the resulting solution was filtered through a pad of Celite. The filtrate was concentrated in vacuo and the resulting residue was purified using reverse-phase HPLC (Gilson, $CH_3CN$—$H_2O$-TFA) to provide Compound 25B (320 mg, 39.3%). LRMS: (M+H)+=583.3.

Step B—Preparation of Compound 25C

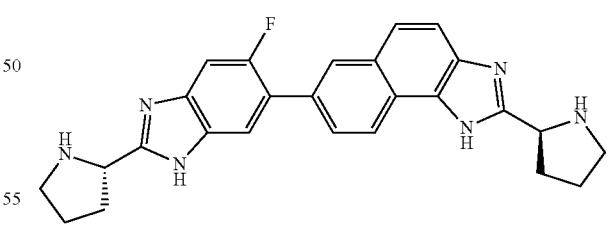

Compound 25B (310 mg, 0.53 mmol) was dissolved in a mixture of $H_2O$ (5 mL) and concentrated HCl (5 mL). The resulting reaction was heated to 90° C. and allowed to stir at this temperature for 2 hours. The reaction mixture was cooled to room temperature and concentrated in vacuo to provide Compound 25C as its HCl salt, which was used without further purification.

Step C—Preparation of Compound 7

To a solution of Compound 25C (as its —HCl salt) in DMF (10 mL) was added Compound Int-4 (223 mg, 1.27 mmol), HATU (444 mg, 1.16 mmol), and diisopropyiethylamine (0.49 mL, 2.65 mmol). The resulting reaction was allowed to stir at room temperature for 3 hours, then concentrated in vacuo. The residue obtained was purified using reverse-phase HPLC (Gilson, CH$_3$CN$^-$—H$_2$O-TFA$^-$) to provide Compound 7 (280 mg, 70.0% for 2 steps). LRMS: (M+H)$^+$=755.4.

Example 26

Preparation of Intermediate Compound Int-26f

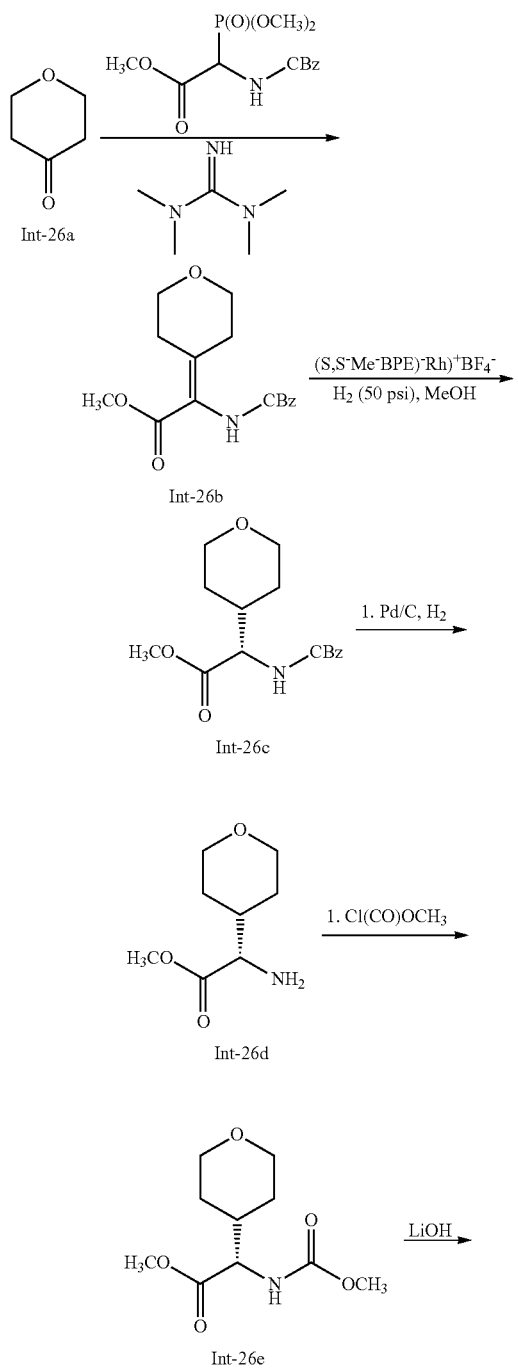

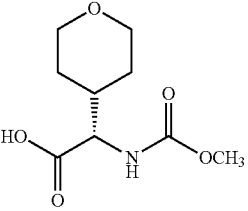

Int-26f

Step A—Preparation of Compound Int-26b

To a solution of methyl 2-(benzyloxycarbonylamino)-2-(dimethoxyphosphoryl) acetate (10.0 g, 30.2 mmol, made as decribed in Hamada et al., *Organic Letters*; English, 20:4664-4667 (2009)) in THF (100 mL) at −20° C. was added tetramethylguanidihe (4.20 mL, 33.2 mmol). The reaction mixture was allowed to stir at −20 OC for 1 hour then dihydro-2H-pyran-4(3H)-one (4a) was added (3.1 mL, 33.2 mmol) in THF (5 mL) and the reaction mixture was warmed to room temperature and allowed to stir for about 15 hours. EtOAc (200 mL) was added and the organic mixture was washed with water (3×50 mL) and brine (50 mL). The organic layers were combined and dried with Na$_2$SO$_4$, filtered and concentrated in vacuo. The residue obtained was purified using flash chromatography on an ISCO 330 g Redi-Sep column using 0-35% EtOAc/hexanes as the eluent to provide Compound Int-26b as a white solid (615 mg, 45%). 1H NMR (CDCl$_3$) δ 7.40-7.30 (m, 5H), 6.00 (br s, 1H), 5.12 (s, 2H), 3.80-3.65 (m, 7H), 2.92 (m, 2H), 2.52-2.48 (m, 2H).

Step B—Preparation of Compound Int-26c

To a solution of Int-26b (2.43 g, 7.96 mmol) in methanol (160 mL) previously purged with N$_2$ was added (−)-1,2-Bis((2S,5S)-2,5-dimethylphospholano) ethane (cyclooctadiene) rhodium(I) tetrafluoroborate (CAS#213343-65-8) (487 mg, 0.880 mmol) under N$_2$. The mixture was shaken in a Parr shaker apparatus for 18 hours at 50 psi of H$_2$. After evacuating the hydrogen, the suspension was filtered and the filtrate was concentrated in vacuo to provide Compound Int-26e as a white solid (1.30 g, 53%). $^1$H NMR (CDCl$_3$) δ 7.40-7.30 (m, 5H), 5.32 (br s, 1H), 5.12 (s, 2H), 4.40-4.30 (m, 1H), 4.00-3.95 (m, 2H), 3.75 (s, 3H), 3.40-3.25 (m, 2H), 2.10-1.95 (m, 1H), 1.50-1.45 (m, 4H).

Step C—Preparation of Compound Int-26d

To a suspension of 50% palladium on carbon (10% wet, 200 mg) in absolute ethanol (20 mL) under nitrogen was added Int-26c (1.06 g, 3.45 mmol). With stirring, the solution was placed in vacuo for 30 seconds and then was opened to a hydrogen gas balloon for 2 hours. After evacuating the hydrogen, the suspension was filtered through a Celite pad and the pad was washed with ethanol (2×20 mL). The filtrate was concentrated in vacuo to provide Compound Int-26d as a colorless oil (585 mg, 98%). $^1$H NMR (CDCl$_3$) δ 4.06-3.96 (m, 2H), 3.73 (s, 3H), 3.48-3.28 (m, 3H), 1.92-1.78 (m, 1H), 1.61-1.47 (m, 6H).

Step D—Preparation of Compound Int-26e

To a solution of Compound Int-26d (585 mg, 3.37 mmol) and triethylamine (0.710 mL, 5.09-mmol) in CH$_2$Cl$_2$ (6 mL) was added methyl chloroformate (0.290 mL, 3.76 mmol). The reaction was allowed to stir at room temperature for about 15 hours, then water (15 mL) was added and the aqueous mixture was extracted with CH$_2$C$_2$(3×20 mL). The combined organic extracts were dried over Na$_2$SO$_4$, filtered and concentrated in vacuo. The residue obtained was purified using flash chromatography on an ISCO 24 g Redi-Sep column using 0-3% MeOH/CH$_2$Cl$_2$ as the eluent to provide Compound Int-26e as a colorless oil (600 mg, 77%). $^1$H NMR (CDCl$_3$) δ 5.27-5.18 (m, 1H), 4.38-4.28 (m, 1H), 4.06-3.96 (m, 2H), 3.75 (s, 3H), 3.69 (s, 3H), 3.39-3.30 (m, 2H), 2.09-1.94 (m, 1H), 1.59-1.48 (m, 4H).

Step E—Preparation of Compound Int-26f

To a solution of Compound Int-26e (600 mg, 2.59 mmol) in THF (5 mL) was added lithium-hydroxide monohydrate (218 mg, 5.19 mmol) in water (5 mL). The reaction was allowed to stir at room temperature for 2 hours then was concentrated in vacuo to half of its original volume. The concentrated mixture was then acidified with 6N HCl and extracted with EtOAc (7×50 mL). The combined organic extracts were dried over Na$_2$SO$_4$, filtered and concentrated in vacuo to provide Compound Int-26f as an off-white solid (485 mg, 86%). $^1$H NMR (CD$_3$OD) δ 4.09-4.07 (m, 1H), 3.96-3.92 (m, 2H), 3.65 (s, 3H), 3.40-3.34 (nm, 2H), 2.10-1.99 (m, 1H), 1.56-1.47 (m, 4H).

Example 27

Preparation of Intermediate Compound Int-27f

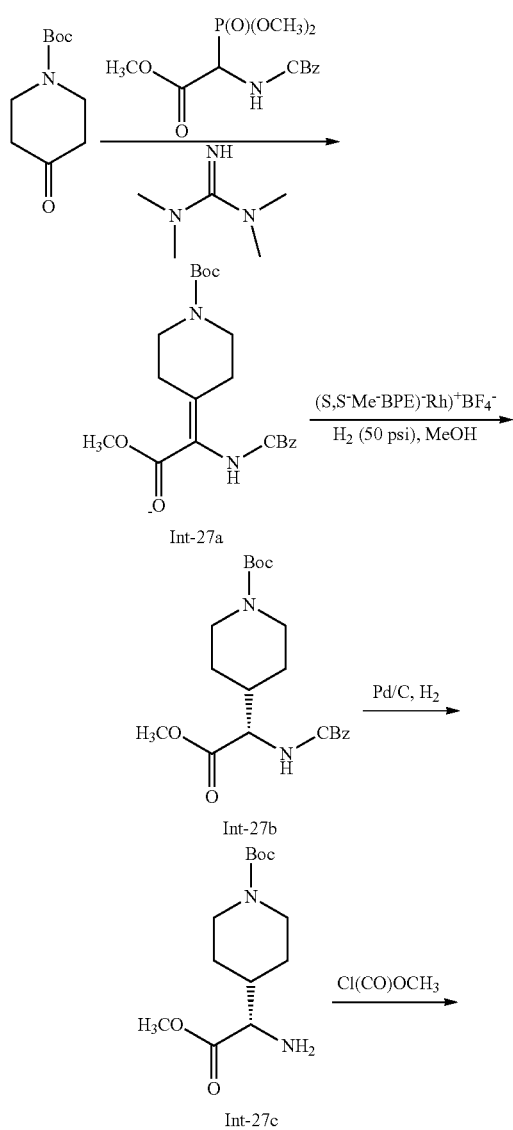

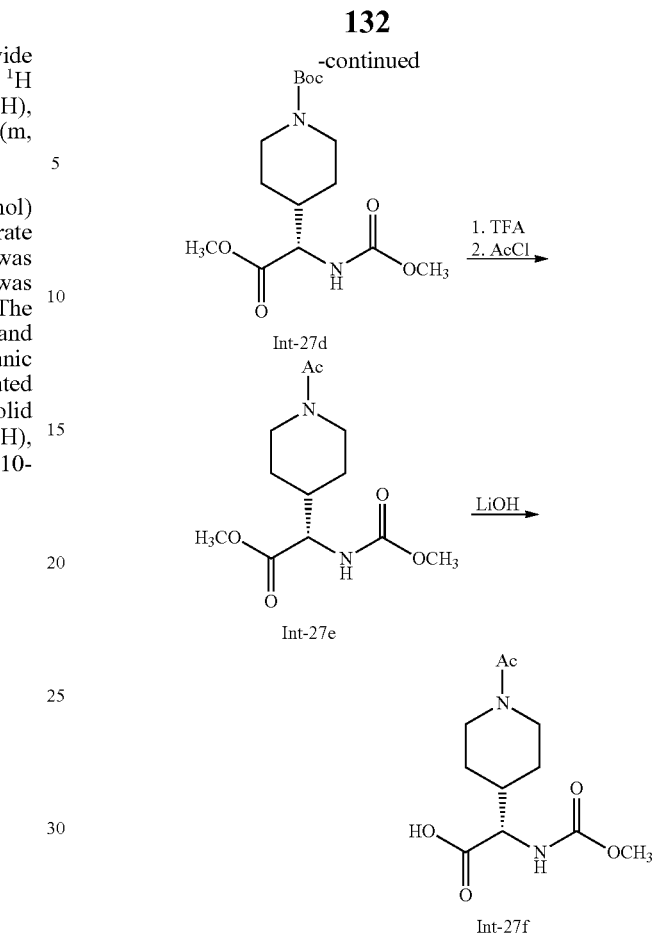

Step A—Preparation of Compound Int-27a

To a solution of methyl 2-(benzyloxycarbonylamino)-2-(dimethoxyphosphoryl) acetate (1.50 g, 4.52 mmol) in THF (5 mL) at −20° C. was added tetramethylguanidine (625 µL, 4.98 mmol). The reaction mixture was allowed to stir at −20 OC for 1 hour then tert-butyl 4-oxopiperidine-1-carboxylate was added (992 mg, 4.97 mmol) in THF (2 mL) and the reaction mixture was warmed to room temperature and allowed to stir for about 15 hours. EtOAc (90 mL) was added and the organic mixture was washed with water (3×20 mL) and brine (25 mL). The combined organic extracts were dried over Na$_2$SO$_4$, filtered and concentrated in vacuo. The residue obtained was purified using flash chromatography on an ISCO 40 g Redi-Sep column using 0-35% EtOAc/hexanes as the eluent to provide Compound Int-27a as a white semi-solid (1.1 g, 61%). $^1$H NMR (CDCl$_3$) δ 7.40-7.30 (m, 5H), 6.02 (br s, 1H), 5.12 (s, 2H); 3.80-3.40 (m, 7H); 2.90-2.80 (m, 2H), 2.45-2.35 (m, 2H), 1.45 (s, 9H).

Step B—Preparation of Compound Int-27b

To a solution of Int-27a (1.30 g, 3.21 mmol) in methanol (90 mL) previously purged with N$_2$ was added (−)-1,2-Bis ((2S,5S)-2,5-dimethylphospholano) ethane(cyclooctadiene) rhodium(I) tetrafluoroborate (197 mg, 0.354 mmol) under N$_2$. The mixture was then shaken in a Parr shaker apparatus for 18 hours at 50 psi of H$_2$. After evacuating the hydrogen, the suspension was filtered and the filtrate was concentrated in vacuo to provide Compound Int-27b as colorless oil (1.00-g, 77%). $^1$H NMR (CDCl$_3$) δ 7.40-7.30 (m, 5H), 5.35-5.25 (m, 1H), 5.10 (s, 2H), 4.40-4.35 (m, 1H), 4.20-4.10 (m, 2H), 3.70 (s, 3H), 2.70-2.55 (m, 2H), 2.00-1.90 (m, 1H), 1.65-1.40 (m, 11H), 1.30-1.20 (m, 2H).

Step C—Preparation of Compound Int-27c

To a solution of 50% palladium on carbon (10% wet, 250 mg) in absolute ethanol (20 mL) under nitrogen was added Int-27b (1.00 g, 2.46 mmol). The reaction was evacuated, then put under an H₂ atmosphere using a hydrogen-filled balloon and allowed to stir for 2 hours. The hydrogen was evacuated and the resulting suspension was filtered through a Celite pad and the pad washed with ethanol (2×20 mL). The filtrate and ethanol washings were combined and concentrated in vacuo- to provide Compound Int-27c as a colorless oil (670 mg, quant.). ¹H NMR (CDCl₃) δ 4.21-4.08 (m, 2H), 3.73 (s, 3H), 3.31 (d, J=6.0 Hz, 1H), 2.75-2.57 (m, 2H), 1.84-1.70 (m, 1H), 1.68-1.56 (m, 1H), 1.45 (s, 9H), 1.45-1.20 (m, 5H).

Step D—Preparation of Compound Int-27d

To a solution of Compound Int-27c (670 mg, 2.46 mmol) and triethylamine (0.520 mL, 3.73 mmol) in CH₂Cl₂ (10 mL) was added methyl chloroformate (0.210 mL, 2.72 mmol). The reaction mixture was allowed to stir at room temperature for about 15 hours. Water (20 mL) was added and the aqueous mixture was extracted with CH₂Cl₂ (2×15 mL). The combined organic extracts were dried over Na₂SO₄, filtered and concentrated in vacuo. The residue obtained was purified using flash chromatography on an ISCO 24 g Redi-Sep column using 0-3% MeOH/CH₂Cl₂ as the eluent to provide Compound Int-27d as an off-white solid (515-mg, 63%). ¹H NMR (CDCl₃) δ 5.26-5.17 (m, 1H), 4.38-4.30 (m, 1H), 4.20-4.07 (m, 2H), 3.75 (s, 3H), 3.68 (s, 3H), 2.71-2.57(m, 2H), 2.00-1.85 (m, 1H), 1.87-1.48 (m, 2H), 1.44 (s, 9H), 1.35-1.18 (m, 2H).

Step E—Preparation of Compound Int-27e

Compound Int-27d (300 mg, 0.908 mmol) was dissolved in a mixture of TFA (2 mL) and CH₂Cl₂ (10 mL) and the sol-at-ion was allowed to stir at room temperature for 1 hour, then was concentrated in vacuo. To the resulting residue was added triethylamine (0.760 mL, 5.45 mmol) in CH₂Cl₂ (10 mL), then acetic anhydride (0.086 mL, 0.915 mmol). The reaction was allowed to stir at room temperature for about 15 hours then concentrated in vacuo. The residue obtained was purified using flash chromatography on an ISCO 12 g Redi-Sep column using 0-4% MeOH/CH₂Cl₂ as the eluent to provide Compound Int-27e as colorless oil (247 mg, 99%). ¹H NMR (CDCl₃) δ 5.27-5.21 (m, 1H), 4.73-4.62 (m, 1H), 4.42-4.32 (m, 1H), 3.69 (s, 3H), 3.18 (s, 3H), 3.18-3.09 (m, 1H), 3.07-2.95 (m, 1H), 2.55-2.41 (m, 1H), 2.07 (s, 3H), 1.78-1.49 (m, 3H), 1.38-1.21 (m, 2H).

Step F—Preparation of Compound Int-27f

To a solution of Compound Int-27e (247 mg, 2.59 mmol) in THF (3 mL) was added lithium hydroxide monohydrate (77 mg, 1.83 mmol) in water (3 mL). The reaction mixture was allowed to stir at room temperature for about 15 hours then concentrated in vacuo to 50% of its original volume. The concentrated solution was then acidified with 1N HCl to pH 4 and extracted with EtOAc (7×15 mL). The combined organic extracts were dried over Na₂SO₄, filtered and concentrated in vacuo to provide Compound Int-27f as an off-white solid (106 mg, 45%). ¹H NMR (CD₃OD) δ 5.52-5.43 (m, 1H), 4.71-4.62 (m, 1H), 4.44-4.31 (m, 1H), 3.91-3.81 (M, 1H), 3.70 (s, 3H), 3.12-2.99 (m, 1H), 2.58-2.46 (m, 1H), 2.10 (m, 4H), 1.86-1.54 (m, 2H), 1.50-1.21 (m, 3H).

Example 28

Preparation of Intermediate Compound Int-28f

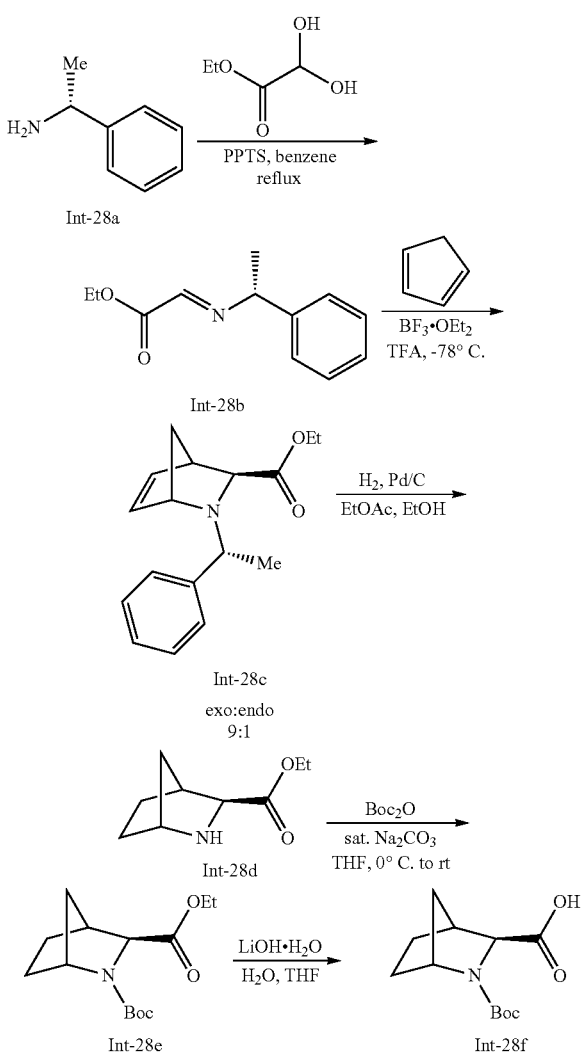

Step A—Preparation of Compound Int-28c

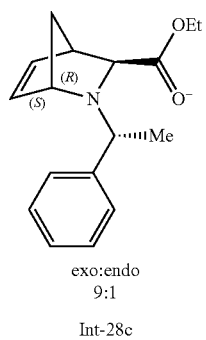

A stirred mixture of D-(+)-α-methylbenzyl amine Int-28a (50.0 g, 0.412 mol), ethyl glyoxylate (81.5 mL, 50% in toluene, 0.412 mol) and PPTS (0.50 g, 2.00 mmol) in benzene (600 mL) was heated to reflux in a Dean-Stark apparatus and allowed to remain at reflux until no further water (~8 mL) azeotroped from the reaction (~4 hours). The resulting mixture was concentrated in vacuo to provide Compound Int-28b, which was used without further purification: $^1$H NMR (300 MHz, CDCl$_3$) δ 7.72 (s, 1H); 7.36-7.24 (m, 5H), 4.61 (q, J=6.9 Hz, 1H), 4.35 (q, J=7.2 Hz, 2H), 1.62 (d, J=6.6 Hz, 3H), 1.34 (t, J=7.2 Hz, 3H).

To a stirred solution of crude Int-28b in methylene chloride (600 mL) at –78° C. were added the following in 10 minute intervals: TFA (31.0 mL, 0.416 mol), boron trifluoride etherate (51.3 mL, 0.416 mol) and freshly distilled cyclopentadiene (32.7 g, 0.494 mol). After less than 2 minutes following the addition of cyclopentadiene, the reaction mixture formed a thick brown mass, which was allowed to stir for 6 hours at –7820 C. The reaction mixture was then-allowed to warm to room temperature on-its own and stir for an additional 15 hours. The resulting dark-brown reaction mixture was quenched with sat. aq. Na$_2$CO$_3$ (~900 mL) and allowed to stir for 30 minutes. The resultant suspension was filtered through a pad of Celite® and the filtrate was extracted with methylene chloride (3×100 mL). The combined organic extracts were washed with sat. aq. NaCl (2×75 mL), dried over Na$_2$SO$_4$, filtered and concentrated in vacuo. The residue obtained was purified using flash column chromatography (silica; 8×18 cm, 10% to 25% ethyl acetate/hexanes as the eluent) to provide endo Int-28c (10.9 g, 9%) as a brown oil: $^1$H NMR (300 MHz, CDCl$_3$) δ 7.34-7.19 (m, 5H), 6.00-5.95 (m, 1H), 4.18 (q, J=7.1 Hz, 3H), 3.47 (s, 1H), 3.03 (s, 1H), 2.97 (q, J=6.5 Hz, 1H), 2.41 (s, 1H), 1.86 (d, J=8.2 Hz, 1H), 1.26 (t, J=6.6 Hz, 3H), 1.17 (t, J=6.6 Hz, 3H). Exo Int-28c (84.3 g, 74%) was also collected as a brown oil: $^1$H NMR (300 MHz, CDCl$_3$) δ 7.34-7.1.9 (m, 5H), 6.36-6.33 (m, 1H), 6.22-6.18 (m, 1H), 4.37 (s, 1H), 3.87 (q, J=6.8 Hz, 2H), 3.10 (q, J=6.5 Hz, 1H), 2.96 (s, 1H), 2.27 (s, 1H), 2.20 (d, J=8.4 Hz, 1H), 1.48 (d, J=6.5 Hz, 3H), 1.01 (d, J=7.0 Hz, 3H), 1.00 (m, 1H).

Step B—Representative Example for the Preparation of Compound Int-28d

A mixture of exo-Int-28c (15.8 g, 0.582 mol) and 10% Pd/C (4.07 g, 50% wet) in a 1:2 mixture of EtOH/EtOAc (150 mL) was shaken for 23 hours in a Parr hydrogenation apparatus under an atmosphere of H$_2$ (50 psi). The reaction mixture was then filtered through Celite® and the filtrate was concentrated in vacuo: $^1$H NMR analysis of the residue (10.8 g) showed some aromatic resonances present. Repetition of the hydrogenation procedure using 10% Pd/C (2.0 g) afforded Int-28d (10.0 g, quant.) as a brown oil, which was used without further purification. $^1$H NMR (300 MHz, CDCl$_3$) δ 4.18 (q, J=7.2 Hz, 3H), 3.54 (s, 1H), 3.32 (s, 1H), 2.62 (s, 1H), 2.23 (s, 1H), 1.64-1.39 (m, 5H), 1.31-1.20 (m, 4H).

Step C—Preparation of Compound Int-28e

To a solution of Int-28d (36.6 g, 0.236 mol) and sat. aq. Na$_2$CO$_3$ (300 mL) in THF (600 mL) at 0° C. was added di-tert-butyl dicarbonate (59.0 g, 0.270 mol). The resulting reaction was allowed to slowly warm to room temperature with stirring over 6 hours, then was allowed to stir at room temperature for an additional 68 hours. The reaction mixture was diluted with EtOAc (250 mL) and water (250 mL) and the aqueous layer was extracted with EtOAc (2×200 mL). The combined organic extracts were washed with sat. aq. NaCl (2×75 mL), dried over Na$_2$SO$_4$, filtered and concentrated in vacuo. The residue obtained was purified using flash column chromatography (silica; 16×10 cm) using 10-20% ethyl acetate/hexanes as the eluent to provide Compound Int-28e (49.0 g, 84%) as a pale yellow oil: $^1$H NMR (300 MHz, CDCl$_3$) δ 4.35 (s, 0.6H), 4.22-4.10 (m, 2.4H), 3.81 (s, 0.45H), 3.71 (s, 0.55H), 2.66 (s, 1H), 1.96-1.90 (m, 1H), 1.76-1.50 (m, 3H), 1.55-1.45 (m, 5H), 1.39 (s, 5H), 1.30-1.23 (m, 4H).

Step D—Preparation of Compound 2.2.1 Bicyclic Acid Intermediate Int-28f

To a stirred mixture of Int-28e (49.0 g, 0.182 mmol) in 1:1 THF/water (600 mL) was added LiOH.H$_2$O (15.3 g, 0.364 mol). The reaction mixture was heated to 60° C. and allowed to stir at this temperature for 47 hours. The reaction mixture was then cooled to room temperature, concentrated in vacuo, and the residue obtained was diluted with CH$_2$Cl$_2$ (200 mL) then acidified with 2N HCl to pH ~4. The acidic solution was extracted with CH$_2$Cl$_2$ (4×100 mL) and the combined organic extracts were washed with sat. aq. NaCl (25 mL), dried over Na$_2$SO$_4$, filtered and concentrated in vacuo to provide Compound Int-28f, (1R,3S,4S)—N-Boc-2-azabicyclo[2.2.1]heptane-3-carboxylic acid (41.2 g, 93%) as art off white solid, which was used without further purification: $^1$H NMR (400 MHz, DMSO-d$_6$) δ 12.44 (s, 1H), 4.13 (s, 0.56H), 4.06 (s, 0.47H), 3.61 (d, J=4.0 Hz, 1H), 2.59 (s, 1H), 1.75-1.45 (m, 5H), 1.39 (s, 4H), 1.32 (s, 5H), 1.23 (t, J=8.4 Hz, 1H); Optical Rotation: $[\alpha]^D 25$ –169.0° (c=1.1, CHCl$_3$).

Example 29

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 M to 1 µM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCT-GCGG (SEQ. ID NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ΔCT values (CT-CT$_{5B}$CT$_{GAPDH}$) were plotted against the concentration of test compound and fitted to the sigmoid dose-response model using XLfit4 (MDL). EC$_{50}$ was defined as the concentration of inhibitor necessary to achieve ΔCT=1 over the projected baseline; EC$_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et at, *Antimicrobial Agents and Chemotherapy* 50: 1013-1020 (2006).

HCV replicon assay data was calculated for selected compounds of the present invention using this method and is provided in the table below. EC$_{90}$ data for selected compounds of the present invention is provided in the table below wherein A is <1 nM, B is 1-999 nM, and C is ≥1000 nM.

| Compound number | Structure | LRMS | Biological activity |
|---|---|---|---|
| 1 | 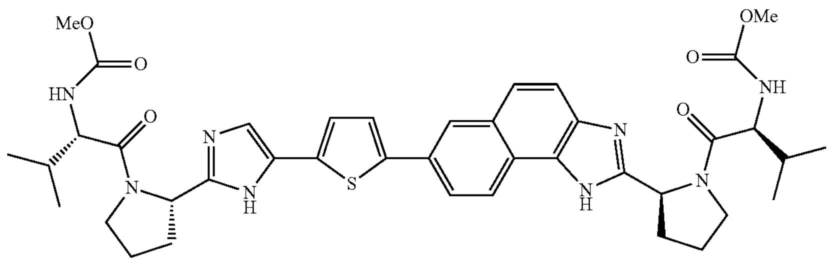 [SMILES: COC(=O)N[C@H](C(=O)N1CCC[C@H]1c1ncc(-c2ccc(-c3ccc4c(ccc5nc([C@@H]6CCCN6C(=O)[C@@H](NC(=O)OC)C(C)C)[nH]c54)c3)s2)[nH]1)C(C)C] | (M + H)+: 769.5 | A |
| 2 | 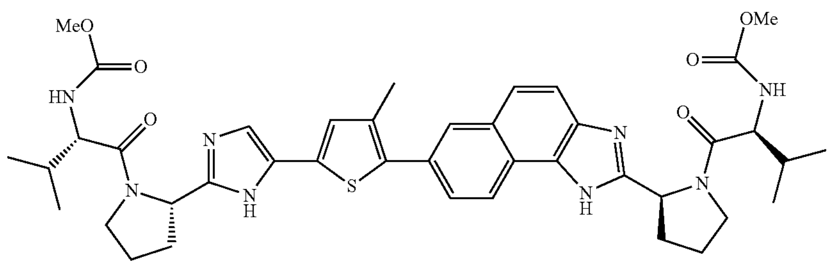 [SMILES: COC(=O)N[C@H](C(=O)N1CCC[C@H]1c1ncc(-c2cc(C)c(-c3ccc4c(ccc5nc([C@@H]6CCCN6C(=O)[C@@H](NC(=O)OC)C(C)C)[nH]c54)c3)s2)[nH]1)C(C)C] | (M + H)+: 783.5 | A |
| 3 | 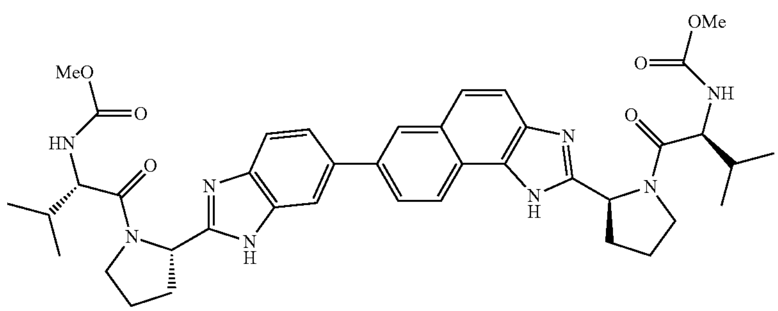 [SMILES: COC(=O)N[C@H](C(=O)N1CCC[C@H]1c1nc2ccc(-c3ccc4c(ccc5nc([C@@H]6CCCN6C(=O)[C@@H](NC(=O)OC)C(C)C)[nH]c54)c3)cc2[nH]1)C(C)C] | (M + H)+: 737 | A |
| 4 | 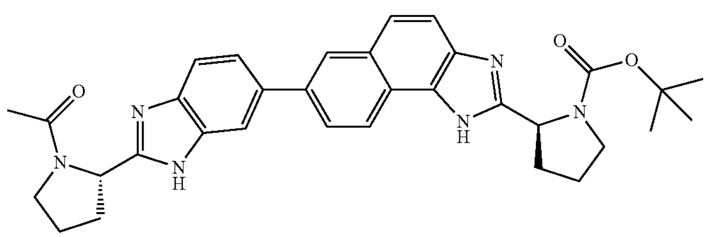 [SMILES: CC(=O)N1CCC[C@H]1c1nc2ccc(-c3ccc4c(ccc5nc([C@@H]6CCCN6C(=O)OC(C)(C)C)[nH]c54)c3)cc2[nH]1] | (M + H)+: 565 | C |
| 5 | 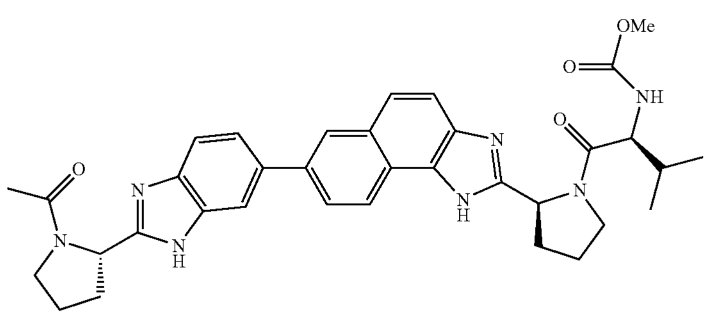 [SMILES: COC(=O)N[C@H](C(=O)N1CCC[C@H]1c1nc2ccc3cc(-c4ccc5nc([C@@H]6CCCN6C(C)=O)[nH]c5c4)ccc3c2[nH]1)C(C)C] | (M + H)+: 622 | A |

-continued
| Compound number | Structure | LRMS | Biological activity |
|---|---|---|---|
| 6 | 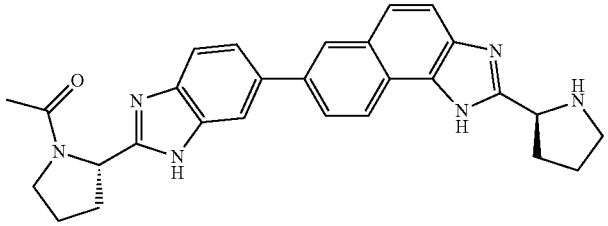 [SMILES: CC(=O)N1CCC[C@H]1c1nc2ccc(-c3ccc4c(ccc5nc([C@@H]6CCCN6)[nH]c54)c3)cc2[nH]1] | (M + H)+: NA | B |
| 7 | 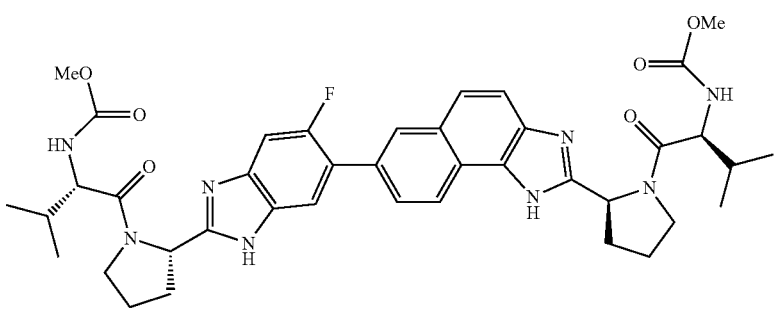 [SMILES: COC(=O)N[C@H](C(=O)N1CCC[C@H]1c1nc2cc(F)c(-c3ccc4c(ccc5nc([C@@H]6CCCN6C(=O)[C@@H](NC(=O)OC)C(C)C)[nH]c54)c3)cc2[nH]1)C(C)C] | (M + H)+: 755.4 | A |
| 8 | 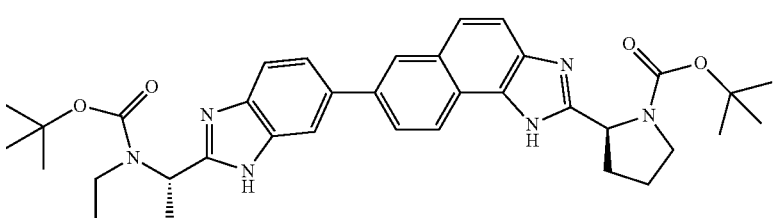 | (M + H)+: 637.4 | B |
| 9 | 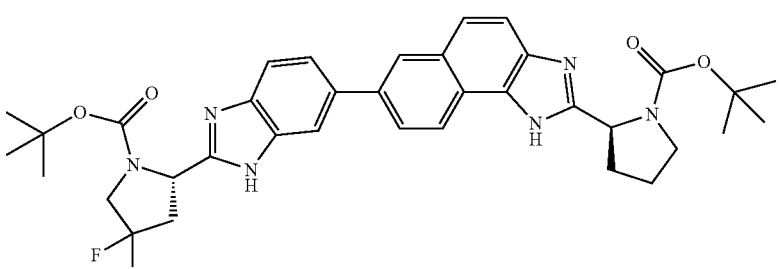 | (M + H)+: 659.4 | B |
| 10 | 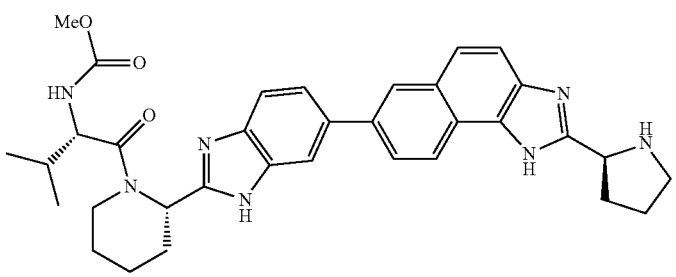 [SMILES: COC(=O)N[C@H](C(=O)N1CCCC[C@H]1c1nc2ccc(-c3ccc4c(ccc5nc([C@@H]6CCCN6)[nH]c54)c3)cc2[nH]1)C(C)C] | (M + H)+: NA | B |

-continued

| Compound number | Structure | LRMS | Biological activity |
|---|---|---|---|
| 11 | 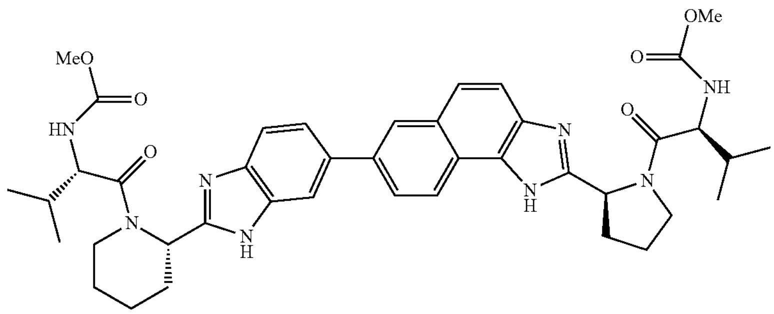 [SMILES: COC(=O)N[C@H](C(=O)N1CCCC[C@H]1c1nc2ccc(-c3ccc4c(ccc5nc([C@@H]6CCCN6C(=O)[C@@H](NC(=O)OC)C(C)C)[nH]c54)c3)cc2[nH]1)C(C)C] | (M + H)+: 751.4 | A |
| 12 | 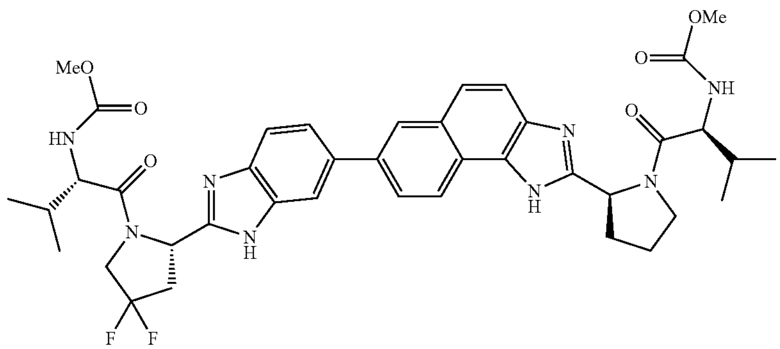 [SMILES: COC(=O)N[C@H](C(=O)N1CC(F)(F)C[C@H]1c1nc2ccc(-c3ccc4c(ccc5nc([C@@H]6CCCN6C(=O)[C@@H](NC(=O)OC)C(C)C)[nH]c54)c3)cc2[nH]1)C(C)C] | (M + H)+: 772.4 | A |
| 13 | 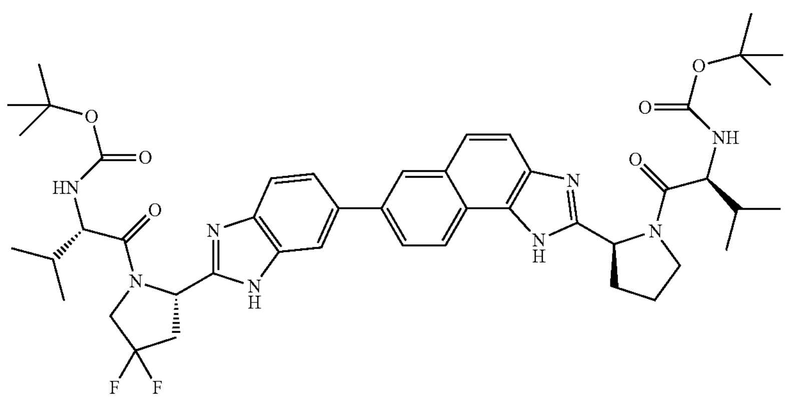 [SMILES: CC(C)[C@H](NC(=O)OC(C)(C)C)C(=O)N1CC(F)(F)C[C@H]1c1nc2ccc(-c3ccc4c(ccc5nc([C@@H]6CCCN6C(=O)[C@@H](NC(=O)OC(C)(C)C)C(C)C)[nH]c54)c3)cc2[nH]1] | (M + H)+: 857.5 | A |
| 14 | 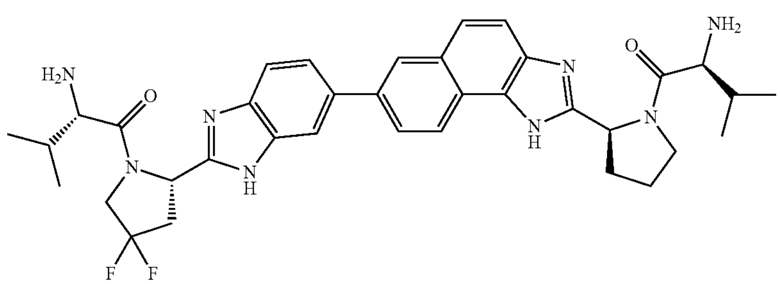 [SMILES: CC(C)[C@H](N)C(=O)N1CC(F)(F)C[C@H]1c1nc2ccc(-c3ccc4c(ccc5nc([C@@H]6CCCN6C(=O)[C@@H](N)C(C)C)[nH]c54)c3)cc2[nH]1] | (M + H)+: 657.4 | B |
| 15 | 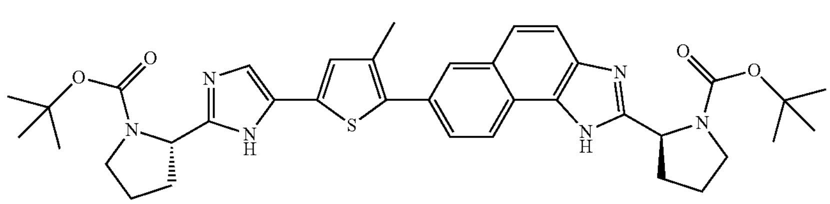 | (M + H)+: 645.5 | B |

| Compound number | Structure | LRMS | Biological activity |
|---|---|---|---|
| 16 | 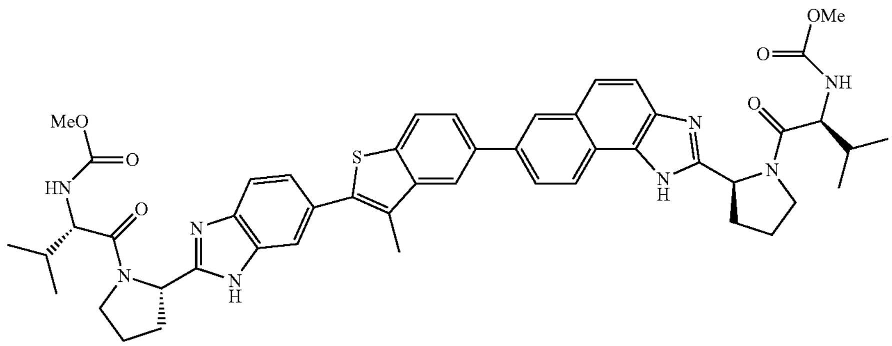 [SMILES: COC(=O)N[C@H](C(=O)N1CCC[C@H]1c1nc2ccc(-c3sc4ccc(-c5ccc6c(ccc7nc([C@@H]8CCCN8C(=O)[C@@H](NC(=O)OC)C(C)C)[nH]c76)c5)cc4c3C)cc2[nH]1)C(C)C] | (M + H)+: NA | A |
| 17 | 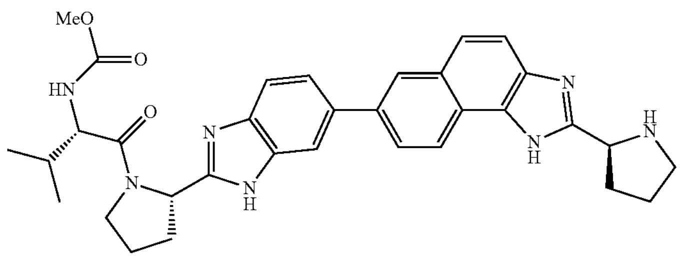 [SMILES: COC(=O)N[C@H](C(=O)N1CCC[C@H]1c1nc2ccc(-c3ccc4c(ccc5nc([C@@H]6CCCN6)[nH]c54)c3)cc2[nH]1)C(C)C] | (M + H)+: NA | B |

The study of the HCV life cycle has been difficult due to the lack of a cell-culture system to support the HCV virus. To date, compounds in different structural classes acting on different sites within the HCV polyprotein have demonstrated efficacy in various species, including humans, in reducing HCV viral titers. Furthermore, the subgenomic replicon assay is highly correlated with efficacy in non-humans and humans infected with HCV. See K. del Carmen et al., *Annals of Hepatology*, 2004, 3:54.

It is accepted that the HCV replicon system described above is useful for the development and the evaluation of antiviral drugs. See Pietschmann, T. & Bartenschlager, R., *Current Opinion in Drug Discovery Research* 2001, 4:657-664).

Uses of the Fused Tricyclic Compounds

The Fused Tricyclic Compounds are useful in human and veterinary medicine for treating or preventing a viral infection or a virus-related disorder in a patient. In accordance with the invention, the Fused Tricyclic Compounds can be administered to a patient in need of treatment or prevention of a viral infection or a virus-related disorder.

Accordingly, in one embodiment, the invention provides methods for treating a viral infection in a patient comprising administering to the patient an effective amount of at least one Fused Tricyclic Compound or a pharmaceutically acceptable salt thereof. In another embodiment, the invention provides methods for treating a virus-related disorder in a patient comprising administering to the patient an effective amount of at least one Fused Tricyclic Compound or a pharmaceutically acceptable salt thereof.

Treatment or Prevention of a Viral Infection

The Fused Tricyclic Compounds can be useful for treating or preventing a viral infection. In one embodiment, the Fused Tricyclic Compounds can be inhibitors of viral replication. In a specific embodiment, the Fused Tricyclic Compounds can be inhibitors of HCV replication. Accordingly, the Fused Tricyclic Compounds are useful for treating viral infections, such as HCV.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et a., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et at, *J Gen Virol*, 75(Pt 5):1053-106-1 (1994)).

Treatment or Prevention of a Virus-Related Disorder

The Fused Tricyclic Compounds can be useful for treating or preventing a virus-related disorder. Accordingly, the Fused Tricyclic Compounds are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The Fused Tricyclic Compounds can be useful for treating or preventing a RNA dependent polymerase (RdRp) related disorder in a patient. Such disorders include viral infections wherein the infective virus contains a RdRp enzyme.

Accordingly, in one embodiment, the present invention provides a method for treating a RNA dependent polymerase-related disorder in a patient, comprising administering to the patient an effective amount of at least one Fused Tricyclic Compound or a pharmaceutically acceptable salt thereof.

Treatment or Prevention of a Disorder Related to HCV Infection

The Fused Tricyclic Compounds can be useful for treating or preventing a disorder related to a HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating a HCV-related disorder in a patient, wherein the method comprises administering to the patient a therapeutically effective amount of at least one Fused Tricyclic Compound, or a pharmaceutically acceptable salt thereof.

Combination Therapy

In another-embodiment, the present methods for treating or preventing a viral infection or a virus-related disorder can further comprise the administration of one or more additional therapeutic agents which are not Substituted Fused Tricyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Substituted Fused Tricyclic Compound, or a pharmaceutically acceptable salt thereof, and (ii) at least one additional therapeutic agent that is other than a Substituted Fused Tricyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Substituted Fused Tricyclic Compound and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one Substituted Fused Tricyclic Compound is administered during a time when the additional therapeutic agent(s) exert their prophylactic or therapeutic effect, or vice versa.

In another embodiment, the at least one Substituted Fused Tricyclic Compound and the additional therapeutic agent(s) are administered in doses commonly employed when such agents are used as monotherapy for treating a viral infection.

In another embodiment, the at least one Substituted Fused Tricyclic Compound and the additional therapeutic agent(s) are administered in doses lower than the doses commonly employed when such agents are used as monotherapy for treating a viral infection.

In still another embodiment, the at least one Substituted Fused Tricyclic Compound and the additional therapeutic agent(s) act synergistically and are administered in doses lower than the doses commonly employed when such agents are used as monotherapy for treating a viral infection.

In one embodiment, the at least one Substituted Fused Tricyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Substituted Fused Tricyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration, of at least one Substituted Fused Tricyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder. In one embodiment, additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, and an antibody therapy (monoclonal or polyclonal).

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In one embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In another embodiment, the additional therapeutic agent is an HCV entry inhibitor.

In another embodiment, the additional therapeutic agent is an HCV assembly inhibitor.

In one embodiment, the additional therapeutic agents comprise a protease inhibitor and a polymerase inhibitor.

In still another embodiment, the additional therapeutic agents comprise a protease inhibitor and an immunomodulatory agent:

In yet-another embodiment, the additional therapeutic agents comprise a polymerase inhibitor and an immunomodulatory agent.

In another embodiment, the additional therapeutic agents comprise a protease inhibitor and ca nucleoside.

In another embodiment, the additional therapeutic agents comprise an immunomodulatory agent and a nucleoside.

In one embodiment, the additional therapeutic agents comprise a protease inhibitor and a NS5A inhibitor.

In another embodiment, the additional therapeutic agents comprise a nucleoside and a NS5A inhibitor.

In another embodiment, the additional therapeutic agents comprise a protease inhibitor, an immunomodulatory agent and a nucleoside.

In still another embodiment, the additional therapeutic agents comprise a protease inhibitor, a nucleoside and a NS5A inhibitor.

In a further embodiment, the additional therapeutic agents comprise a protease inhibitor, a polymerase inhibitor and an immunomedulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281. (Merck), VCH222 (ViroChem), VCH916 (ViroChem), VCH716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125;

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron-CR(Octoplus), IFN-α-2b-XL (Flame: Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 1208, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhbitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex); VX-813 (Vertex), VBY-376 (Virobay), BI-201335 (Boehringer Ingelheim), TMC-435 (Medivir/Tibotec), ABT-450 (Abbott), MK-7009 (Merck), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (idenix), ITMN-8356 (InterMune), ITMN-8347 (InterMune), ITMN-8096 (InterMune), ITMN-7587 (InterMune), PHX1766 (Phenomix), amprenavir, atazanavir, fosemprenavir, indinavir, lopinavir, ritonavir, nelfinavir, saquinavir, tipranavir, Kaletra (a combination of ritonavir and lopinavir) and TMC 114.

Additional examples of HCV protease inhbitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinás-Brunet et al., *Bioorg Med Chem Lett*, 8(13):1713-1718 (1998); Martin et al., *Biochemistry*, 37(33): 11459-11468 (1998); Dimasi et al., *J Virol*, 71(10):7461-7469 (1997); Martin et al., *Protein Eng*, 10(5) .607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

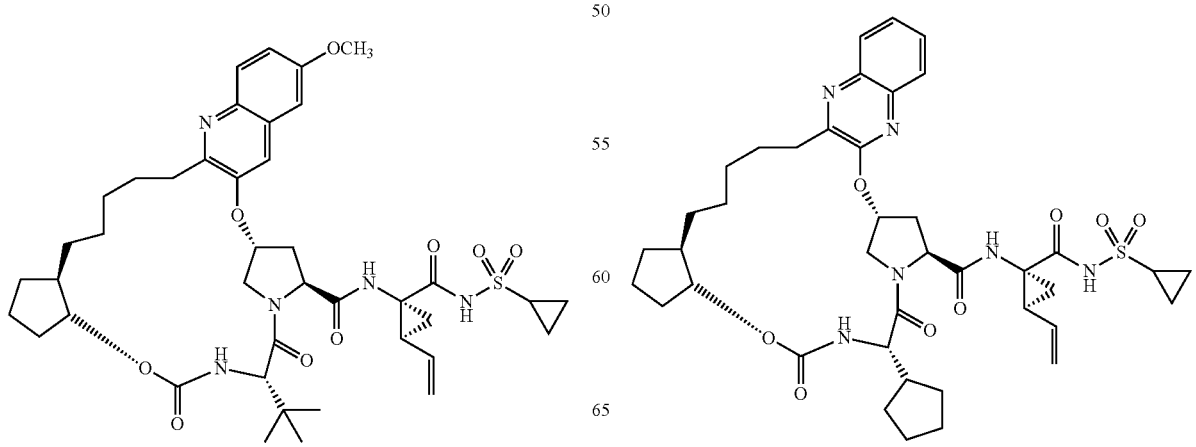

-continued

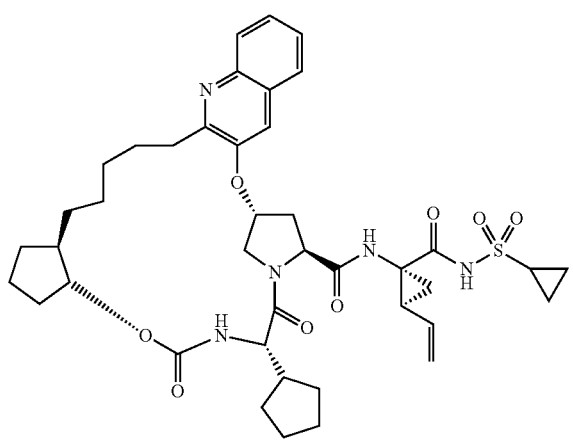

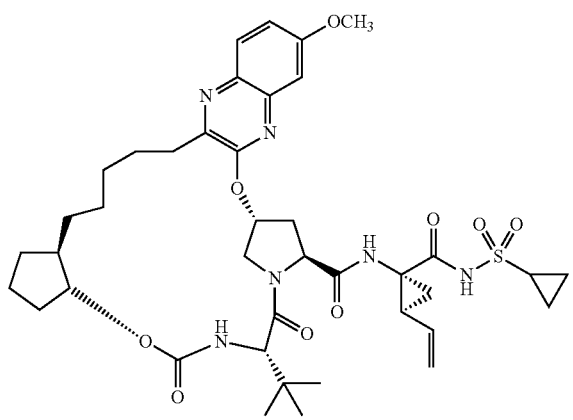

151
-continued
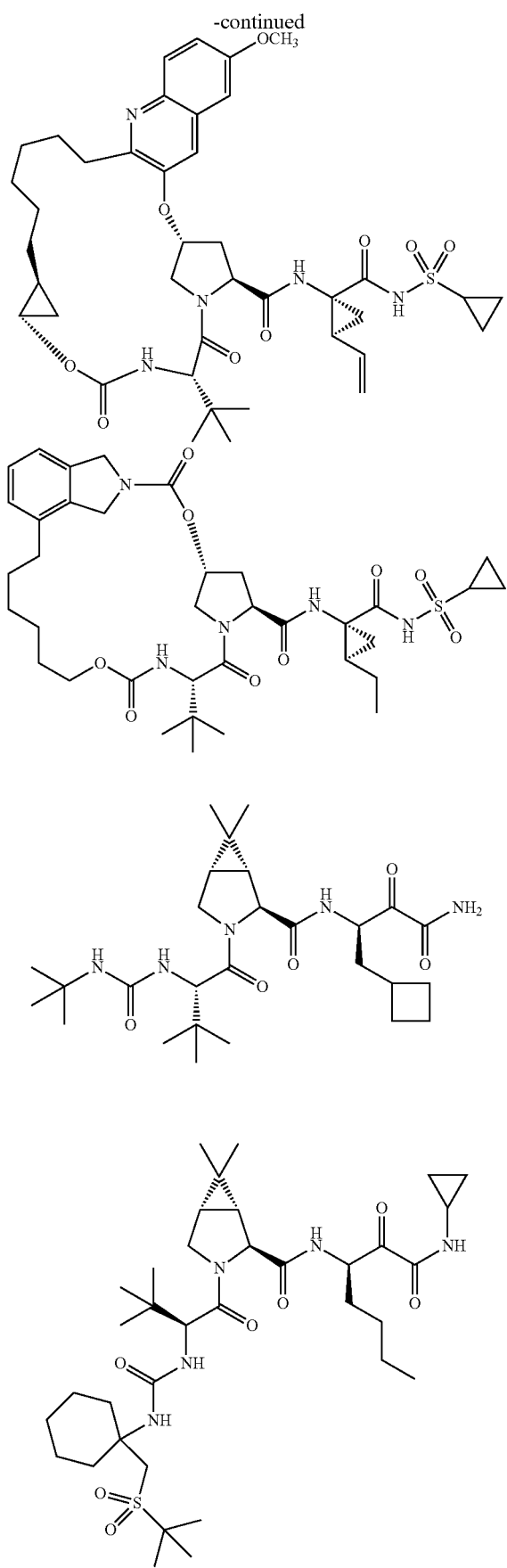
152
-continued
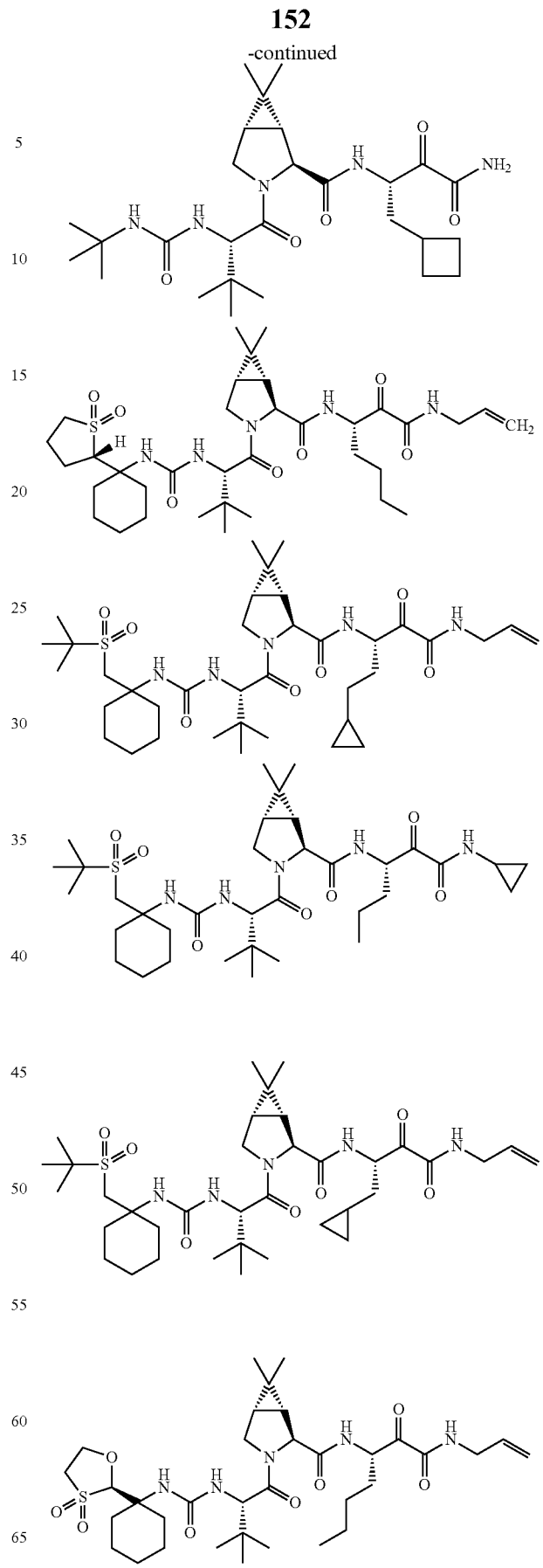

153
-continued
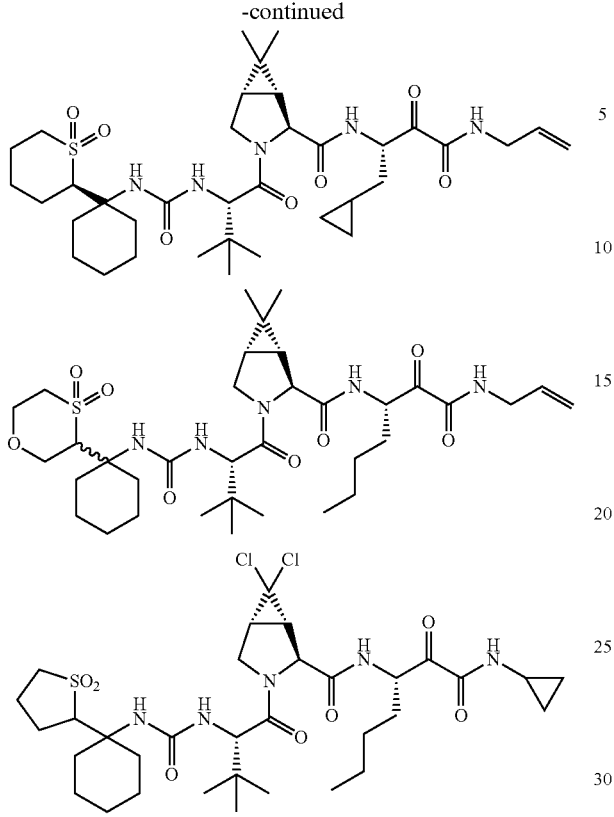
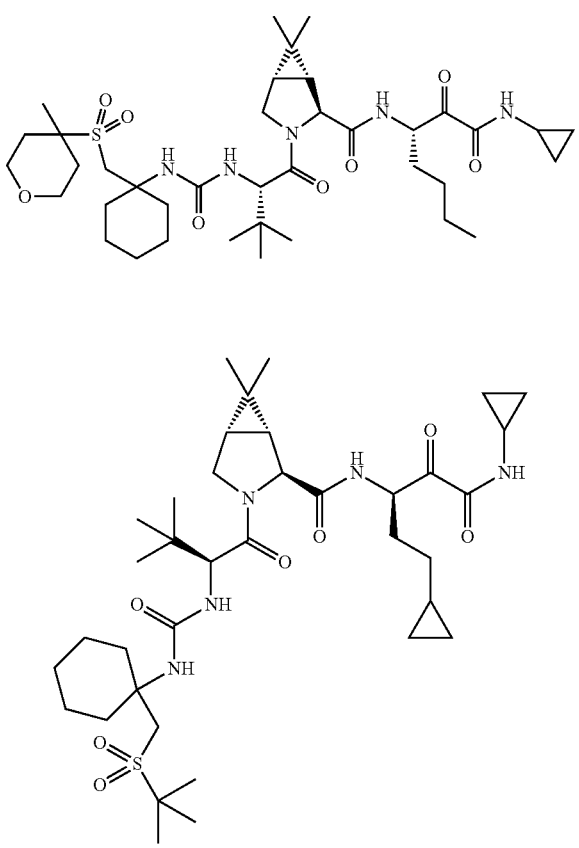
154
-continued
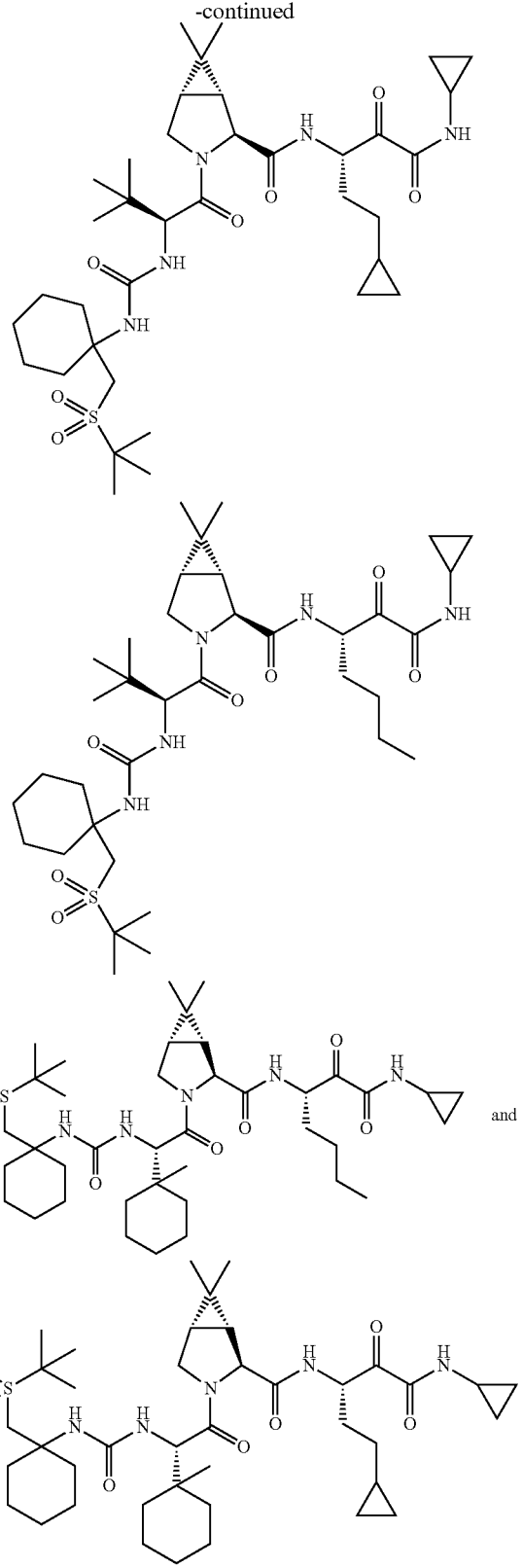
and pharmaceutically acceptable salts thereof.
Viral replication inhibitors useful in the present compositions and methods include, but are not limited to, HCV replicase inhibitors, IRES inhibitors, NS4A inhibitors, NS3 helicase inhibitors, NS5A inhibitors, ribavirin, AZD-2836 (Astra Zeneca), BMS-790052 (Bristol-Myers Squibb), viramidine, A-831 (Arrow Therapeutics); an antisense agent or a therapeutic vaccine.

In one embodiment, viral replication inhibitors useful in the present compositions and methods include, but are not limited to, HCV replicase inhibitors, IRES inhibitors, NS4A inhibitors, NS3 helicase inhibitors and NS5A inhibitors.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C(Inovio/Tripep), PeviPRO™ (Pevion Biotect), HCV/MF59-(Chiron/Novartis) and Civacir (NABI).

Examples of further additional therapeutic agents useful in the present compositions and methods include, but are not limited to, TT033 (Benitec/Tacere Bio/Pftzer), Sirna-034 (Sirna Therapeutics), GNI-104 (GENimmune), GI1-5005 (GlobeImmune); IDX-102 (Idenix), Levovirin™ (ICN Pharmaceuticals, Costa Mesa, Calif.); Humax (Genmab), ITX-2155 (Ithrex/Novartis), PRO 206 (Progenies), HepaCide-I (NanoVirocides), MX3235 (Migenix), SCY-635 (Scynexis); KPE02003002 (Kemin Pharma), Lenocta (VioQuest Pharmaeeuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen-Ken-Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of a viral infection or virus-related disorder can be determined by the attending clinician, taking into consideration the approved doses and dosage regimen in the package insert; the age, sex and general health of the patient; and the type and severity of the viral infection or related disease or disorder. When administered in combination, the Substituted Fused Tricyclic Compound(s) and the other agent(s) can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

Generally, a total daily dosage of the at least one Substituted Fused Tricyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 5.00 to about 1500 mg/day, administered in a single dose or in 2-4-divided doses. In still another embodiment, the dosage is from about 500 to about 1000 mg/day; administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU(12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmnann-La Roche), this agent is administered at a daily dosage of from about 600 to about 1400 mg/day for at least 24 weeks.

In one embodiment, one or more compounds of the present invention are administered with one or more additional therapeutic agents selected from an HCV protease inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an HCV replication inhibitor, a nucleoside, an interferon, a pegylated interferon and ribavirin.

In another embodiment, one or more compounds of the present invention are administered with two additional therapeutic agents selected from an HCV protease inhibitor, an HCV replication inhibitor, a nucleoside, an interferon, a pegylated interferon and ribavirin.

In a specific embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents-selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protcase inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication-inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

Compositions and Administration

Due to their activity, the Fused Tricyclic Compounds are useful in veterinary and human medicine. As described above, the Fused Tricyclic Compounds are useful for treating or preventing a viral infection or a virus-related disorder in a patient in need thereof.

When administered to a patient, the Fused Tricyclic Compounds can be administered as a component of a composition that comprises a pharmaceutically acceptable carrier or vehicle. The present invention provides pharmaceutical compositions comprising an effective amount of at least one Fused Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical-practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Fused Tricyclic Compounds of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tricyclic Compounds are administered orally.

In another embodiment, the one or more Fused Tricyclic Compounds are administered intravenously.

In another embodiment, the one or more Fused Tricyclic Compounds are administered topically.

In still another embodiment, the one or more Fused Tricyclic Compounds are administered sublingually.

In one embodiment, a pharmaceutical preparation comprising at least one Fused Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Compound(s) by weight or volume. In various embodiments, the present compositions can contain, in one embodiment, from about 1% to about 70% or from about 5% to about 60% of the Fused Tricyclic Compound(s) by weight or volume.

The quantity of Fused Tricyclic Compound in a unit dose of preparation may be varied or adjusted from about 1 mg to about 2500 mg. In various embodiments, the quantity is from about 10 mg to about, 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Compounds will be regulated according to the judgment of the attending clinician considering such factors as age, condition and size of the patient as well as severity of the symptoms being treated. Generally, a total daily dosage of the Fused Tricyclic Compounds range from about 0.1 to about 2000-mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Fused Tricyclic Compound or a pharmaceutically acceptable salt thereof; (ii) one or more additional therapeutic agents that are not a Fused Tricyclic Compound; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one Fused Tricyclic Compound, or a pharmaceutically acceptable salt of said compound and a pharmaceutically acceptable carrier, vehicle or diluent.

In another aspect the present invention provides a kit comprising an amount of at least one Fused Tricyclic Compound, or a pharmaceutically acceptable salt of said compound and an amount of at least one additional therapeutic agent listed above; wherein the amounts of the two or more active ingredients result in a desired therapeutic effect. In one embodiment, the one or more Fused Tricyclic Compounds and the one or more additional therapeutic agents are provided in the same container. In one embodiment, the one or more Fused Tricyclic Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

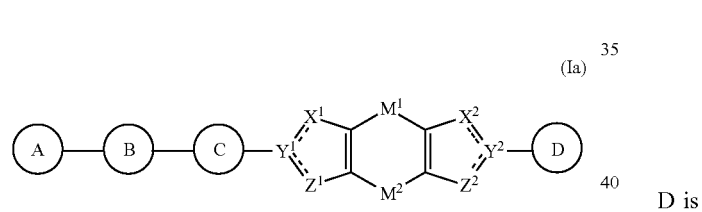

(Ia)

or a pharmaceutically acceptable salt thereof, wherein:

A is

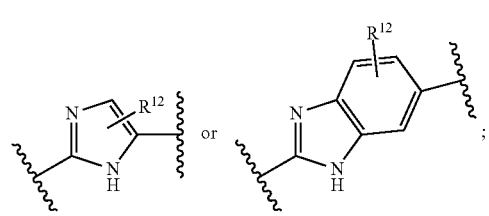

B is

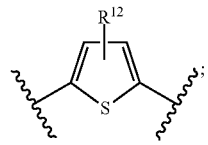

C is a bond or

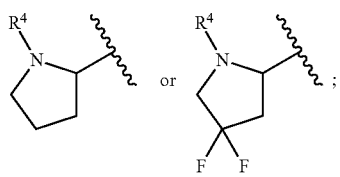

D is

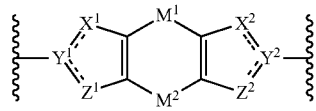

the group:

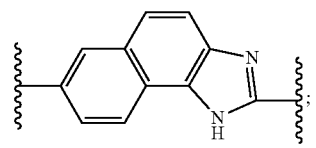 [SMILES: *c1ccc2c(ccc3nc(*)[nH]c32)c1]

has the structure:

each occurrence of $R^1$ is independently $C_1$-$C_6$ alkyl;
each occurrence of $R^4$ is independently —C(O)—[C($R^7$)$_2$]$_q$N($R^6$)$_2$, —C(O)—[C($R^7$)$_2$]$_q$N($R^6$)C(O)—$R^1$, —C(O)—[C($R^7$)$_2$]$_q$N($R^6$)C(O)O—$R^1$, —C(O)—[C($R^7$)$_2$]$_q$C(O)O—$R^1$, —C(O)[C($R^7$)$_2$]$_q$N($R^6$)SO$_2$—$R^1$ or -alkylene-N($R^6$)—[C($R^7$)$_2$]$_q$—N($R^6$)—C(O)O—$R^1$;
each occurrence of $R^6$ is H;
each occurrence of $R^7$ is independently $C_1$-$C_6$ alkyl or 3 to 7-membered cycloalkyl;
each occurrence of $R^{12}$ is independently H, $^2$H, $C_1$-$C_6$ alkyl, 3 to 7-membered cycloalkyl, or halo; and
each occurrence of q is independently an integer ranging from 1 to 4;
provided that the compound of formula (I) is other than:

2. The compound of claim 1, wherein A and D are each:

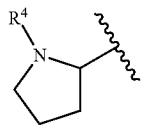

and each occurrence of $R^4$ is:

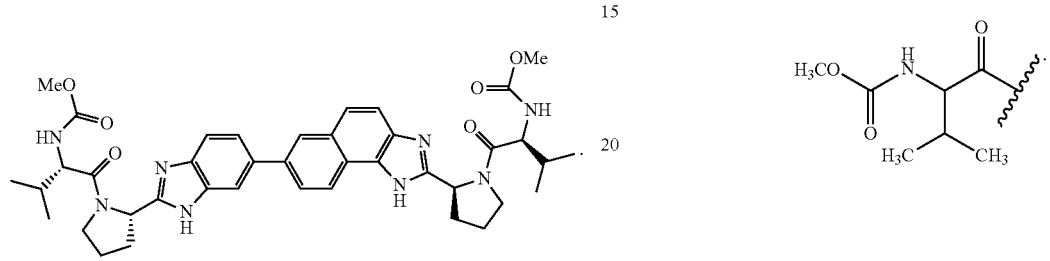

3. A compound having the structure:

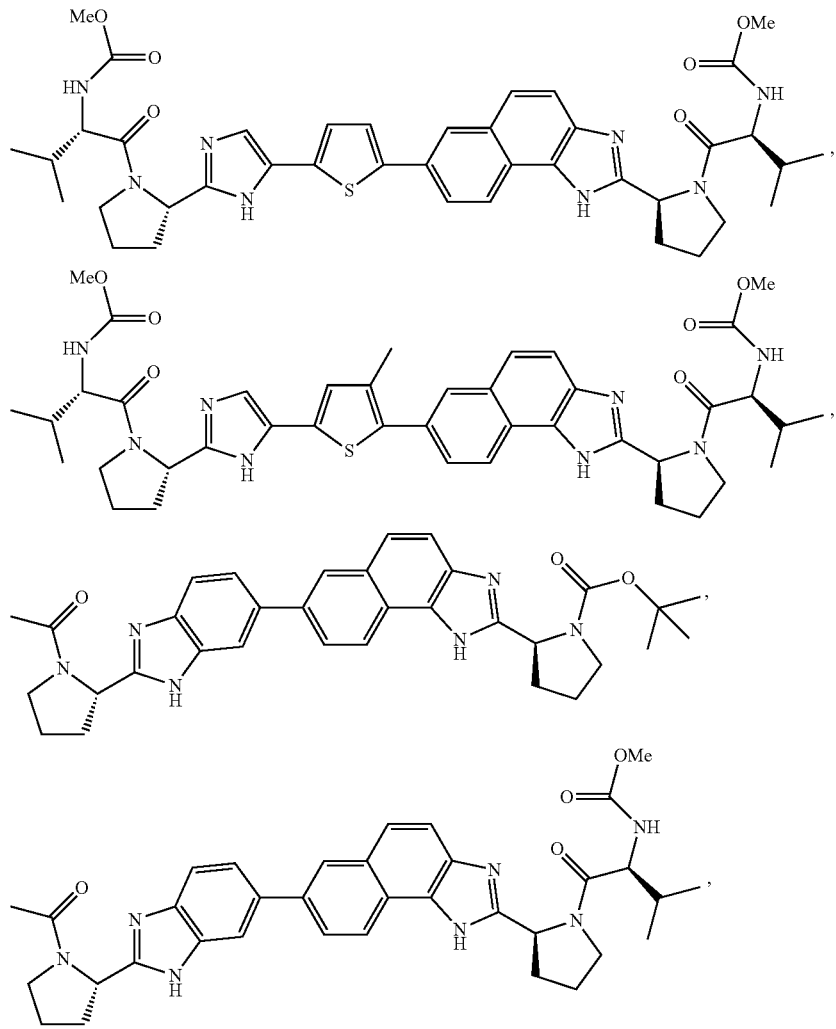

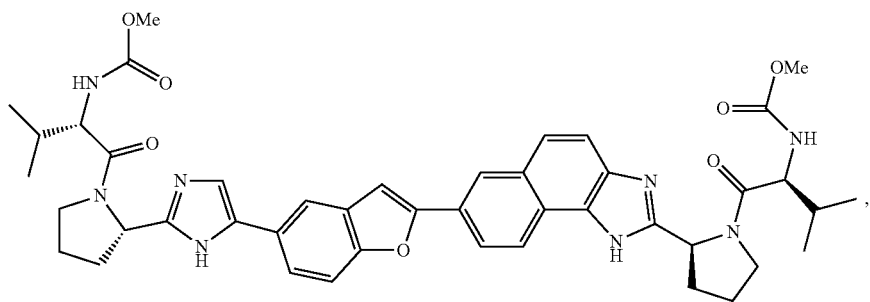
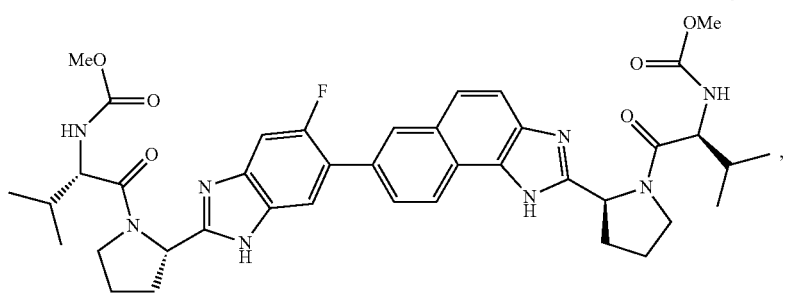
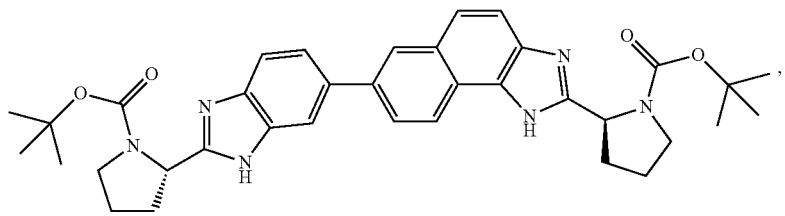
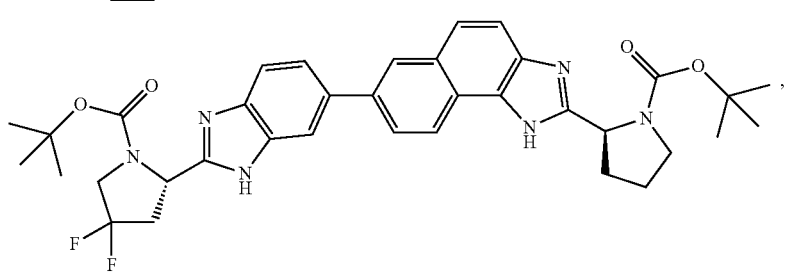
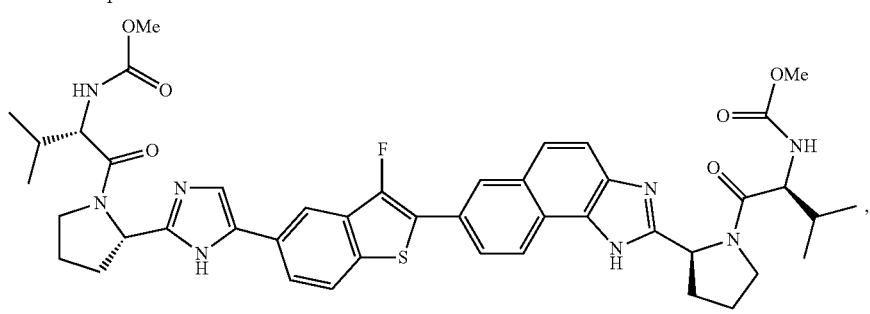
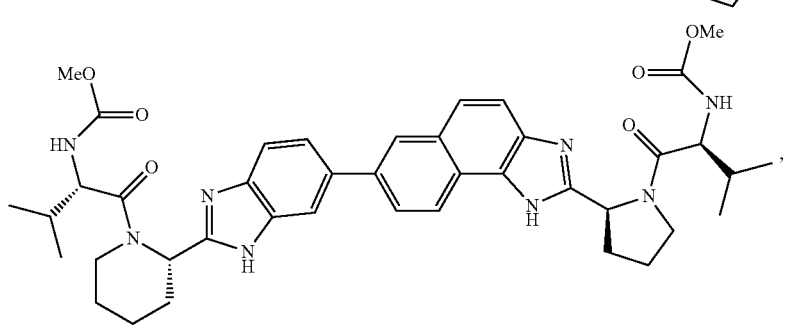

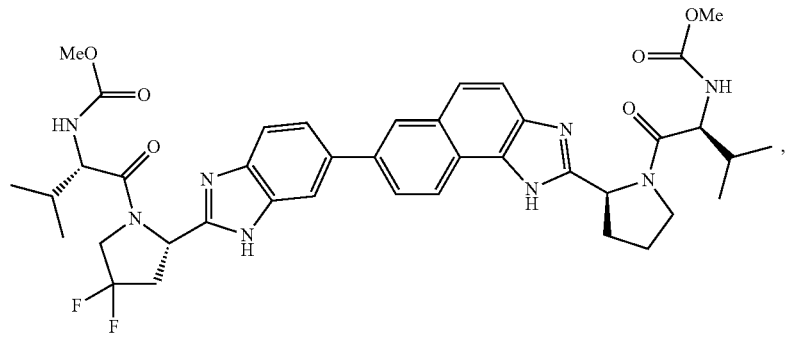
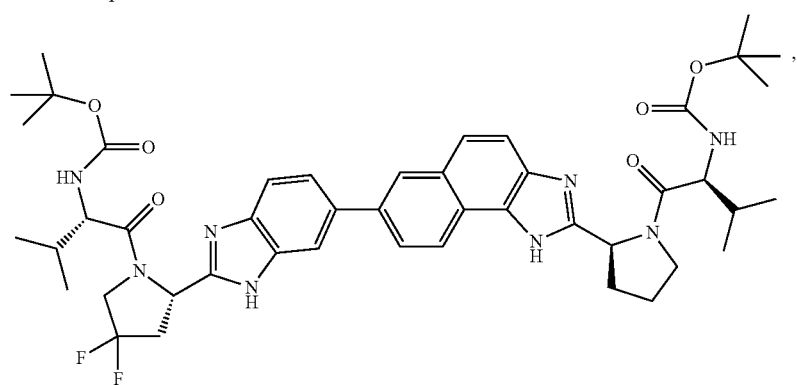
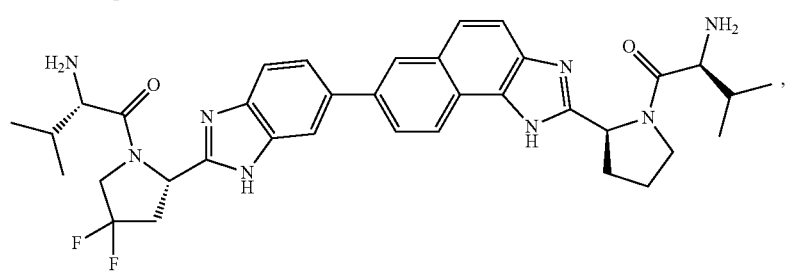
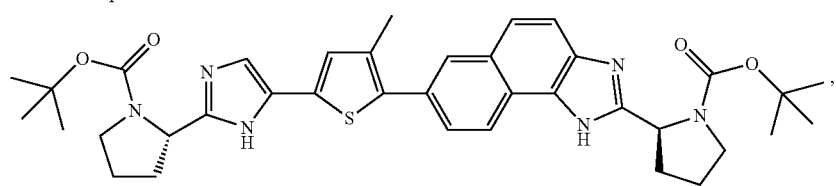
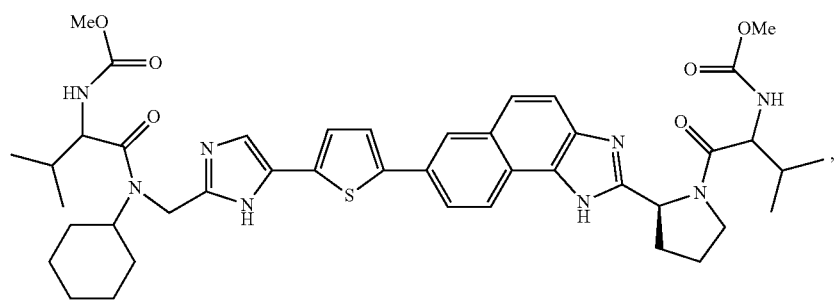
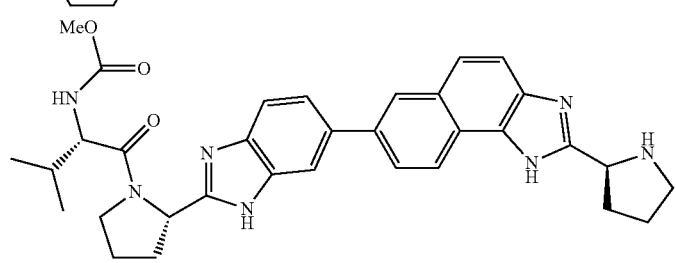

-continued
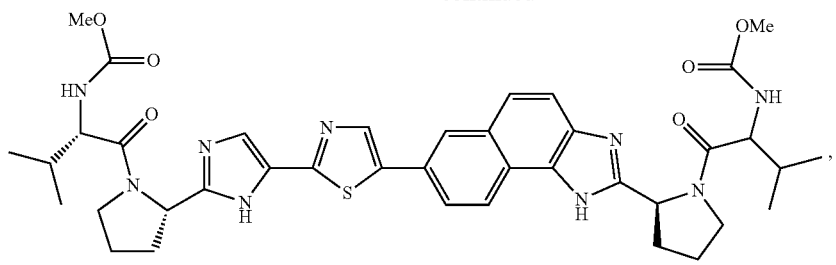
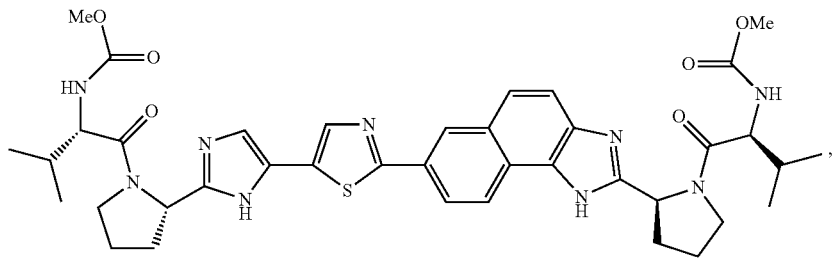
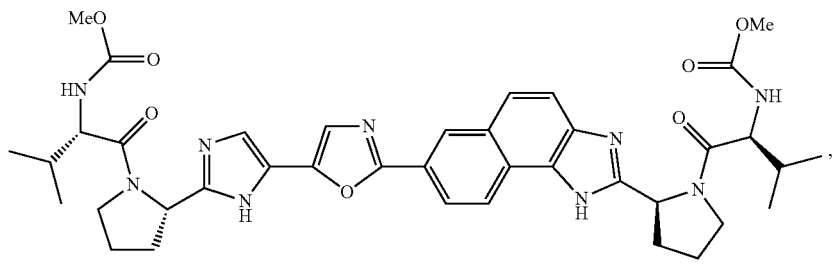
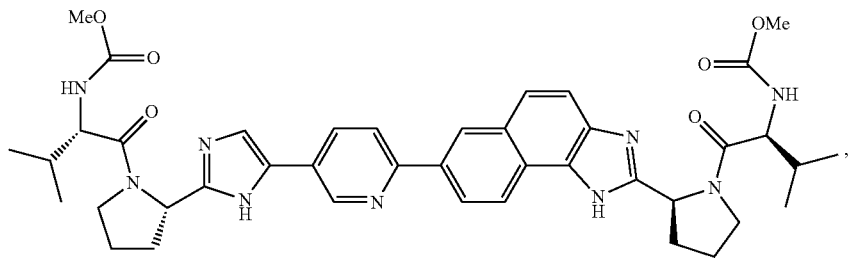
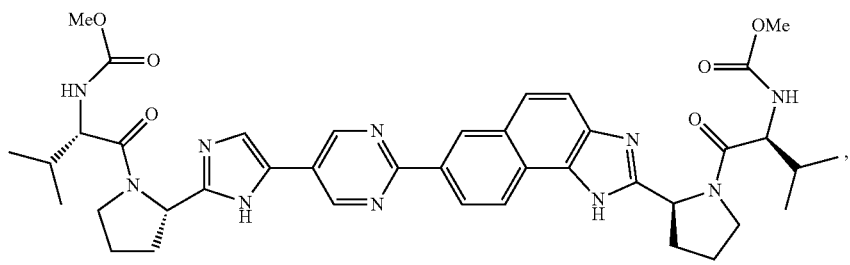
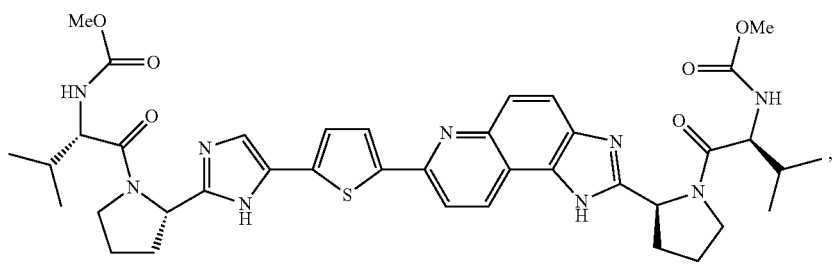

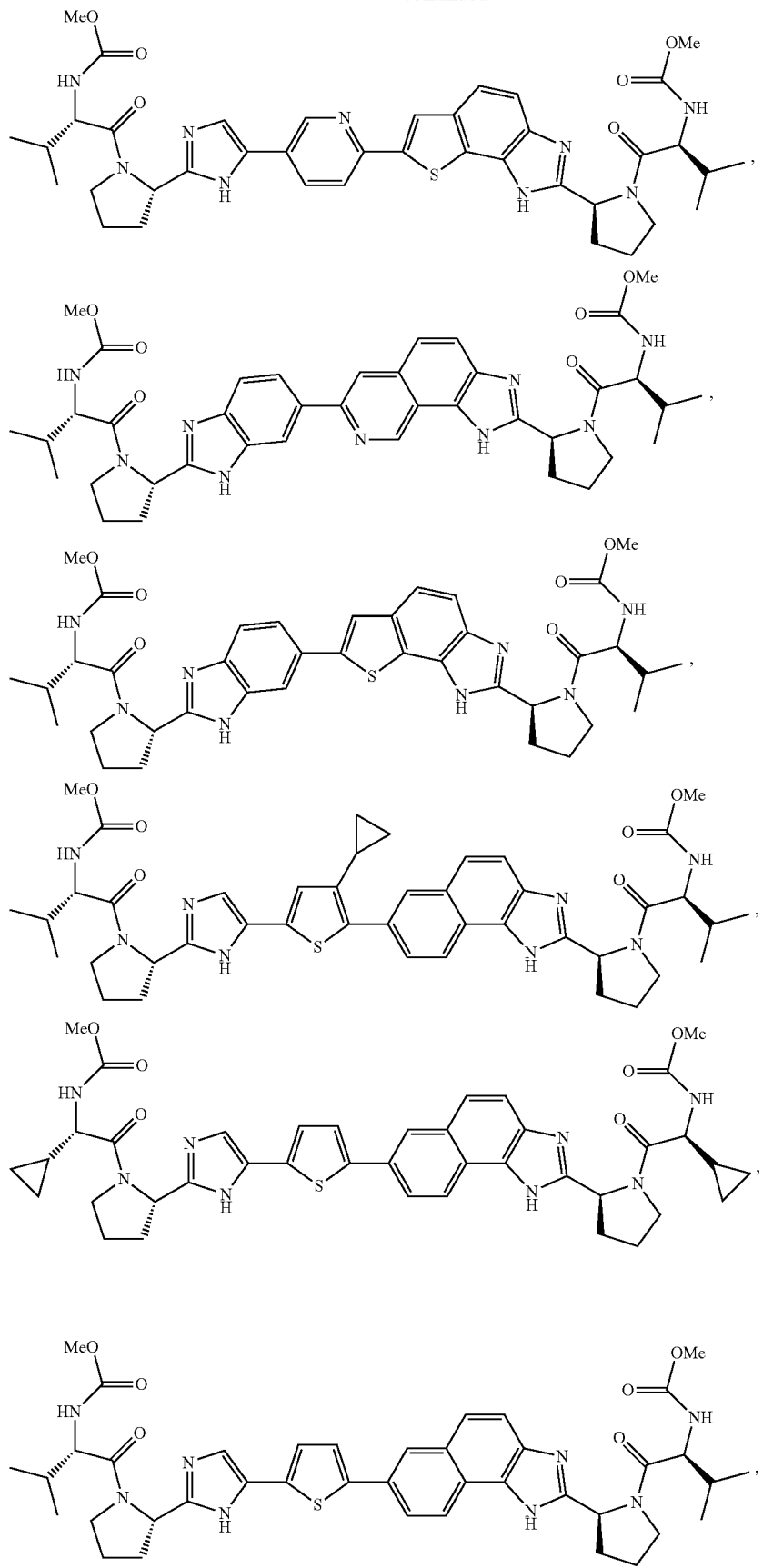

-continued
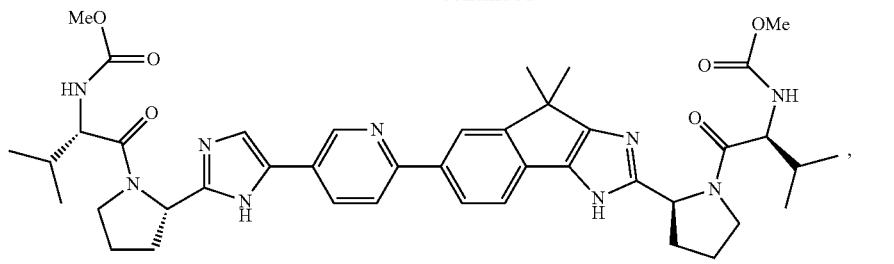
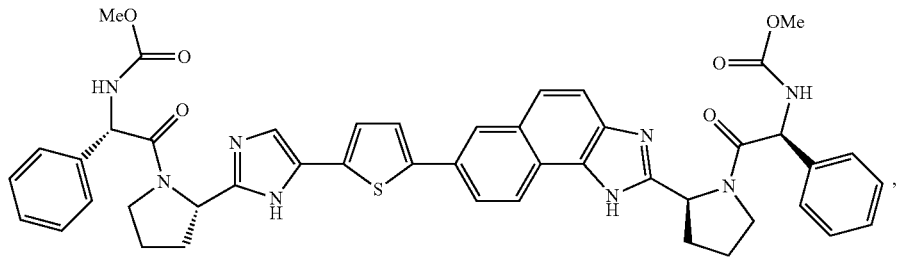
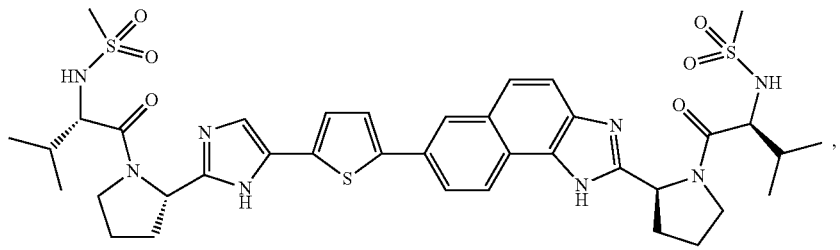
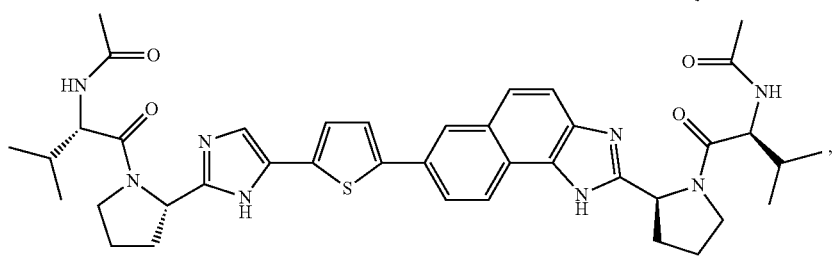
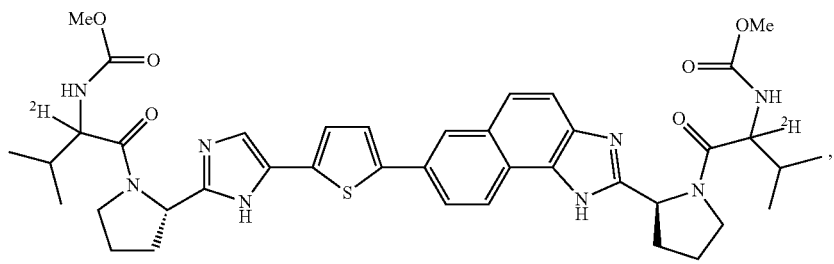
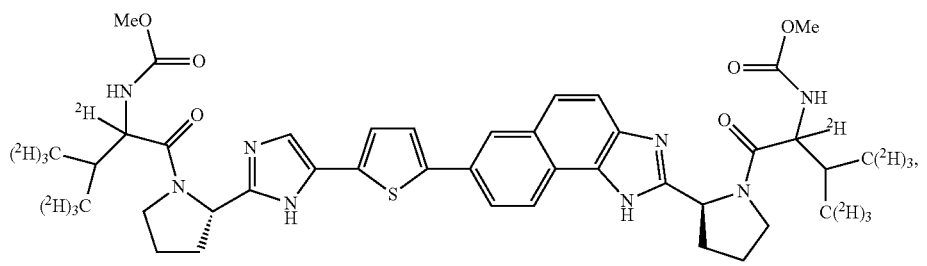

-continued
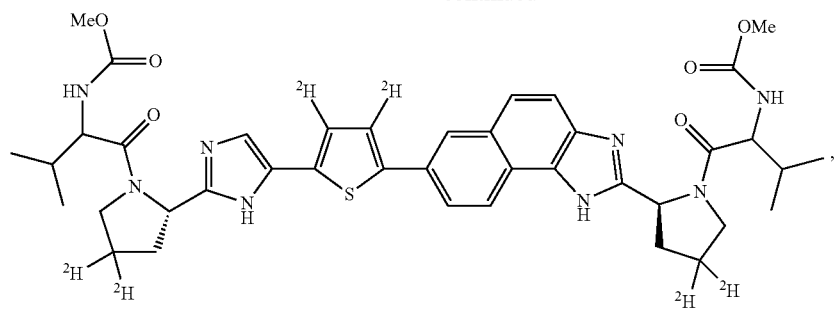
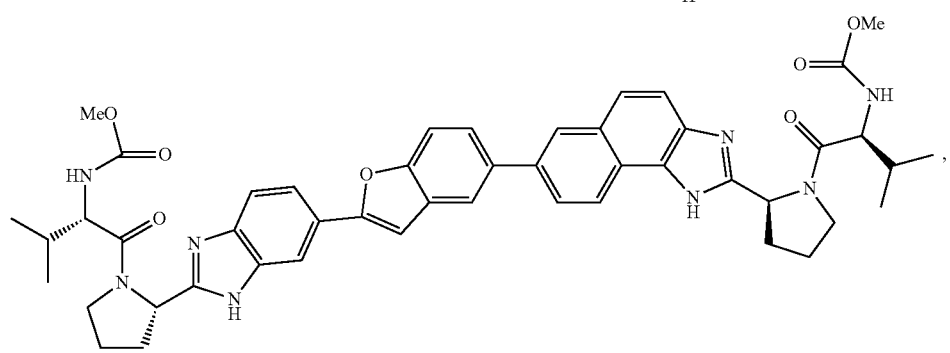
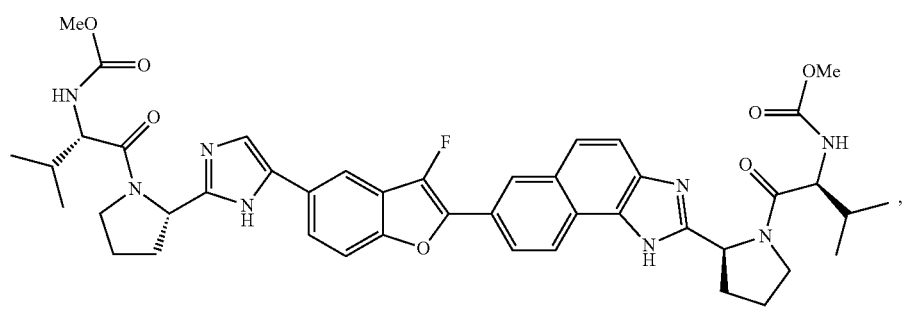
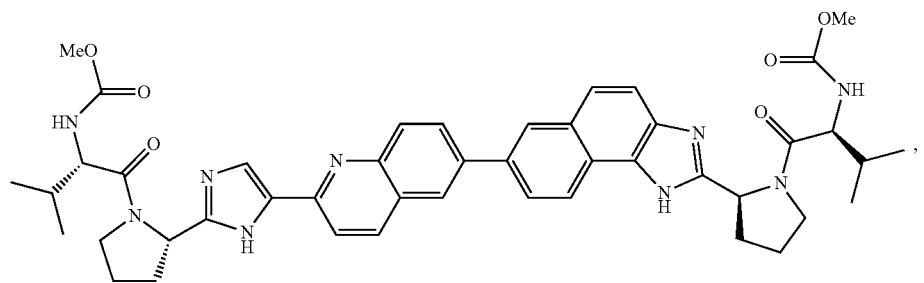
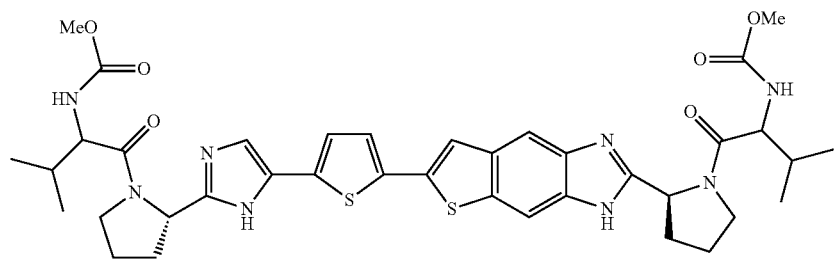

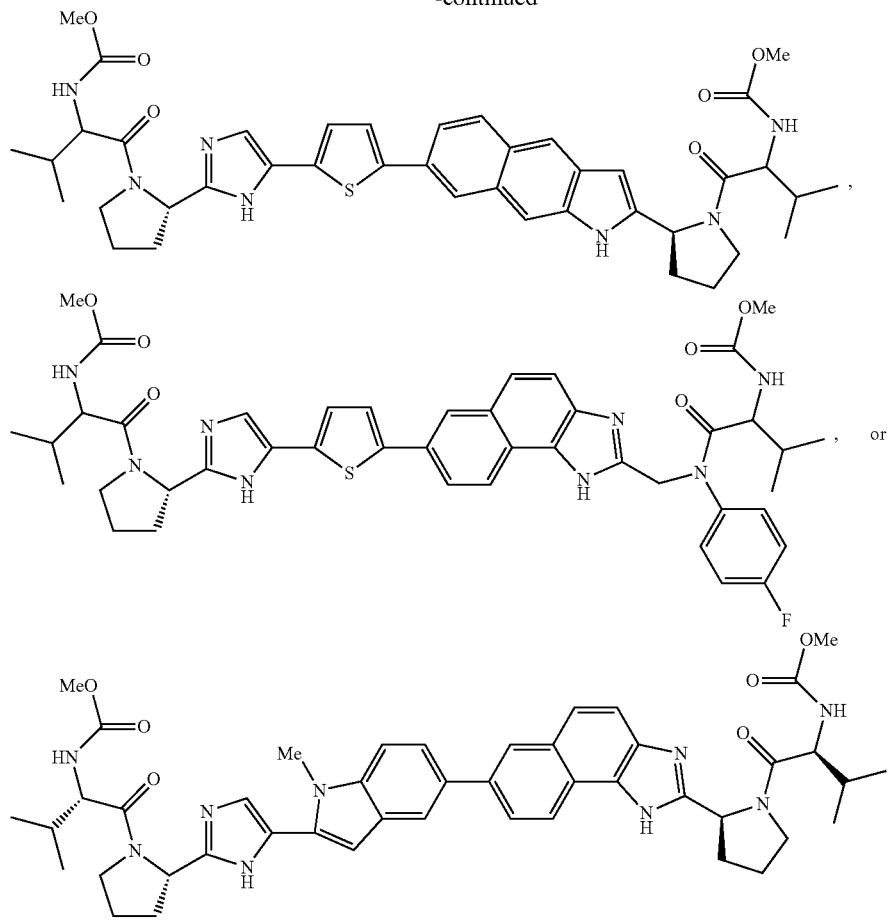

or a pharmaceutically acceptable salt thereof.

4. A pharmaceutical composition comprising an effective amount of a compound of claim 1, or a pharmaceutically acceptable salt thereof, and at least one pharmaceutically acceptable carrier.

5. The pharmaceutical composition of claim 4, further comprising at least one additional therapeutic agent, wherein the at least one additional therapeutic agent is not a compound of claim 1 and wherein the at least one additional therapeutic agent is selected from an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, and an antibody therapy (monoclonal or polyclonal).

6. A method for treating HCV infection in a patient, the method comprising administering to the patient an effective amount of a compound of claim 1, or a pharmaceutically acceptable salt thereof.

7. The method of claim 6, further comprising administering to the patient an effective amount of at least one additional therapeutic agent, wherein the at least one additional therapeutic agent is not a compound of claim 1 and wherein the at least one additional therapeutic agent is selected from an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, and an antibody therapy (monoclonal or polyclonal).

* * * * *